United States Patent
Egan et al.

(10) Patent No.: US 6,984,633 B2
(45) Date of Patent: Jan. 10, 2006

(54) METHOD TO TREAT CARDIOFIBROSIS WITH A COMBINATION THERAPY OF AN ANGIOTENSIN II ANTAGONIST AND EPOXYMEXRENONE

(75) Inventors: James J. Egan, Winnetka, IL (US); Ellen G. McMahon, St. Louis, MO (US); Gillian M. Olins, Glencoe, MO (US); Joseph R. Schuh, St. Louis, MO (US)

(73) Assignee: G.D Searle & Co., St. Louis, MO (US)

( * ) Notice: Subject to any disclaimer, the term of this patent is extended or adjusted under 35 U.S.C. 154(b) by 0 days.

(21) Appl. No.: 10/371,699

(22) Filed: Feb. 21, 2003

(65) Prior Publication Data

US 2004/0053903 A1 Mar. 18, 2004

Related U.S. Application Data

(63) Continuation of application No. 09/506,068, filed on Feb. 17, 2000, now abandoned, which is a continuation of application No. 09/317,237, filed on May 24, 1999, now abandoned, which is a continuation of application No. 09/181,586, filed on Oct. 28, 1998, now abandoned, which is a division of application No. 08/980,734, filed on Dec. 1, 1997, now abandoned, which is a continuation of application No. 08/783,404, filed on Jan. 13, 1997, now abandoned, which is a continuation of application No. 08/486,085, filed on Jun. 7, 1995, now abandoned.

(51) Int. Cl.
| A61K 31/56 | (2006.01) |
|---|---|
| A61K 31/58 | (2006.01) |
| A61K 31/585 | (2006.01) |
| A61K 31/41 | (2006.01) |
| A61K 31/535 | (2006.01) |

(52) U.S. Cl. .................. 514/171; 514/170; 514/173; 514/175; 514/381; 514/234.8; 514/259; 514/340; 514/359; 514/210; 514/307

(58) Field of Classification Search .............. 514/171, 514/170, 173, 175, 307, 259, 340, 359, 210, 514/234.8, 381
See application file for complete search history.

(56) References Cited

U.S. PATENT DOCUMENTS

| 4,559,332 A | * | 12/1985 | Grob et al. ................ 514/175 |
| 5,350,752 A | * | 9/1994 | Poss et al. ............. 514/266.23 |
| 5,380,719 A | * | 1/1995 | Kim .......................... 514/85 |
| 5,401,736 A | * | 3/1995 | Enari et al. ............ 514/210.18 |
| 5,466,704 A | * | 11/1995 | Poss ......................... 514/381 |
| 5,525,614 A | * | 6/1996 | Blankley et al. ............ 514/307 |

FOREIGN PATENT DOCUMENTS

| EP | 0122232 | 10/1984 |
| EP | 0481448 A1 | 4/1991 |
| WO | WO 9112001 A1 | 8/1991 |
| WO | WO 9115206 A1 | 10/1991 |
| WO | WO 9409778 A1 | 5/1994 |
| WO | WO 9515166 A1 | 6/1995 |

OTHER PUBLICATIONS

Schrieber et al. "Failure of the aldosterone antagonist spironolactone to inhibit myocardial hypertrophy produced by . . . ," Physiologia Bohemoslovaca, 1980, vol. 29, No. 6, pp. 577–579, Medline Abstract, AN 81151365.*
CAPlus Abstract, AN: 1995:386737, Katayama et al., 1995.*
Brilla et al., J. Mol. Cell. Cardiol., vol. 25, p. 563–575, 1993.*
Gasparo et al., J. Pharm. Exp. Ther., vol. 240(2), p. 650–656, 1987.*
The Journal of Steroid Biochemistry, vol. 32, No. 1b, 1989, pp. 223–227, De Gasparo et al., "Antialdosterone: Incidence and Prevention of Sexual Side Effects".
The Journal of Pharmacology and Experimental Therapeutics, vol. 240, No. 2, 1987, pp. 650–656, De Gasparo et al.: "Three New Epoxy–Spirolactone Derivatives: Characterization in Vivo and in Vitro".

* cited by examiner

Primary Examiner—Shengjun Wang
(74) Attorney, Agent, or Firm—Joseph R. Schuh; Charles Ashbrook

(57) ABSTRACT

A therapeutic method is described for treating cardiofibrosis or cardiac hypertrophy using a combination therapy comprising a therapeutically-effective amount of an angiotensin II receptor antagonist and a therapeutically-effective amount of expoxymexrenone.

24 Claims, No Drawings

METHOD TO TREAT CARDIOFIBROSIS WITH A COMBINATION THERAPY OF AN ANGIOTENSIN II ANTAGONIST AND EPOXYMEXRENONE

This application is a continuation of application Ser. No. 09/506,068 filed Feb. 17, 2000, now abandoned, which is a continuation of application Ser. No. 09/317,237 filed May 24, 1999, now abandoned, which is a continuation of application Ser. No. 09/181,586 filed Oct. 28, 1998, now abandoned, which is a continuation of application Ser. No. 08/980,734, filed Dec. 1, 1997, now abandoned, which is a continuation of application Ser. No. 08/783,404, filed on Jan. 13, 1997, now abandoned, which is a continuation of application Ser. No. 08/486,085 filed Jun. 7, 1995, now abandoned.

FIELD OF THE INVENTION

Therapeutic methods are described for treatment of cardiofibrosis and cardiac hypertrophy. Of particular interest are therapies using an epoxy-containing steroidal aldosterone receptor antagonist compound such as epoxymexrenone in combination with an angiotensin II receptor antagonist compound.

BACKGROUND OF THE INVENTION

Myocardial (or cardiac) failure, whether a consequence of a previous myocardial infarction, heart disease associated with hypertension, or primary cardiomyopathy, is a major health problem of worldwide proportions. The incidence of symptomatic heart failure has risen steadily over the past several decades.

In clinical terms, decompensated cardiac failure consists of a constellation of signs and symptoms that arises from congested organs and hypoperfused tissues to form the congestive heart failure (CHF) syndrome. Congestion is caused largely by increased venous pressure and by inadequate sodium ($Na^+$) excretion, relative to dietary $Na^+$ intake, and is importantly related to circulating levels of aldosterone (ALDO). An abnormal retention of $Na^+$ occurs via tubular epithelial cells throughout the nephron, including the later portion of the distal tubule and cortical collecting ducts, where ALDO receptor sites are present.

ALDO is the body's most potent mineralocorticoid hormone. As connoted by the term mineralocorticoid, this steroid hormone has mineral-regulating activity. It promotes $Na^+$ reabsorption not only in the kidney, but also from the lower gastrointestinal tract and salivary and sweat glands, each of which represents classic ALDO-responsive tissues. ALDO regulator $Na^+$ and water resorption at the expense of potassium ($K^+$) and magnesium ($M^{1-}$) excretion.

ALDO can also provoke response in nonepithelial cells. Elicited by a chronic elevation in plasma ALDO level that is inappropriate relative to dietary $Na^+$ intake, these responses can have adverse consequences on the structure of the cardiovascular system. Hence, ALDO can contribute to the progressive nature of myocardial failure for multiple reasons.

Multiple factors regulate ALDO synthesis and metabolism, many of which are operative in the patient with myocardial failure. These include renin as well as non-reindependent factors (such as $K^+$, ACTH) that promote ALDO synthesis. Hepatic blood flow, by regulating the clearance of circulating ALDO, helps determine its plasma concentration, an important factor in heart failure characterized by reduction in cardiac output and hepatic blood flow.

The renin-angiotensin-aldosterone system (RAAS) is one of the hormonal mechanisms involved in regulating pressure/volume homeostasis and also in the development of hypertension. Activation of the renin-angiotensin-aldosterone system begins with renin secretion from the juxtaglomerular cells in the kidney and culminates in the formation of angiotensin II, the primary active species of this system. This octapeptide, angiotensin II, is a potent vasoconstrictor and also produces other physiological effects such as stimulating aldosterone secretion, promoting sodium and fluid retention, inhibiting renin secretion, increasing sympathetic nervous system activity, stimulating vasopressin secretion, causing positive cardiac inotropic effect and modulating other hormonal systems.

Previous studies have shown that antagonizing angiotensin II binding at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, early descriptions of such non-peptidic compounds include the sodium salt of 2-n-butyl-4-chloro-1-(2-chlorobenzyl)imidazole-5-acetic acid which has specific competitive angiotensin II antagonist activity as shown in a series of binding experiments, functional assays and in vivo tests [P. C. Wong et al., *J. Pharmacol. Exp. Ther.*, 247(1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al., *European J. Pharmcol.*, 157, 31–21 (1988)]. A family of 1-benzylimidazole-5-acetate derivatives has been shown to have competitive angiotensin II antagonist properties [A. T. Chiu et al., *J. Pharmacol. Exp. Ther.*, 250(3), 867–874 (1989)]. U.S. Pat. No. 4,816,463 to Blankey et al describes a family of 4,5,6,7-tetrahydro-1H-imidazol(4,5-c)-tetrahydro-pyridine derivatives useful as antihypertensives, some of which are reported to antagonize the binding of labelled angiotensin II to rat adrenal receptor preparation and thus case a significant decrease in mean arterial blood pressure in conscious hypertensive rats. Other families of non-peptidic angiotensin II antagonists have been characterized by molecules having a biphenylmethyl moiety attached to a heterocyclic moiety. For example, EP No. 253,310, published Jan. 20, 1998, describes a series of aralkyl imidazole compounds, including in particular a family of biphenylmethyl substituted imidazoles, as antagonists to the angiotensin II receptor. EP No. 323,814 published Jul. 12, 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

Many aldosterone receptor blocking drugs are known. For example, spironolactone is a drug which acts at the mineralocorticoid receptor level by competitively inhibiting aldosterone binding. This steroidal compound has been used for blocking aldosterone-dependent sodium transport in the distal tubule of the kidney in order to reduce edema and to treat essential hypertension and primary hyperaldosteronism [F. Mantero et al., *Clin. Sinc. Mol. Med.*, 45 (Suppl 1), 219s–224s (1973)]. Spironolactone is also used commonly in the treatment of other hyperalodsterone-related diseases such as liver cirrhosis and congestive heart failure (F. J. Saunders et al., *Aldactone; Spironolactone: A Comprehensive Review*, Searle, N.Y. (1978)]. Progressively-increasing doses of spironolactone from 1 mg to 400 mg per day [i.e., 1 mg/day, 5 mg/day, 20 mg/day] were administered to a spironlactone-intolerant patient to treat cirrhosis-related ascites [P. A. Greenberger et al., *N. Eng. Reg. Allergy Proc.*, 7(4), 343–345 (Jul.–Aug., 1986)]. It has been recognized that development of myocardial fibrosis is sensitive to circulating levels of both Angiotensin II and aldosterone, and that the aldosterone antagonist spironolactone prevents myocardial fibrosis in animal models, thereby linking aldosterone to excessive collagen deposition [D. Klug et al. *Am. J. Cardiol.*, 71 (3), 46A–54A (1993)]. Spironolactone has been shown in prevent fibrosis in animal models irrespective of the development of left ventricular hypertrophy and the presence of hypertension [C. G. Brilla et al., *J. Mol. Cell. Cardiol.*, 25(5), 563–575 (1993)]. Spironolactone at a dosage ranging from 25 mg to 100 mg daily is used to treat diuretic-induced hypokalemia, when orally-administered potassium supplements or other potassium-sparing regimens are considered inappropriate [*Physicians' Desk Reference*, 46th Edn., p. 2153, Medical Economics Company Inc., Montvale, N.J. (1992)].

Previous studies have shown that inhibiting ACE inhibits the renin-angiotensin system by substantially complete blockade of the formation of angiotensin II. Many ACE inhibitors have been used clinically to control hypertension. While ACE inhibitors may effectively control hypertension, side effects are common including chronic cough, skin rash, loss of taste sense, proteinuria and neutropenia.

Moreover, although ACE inhibitors effectively block the formation of angiotensin II, aldosterone levels are not well controlled in certain patients having cardiovascular diseases. For example, despite continued ACE inhibition in hypertensive patients receiving captopril, there has been observed a gradual return of plasma aldosterone to baseline levels [J. Staessen et al., *J. Endocrinol.*, 91, 457–465 (1981)]. A similar effect has been observed for patients with myocardial infarction receiving zofenopril [C. Borghi et al., *J. Clin. Pharmacol.*, 33, 40–45 (1993)]. This phenomenon has been termed "aldosterone escape".

Another series of steroidal-type aldosterone receptor antagonists is exemplified by epoxy-containing spironolactone derivatives. For example, U.S. Pat. No. 4,559,332 issued to Grob et al describes 9α,11α-epoxy-containing spironolactone derivatives as aldosterone antagonists useful as diuretics. These 9α,11α-epoxy steroids have been evaluated for endocrine effects in comparison to spironolactone [M. de Gasparo et al., *J. Pharm. Exp. Ther.*, 240(2), 650–656 (1987)].

Combinations of an aldosterone antagonist and an ACE inhibitor have been investigated for treatment of heart failure. It is known that mortality is higher in patients with elevated levels of plasma aldosterone and that aldosterone levels increase as CHF progresses from activation of the Renin-Angiontensin-Aldosterone System (RAAS). Routine use of a diuretic may further elevate aldosterone levels. ACE inhibitors consistently inhibit angiotensin II production but exert only a mild and transient antialdosterone effect.

Combining an ACE inhibitor and spironolactone has been suggested to provide substantial inhibition of the entire RAAS. For example, a combination of enalapril and spironolactone has been administered to ambulatory patients with monitoring of blood pressure [P. Poncelet et al., *Am. J. Cardiol.*, 65(2), 33K–35K (1990)]. In a 90-patient study, a combination of captopril and spironolactone was administered and found effective to control refractory CHF without serious incidents of hyperkalemia [U. Dahlstrom et al., *Am. J. Cardiol.*, 71, 29A–33A (Jan. 21, 1993)]. Spironolactone coadministered with an ACE inhibitor was reported to be highly effective in 13 of 16 patients afflicted with congestive heart failure [A. A. van Vliet et al., *Am. J. Cardiol.*, 71, 21A–28A (Jan. 21, 1993)]. Clinical improvements have been reported for patients receiving a co-therapy of spironolactone and the ACE inhibitor enalapril, although this report mentions that controlled trials are needed to determine the lowest effective doses and to identify which patients would benefit most from combined therapy [F. Cannad. *Am. J. Cardiol.*, 71(3), 34A–39A (1993)].

Combinations of an angiotensin II receptor antagonist and aldosterone receptor antagonist, are known. For example, PCT Application No. US91/09362 published Jun. 25, 1992 describes treatment of hypertension using a combination of an imidazole-containing angiotensin II antagonist compound and a diuretic such as spironolactone.

SUMMARY OF THE INVENTION

A therapeutic method for treating or preventing the progression of cardiofibrosis or cardiac hypertrophy is provided by a combination therapy comprising a therapeutically-effective amount of an epoxy-steroidal aldosterone receptor antagonist and a therapeutically-effective amount of an angiotensin II receptor antagonist.

The phrase "angiotensin II receptor antagonist" is intended to embrace one or more compounds or agents having the ability to interact with a receptor site located on various human body tissues, which site is a receptor having a relatively high affinity for angiotensin II and which receptor site is associated with mediating one or more biological functions or events such as vasoconstriction or vasorelaxation, kidney-mediated sodium and fluid retention, sympathetic nervous system activity, and in modulating secretion of various substances such as aldosterone, vasopressin and renin, to lower blood pressure in a subject susceptible to or afflicted with elevated blood pressure. Interactions of such angiotensin II receptor antagonist with this receptor site may be characterized as being either "competitive" (i.e., "surmountable") or as being "insurmountable". These terms, "competitive" and "insurmountable", characterize the relative rates, faster for the former term and slower for the latter term, at which the antagonist compound dissociates from binding with the receptor site.

The phrase "epoxy-steroidal aldosterone receptor antagonist" is intended to embrace one or more agents or compounds characterized by a steroid-type nucleus and having an epoxy moiety attached to the nucleus and which agent or compound binds to the aldosterone receptor, as a competitive inhibitor of the action of aldosterone itself at the receptor site, so as to modulate the receptor-mediated activity of aldosterone.

The phrase "combination therapy", in defining use of an angiotensin II antagonist and an epoxy-steroidal aldosterone receptor antagonist, is intended to embrace administration of each antagonist in a sequential manner in a regimen that will provide beneficial effects of the drug combination, and is intended to embrace co-administration of the antagonist agents in a substantially simultaneous manner, such as in a single capsule having a fixed ratio of active ingredients or in multiple, separate capsules for each antagonist agent.

The phrase "therapeutically-effective" is intended to qualify the amount of each antagonist agent for use in the combination therapy which will improve cardiac sufficiency by reducing or preventing the progression of myocardial fibrosis or cardiac hypertrophy.

Another combination therapy of interest would consist essentially of three active agents, namely, an AII antagonist, an aldosterone receptor antagonist agent and a diuretic.

For a combination of AII antagonist agent and an ALDO antagonist agent, the agents would be used in combination in a weight ratio range from about 0.5-to-one to about twenty-to-one of the AII antagonist agent to the aldosterone receptor antagonist agent. A preferred range of these two agents (AII antagonist-to-ALDO antagonist) would be from about one-to-one of about fifteen-to-one, while a more preferred range would be from about one-to-one to about five-to-one, depending ultimately on the selection of the AII antagonist the ALDO antagonist. The diuretic agent may be present in a ratio range of 0.1-to-one to about ten to one (AII antagonist to diuretic).

DETAILED DESCRIPTION OF THE INVENTION

Epoxy-steroidal aldosterone receptor antagonist compounds suitable for use in the combination therapy consist of these compounds having a steroidal nucleus substituted with an epoxy-type moiety. The term "epoxy-type" moiety is intended to embrace any moiety characterized in having an oxygen atom as a bridge between two carbon atoms, examples of which include the following moieties:

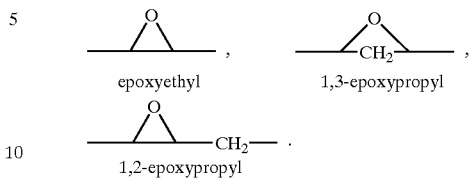

The term "steroidal", as used in the phrase "epoxy-steroidal", denotes a nucleus provided by a cyclopentenophenanthrene moiety, having the conventional "A", "B", "C" and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal aldosterone receptor antagonists suitable for use in combination therapy include a family of compounds having an epoxy moiety fused to the "C" ring of the steroidal nucleus. Especially preferred are 20-spiroxane compounds characterized by the presence of a 9α,11α-substituted epoxy moiety. Table I, below, describes a series of 9α,11α-epoxy-steroidal compounds which may be used in the combination therapy. These epoxy steroids may be prepared by procedures described in U.S. Pat. No. 4,559,332 to Grob et al issued Dec. 17, 1985.

TABLE I

Aldosterone Receptor Antagonists

| Compound # | Structure | Name |
|---|---|---|
| 1 | 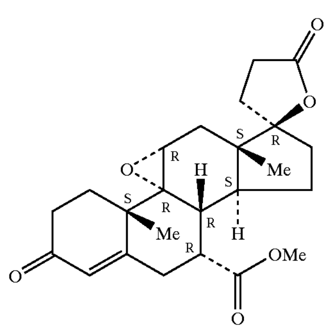 | Pregn-4-ene-7,21-dicarboxylic acid, 9,11-epoxy-17-hydroxy-3-oxo-,γ-lactone, methyl ester, (7α,11.α.,17α)- |
| 2 | 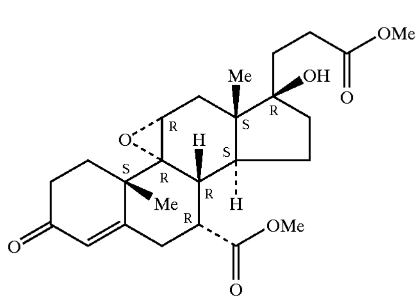 | Pregn-4-ene-7,21-dicarboxylic acid, 9,11-epoxy-17-hydroxy-3-oxo-dimethyl ester, (7α,11α,17α) |

TABLE I-continued

Aldosterone Receptor Antagonists

| Compound # | Structure | Name |
|---|---|---|
| 3 | 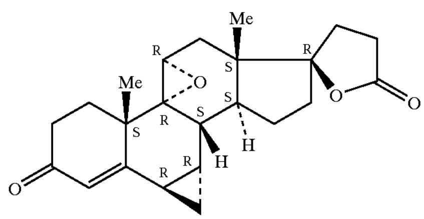 | 3'H-cyclopropa[6,7]pregna-4,6-diene-21-carboxylic acid, 9,11-epoxy-6,7-dihydro-17-hydroxy-3-oxo-,γ-lactone, (6β,7β,11β,17β)- |
| 4 | 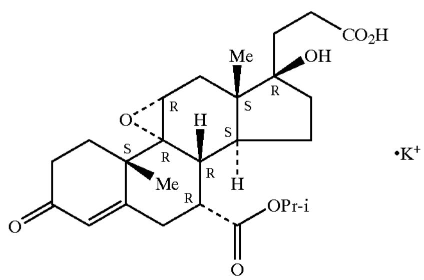 | Pregn-4-ene-7,21-dicarboxylic acid, 9,11-epoxy-17-hydroxy-3-oxo-, 7-(1-methylethyl) ester, monopotassium salt, (7α,11α,17α)- |
| 5 | 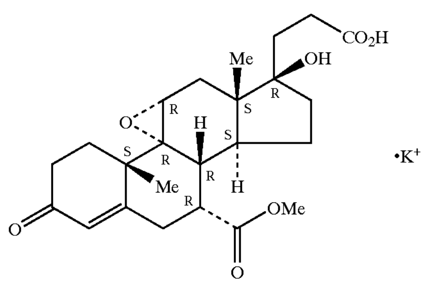 | Pregn-4-ene-7,21-dicarboxylic acid, 9,11-epoxy-17-hydroxy-3-oxo-,7-methyl ester, monopotassium salt, (7α,11α,17α)- |
| 6 | 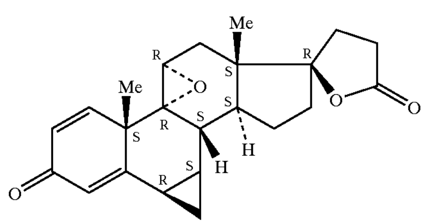 | 3'H-cyclopropa[6,7]pregna-1,4,6-triene-21-carboxylic acid, 9,11-epoxy-6,7-dihydro-17-hydroxy-3-oxo-,γ-lactone(6α,7α,11.α)- |
| 7 | 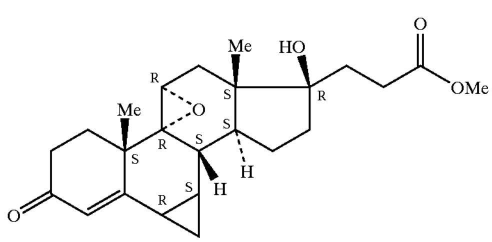 | 3'H-cyclopropa[6,7]pregna-4,6-diene-21-carboxylic acid, 9,11-epoxy-6,7-dihydro-17-hydroxy-3-oxo-, methyl ester, (6α,7α,11α,17α)- |
| 8 | 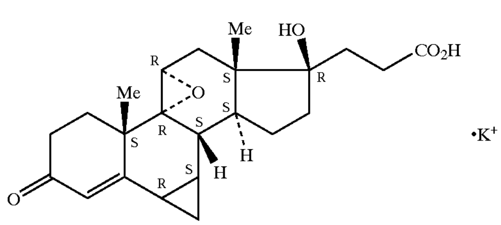 | 3'H-cyclopropa[6,7]pregna-4,6-diene-21-carboxylic acid, 9,11-epoxy-6,7-dihydro-17-hydroxy-3-oxo-, monopotassium salt, (6α,7α,11α,17α) |

TABLE I-continued

Aldosterone Receptor Antagonists

| Compound # | Structure | Name |
|---|---|---|
| 9 | 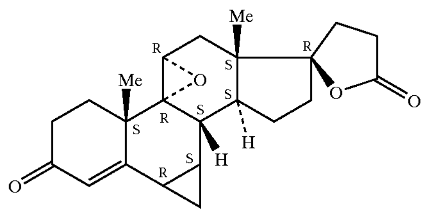 | 3'H-cyclopropa[6,7]pregna-4,6-diene-21-carboxylic acid, 9,11-epoxy-6,7-dihydro-17-hydroxy-3-oxo-,γ′ lactone, (6α,7α,11α.,17α)- |
| 10 | 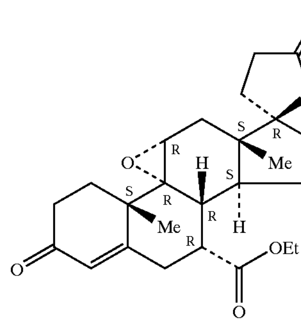 | Pregn-4-ene-7,21-dicarboxylic acid, 9,11-epoxy-17-hydroxy-3-oxo-,γ-lactone, ethyl ester, (7α,11α,17α)- |
| 11 | 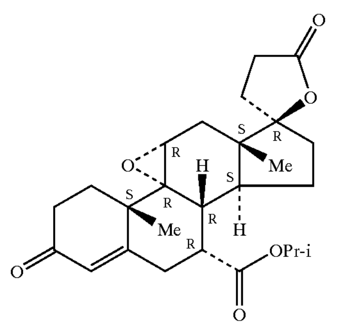 | Pregn-4-ene-7,21-dicarboxylic acid, 9,11-epoxy-17-hydroxy-3-oxo-,γ-lactone, 1-methylethyl ester, (7α,11α,17α)- |

Angiotensin II receptor antagonist compounds suitable for use in the combination therapy are described in Table II, below. Preferred compounds for use in the combination therapy may be generally characterized structurally as having two portions. A first portion constitutes a mono-aryl-alkyl moiety, or a bi-aryl-alkyl moiety, or a mono-heteroaryl-alkyl moiety, or a bi-heteroaryl-alkyl moiety. A second portion constitutes a heterocyclic moiety or an open chain hetero-atom-containing moiety.

Typically, the first-portion mono/bi-aryl/heteroaryl-alkyl moiety is attached to the second portion heterocyclic/open-chain moiety through the alkyl group of the mono/bi-aryl/hetercaryl-alkyl moiety to any substitutable position on the heterocyclic/open-chain moiety second portion. Suitable first-portion mono/bi-aryl/heteroaryl-alkyl moieties are defined by any of the various moieties listed under Formula I:

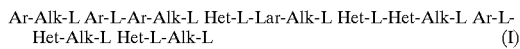

(I)

wherein the abbreviated notation used in the moieties of Formula I is defined as follows:

"Ar" means a five or six-membered carbocyclic ring system consisting of one ring or two fused rings, with such ring or rings being typically fully unsaturated but which also may be partially or fully saturated. "Phenyl" radical most typically exemplifies "Ar".

"Het" means a monocyclic or bicyclic fused ring system having from five to eleven ring members, and having at least one of such ring members being a hetero atom selected from oxygen, nitrogen and sulfur, and with such ring system containing up to six of such hetero atoms as ring members.

"Alk" means an alkyl radical or alkylene chain linear or branched, containing from one to about five carbon atoms. Typically, "Alk" means "methylene", i.e., —$CH_2$—.

"L" designates a single bond or a bivalent linker moiety selected from carbon, oxygen and sulfur. When "L" is carbon, such carbon has two hydrido atoms attached thereto.

Suitable second-portion heterocyclic moieties of the angiotensin II antagonist compounds, for use in the combination therapy, are defined by any of the various moieties listed under Formula IIa or IIb:

(IIa)

-continued

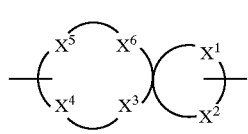
(IIb)

wherein each of $X^1$ through $X^6$ is selected from —CH=, —CH$_2$—, —N=, —NH—, O, and S, with the proviso that at least one of $X^1$ through $X^6$ in each of Formula IIa and Formula IIb must be a hetero atom. The heterocyclic moiety of Formula IIa or IIb may be attached through a bond from any ring member of the Formula IIa or IIb heterocyclic moiety having a substitutable or a bond-forming position.

Examples of monocyclic heterocyclic moieties of Formula IIa include thienyl, furyl, pyranyl, pyrrolyl, imidazolyl, triazolyl, pyrazolyl, pyridyl, pyrazinyl, pyrimidinyl, pyridazinyl, isothiazolyl, isoxazolyl, furazanyl, pyrrolidinyl, pyrrolinyl, furanyl, thiophenyl, isopyrrolyl, 3-isopyrrolyl, 2-isoimidazolyl, 1,2,3-triazolyl, 1,2,4-triazolyl, 1,2-dithiolyl, 1,3-dithiolyl, 1,2,3-oxathiolyl, oxazolyl, thiazolyl, 1,2,3-oxadiazolyl 1,2,4-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, 1,2-pyronyl, 1,4-pyronyl, pyridinyl, piperazinyl, s-triazinyl, as-triazinyl, v-triazinyl, 1,2,4-oxazinyl, 1,3,2-oxazinyl, 1,3,6-oxazinyl, 1,2,6-oxazinyl, 1,4-oxazinyl, o-isoxazinyl, p-isoxazinyl, 1,2,5-oxathiazinyl, 1,2,6-oxathiazinyl, 1,4,2-oxadiazinyl, 1,3,5,2-oxadiazinyl, morpholinyl, azepinyl, oxepinyl, thiepinyl and 1,2,4-diazepinyl.

Examples of bicyclic heterocyclic moieties of Formula IIb include benzo[b]thienyl, isobenzofuranyl, chromenyl, indolizinyl, isoindolyl, indolyl, indazolyl, purinyl, quinolizinyl, isoquinolyl, quinolyl, phthalazinyl, naphthyridinyl, quinoxalinyl, qinazolinyl, cinnolinyl, pteridinyl, isochromanyl, chromanyl, thieno[2,3-b]furanyl, 2H-furo[3,2-pyranyl, 5H-pyrido[2,3-d][1,2]oxazinyl, 1H-pyrazolo[4,3-d]oxazolyl, 4H-imidazo[4,5-d]thiazolyl, pyrazino[2,3-d]pyridazinyl, imidazo[2,1-b]thiazolyl, cyclopenta[b]pyranyl, 4H-[1,3]oxathiolo-[5,4-b]pyrrolyl, thieno[2,3-b]furanyl, imidazo[1,2-b][1,2,4]triazinyl and 4H-1,3-dioxolo[4,5-d]imidazolyl.

The angiotensin II receptor antagonist compounds, as provided by the first-and-second-portion moieties of Formula I and II, are further characterized by an acidic moiety attached to either of said first-and-second-portion moieties. Preferably this acidic moiety is attached to the first-portion moiety of Formula I and is defined by Formula III:

—U$_n$A  (III)

wherein n is a number selected from zero through three, inclusive, and wherein A is an acidic group selected to contain at least one acidic hydrogen atom, and the amide, ester and salt derivatives of said acidic moieties; wherein U is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms.

The phase "acidic group selected to contain at least one acidic hydrogen atom", as used to define the —U$_n$A moiety, is intended to embrace chemical groups which, when attached to any substitutable position of the Formula I–IIa/b moiety, confers acidic character to the compound of Formula I–IIa/b. "Acidic character" means proton-donor capability, that is, the capacity of the compound of Formula I–IIa/b to be a proton donor in the presence of a proton-receiving substance such as water. Typically, the acidic group should be selected to have proton-donor capability such that the product compound of Formula I–IIa/b has a pK$_a$ in a range from about one to about twelve. More typically, the Formula I–IIa/b compound would have a pK$_a$ in a range from about two about seven. An example of an acidic group containing at least one acidic hydrogen atom is carboxyl group (—COOH). Where n is zero and A is —COOH, in the —U$_n$A moiety, such carboxyl group would be attached directly to one of the Formula I–IIa/b positions. The Formula I–IIa/b compound may have one —U$_n$A moiety attached at one of the Formula I–IIa/b positions, or may have a plurality of such —U$_n$A moieties attached at more than one of the Formula I–IIa/b positions. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisoteres are described hereinafter. Compounds of Formula I–IIa/b may have one or more acidic protons and, therefore, may have one or more pK$_a$ values. It is preferred, however, that at least one of these pK$_a$ values of the Formula I–IIa/b compound as conferred by the —U$_n$A moiety be in a range from about two to about seven. The —U$_n$A moiety may be attached to one of the Formula I–IIa/b positions through any portion of the —U$_n$A moiety which results in a Formula I–IIa/b compound being relatively stable and also having a labile or acidic proton to meet the foregoing pK$_a$ criteria. For example, where the —U$_n$A acid moiety is tetrazole, the tetrazole is typically attached at the tetrazole ring carbon atoms.

For any of the moieties embraced by Formula I and Formula II, such moieties may be substituted at any substitutable position by one or more radicals selected from hydrido, hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

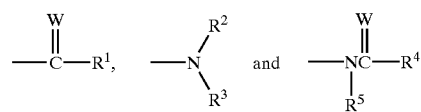

wherein W is oxygen atom or sulfur atom; wherein each of $R^1$ through $R^5$ is independently selected from hydrido, alkyl, cycloalkyl, cycloalkylalkyl, aralkyl, aryl, YR$^6$ and

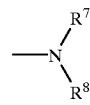

wherein Y is selected from oxygen atom and sulfur atom and $R^6$ is selected from hydro, alkyl, cycloalkyl, cycloalkylalkyl, aralkyl and aryl; wherein each of $R^1$, $R^2$, $R^3$, $R^4$, $R^5$, $R^7$ and $R^8$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^1$, $R^2$, $R^3$, $R^4$, $R^5$, $R^7$ and $R^8$ is further independently selected from amino and amido radicals of the formula

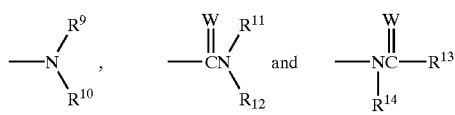

wherein W is oxygen atom or sulfur atom; wherein each of $R^9$, $R^{10}$, $R^{11}$, $R^{12}$, $R^{13}$ and $R^{14}$ is independently selected from hydrido, alkyl, cycloalkyl, cyano, hydroxyalkyl, cycloalkylalkyl, aloxyalkyl, haloalkylsulfinyl, haloalkylsulfonyl, aralkyl and aryl, and wherein each of $R^2$ and $R^3$ taken together and each of $R^4$ and $R^5$ taken together may form a heterocyclic group having five to seven ring members including the nitrogen atom of said amino or amido radical, which heterocyclic group may further contain one or more hetero atom as ring members selected from oxygen, nitrogen and sulfur atoms and which heterocyclic group may be saturated or partially unsaturated; wherein each of $R^2$ and $R^3$ taken together and each of $R^7$ and $R^8$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

The combination therapy of the invention would be useful in treating myocardial fibrosis or cardiac hypertrophy, particularly left ventricular hypertrophy. The combination therapy would also be useful with adjunctive therapies. For example, the combination therapy may be used in combination with other drugs, such as a diuretic, to aid in treatment of hypertension.

Table II, below, contains description of angiotensin II antagonist compounds which may be used in the combination therapy. Associated with each compound listed in Table II is a published patent document describing the chemical preparation of the angiotensin II antagonist compound as well as the biological properties of such compound. The content of each of these patent documents is incorporated herein by reference.

TABLE II

Angiotensin II Antagonists

| Compound # | Structure | Source |
|---|---|---|
| 1 | 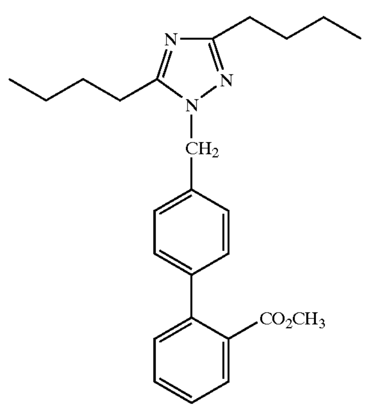 | WO #91/17148 pub. Nov. 14, 1991 |
| 2 | 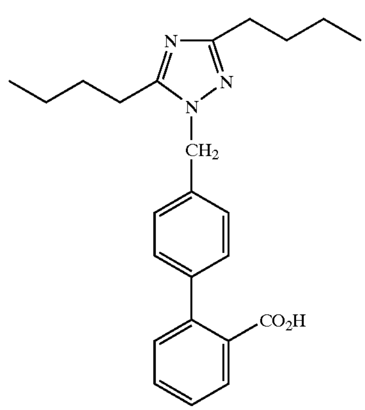 | WO #91/17148 pub. Nov. 14, 1991 |

TABLE II-continued
Angiotensin II Antagonists
| Compound # | Structure | Source |
|---|---|---|
| 3 | 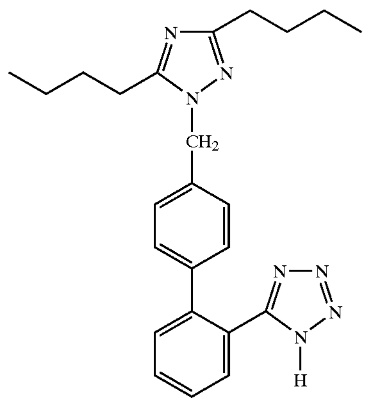 | WO #91/17148 pub. Nov. 14, 1991 |
| 4 | 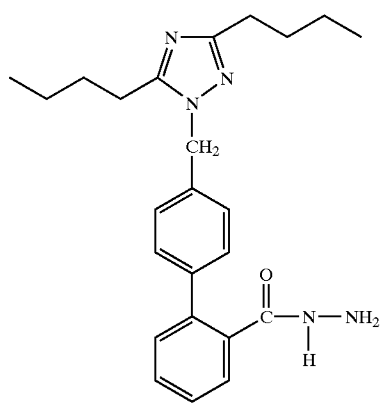 | WO #91/17148 pub. Nov. 14, 1991 |
| 5 | 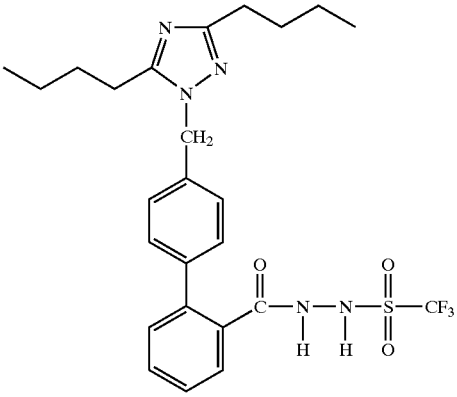 | WO #91/17148 pub. Nov. 14, 1991 |

TABLE II-continued

Angiotensin II Antagonists

| Compound # | Structure | Source |
|---|---|---|
| 6 | (5-butyl-3-chloro-1H-1,2,4-triazol-1-yl)methyl-biphenyl-2-carboxylic acid | WO #91/17148 pub. Nov. 14, 1991 |
| 7 | (5-butyl-3-chloro-1H-1,2,4-triazol-1-yl)methyl-biphenyl-2-yl-tetrazole | WO #91/17148 pub. Nov. 14, 1991 |
| 8 | (3-butyl-5-chloro-1H-1,2,4-triazol-1-yl)methyl-biphenyl-2-carboxylic acid | WO #91/17148 pub. Nov. 14, 1991 |

TABLE II-continued
Angiotensin II Antagonists
| Compound # | Structure | Source |
|---|---|---|
| 9 | 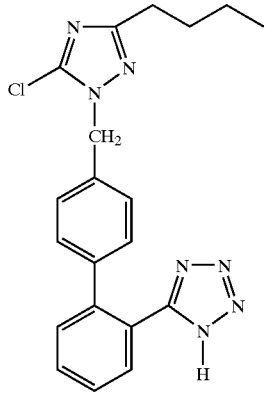 | WO #91/17148 pub. Nov. 14, 1991 |
| 10 | 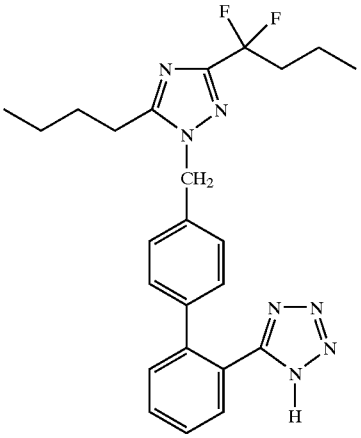 | WO #91/17148 pub. Nov. 14, 1991 |
| 11 | 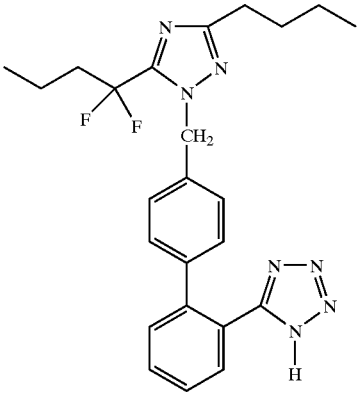 | WO #91/17148 pub. Nov. 14, 1991 |

TABLE II-continued
Angiotensin II Antagonists
| Compound # | Structure | Source |
|---|---|---|
| 12 | 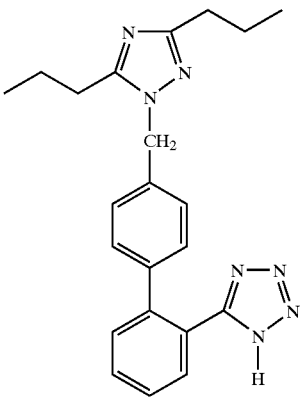 | WO #91/17148<br>pub. Nov. 14, 1991 |
| 13 | 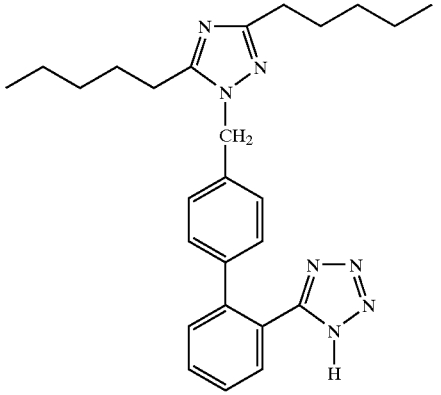 | WO #91/17148<br>pub. Nov. 14, 1991 |
| 14 | 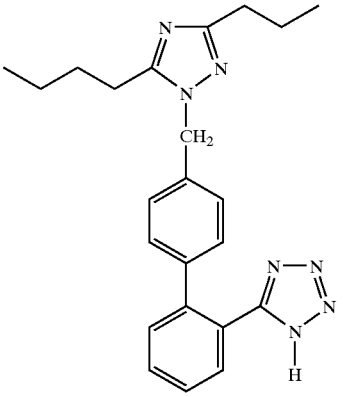 | WO #91/17148<br>pub. Nov. 14, 1991 |

TABLE II-continued

Angiotensin II Antagonists

| Compound # | Structure | Source |
|---|---|---|
| 15 | 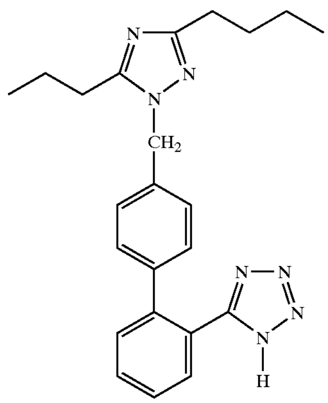 | WO #91/17148 pub. Nov. 14, 1991 |
| 16 | 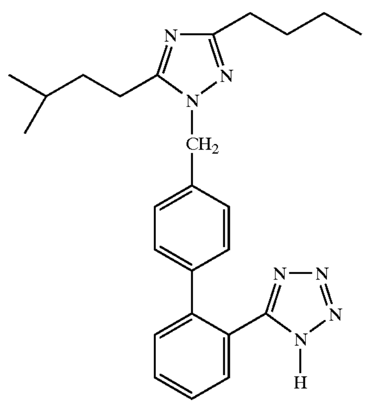 | WO #91/17148 pub. Nov. 14, 1991 |
| 17 | 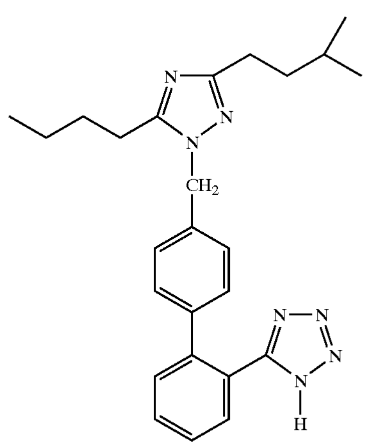 | WO #91/17148 pub. Nov. 14, 1991 |

TABLE II-continued

Angiotensin II Antagonists

| Compound # | Structure | Source |
|---|---|---|
| 18 | 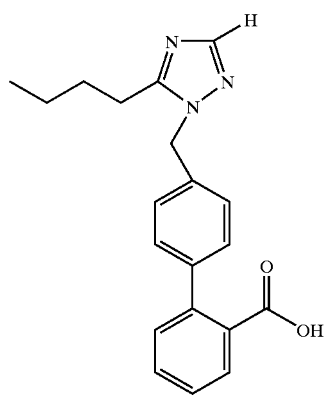 | WO #91/17148 pub. Nov. 14, 1991 |
| 19 | 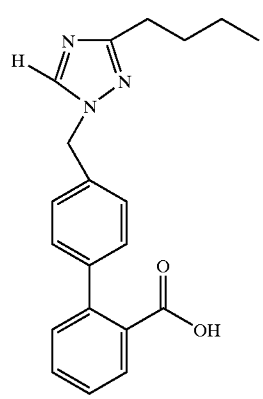 | WO #91/17148 pub. Nov. 14, 1991 |
| 20 | 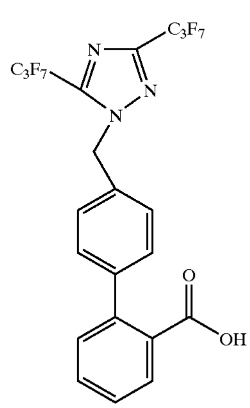 | WO #91/17148 pub. Nov. 14, 1991 |

TABLE II-continued
Angiotensin II Antagonists
| Compound # | Structure | Source |
|---|---|---|
| 21 | 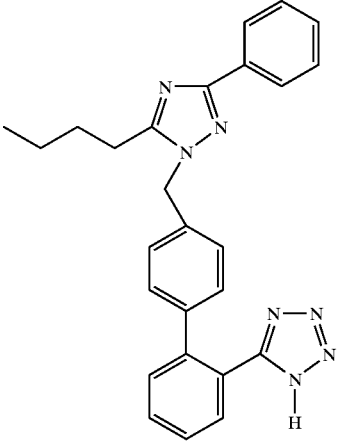 | WO #91/17148 pub. Nov. 14, 1991 |
| 22 | 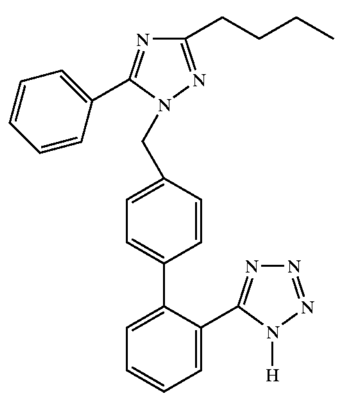 | WO #91/17148 pub. Nov. 14, 1991 |
| 23 | 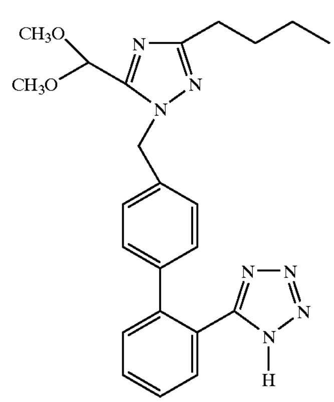 | WO #91/17148 pub. Nov. 14, 1991 |

TABLE II-continued

Angiotensin II Antagonists

| Compound # | Structure | Source |
|---|---|---|
| 24 | 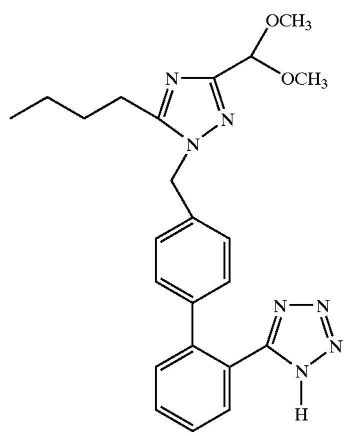 | WO #91/17148 pub. Nov. 14, 1991 |
| 25 | 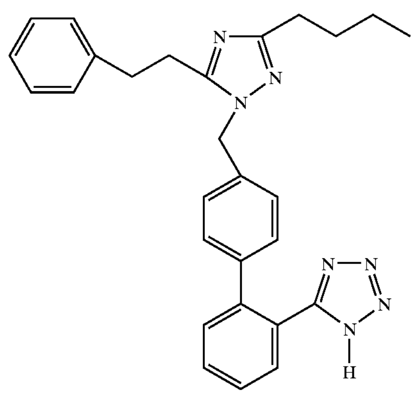 | WO #91/17148 pub. Nov. 14, 1991 |
| 26 | 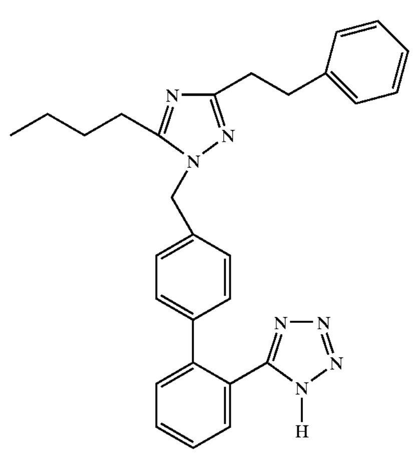 | WO #91/17148 pub. Nov. 14, 1991 |

TABLE II-continued

Angiotensin II Antagonists

| Compound # | Structure | Source |
|---|---|---|
| 27 | 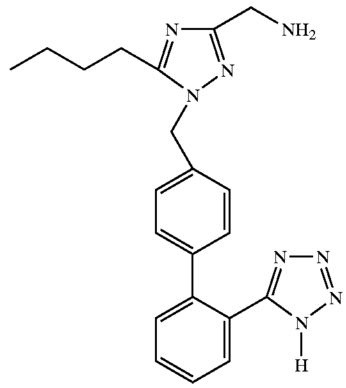 | WO #91/17148 pub. Nov. 14, 1991 |
| 28 | 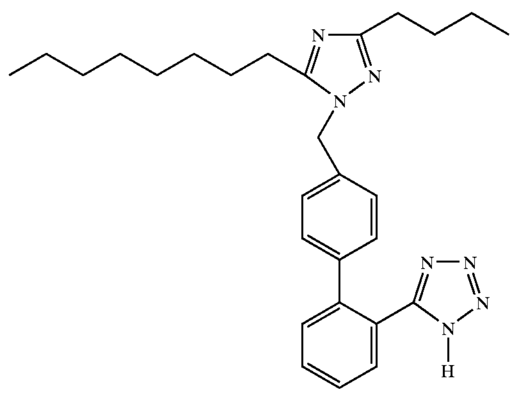 | WO #91/17148 pub. Nov. 14, 1991 |
| 29 | 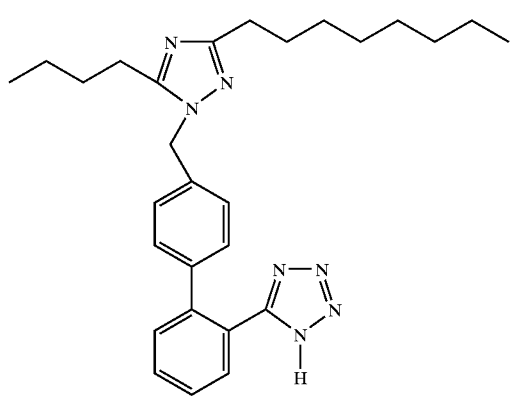 | WO #91/17148 pub. Nov. 14, 1991 |

TABLE II-continued

Angiotensin II Antagonists

| Compound # | Structure | Source |
|---|---|---|
| 30 | 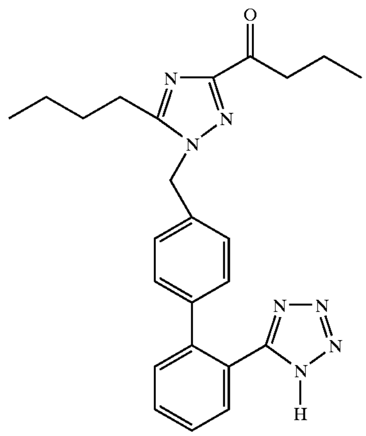 | WO #91/17148 pub. Nov. 14, 1991 |
| 31 | 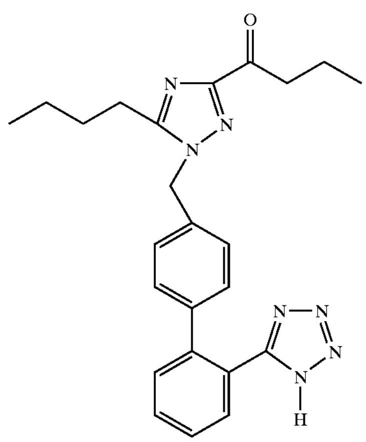 | WO #91/17148 pub. Nov. 14, 1991 |
| 32 | 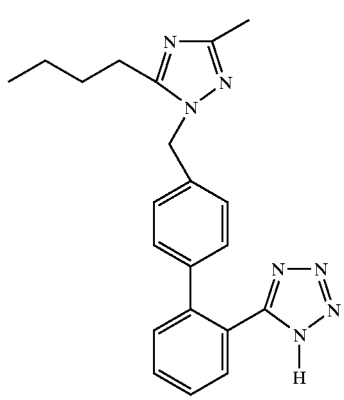 | WO #91/17148 pub. Nov. 14, 1991 |

TABLE II-continued
Angiotensin II Antagonists
| Compound # | Structure | Source |
|---|---|---|
| 33 | 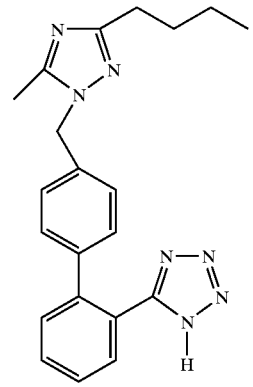 | WO #91/17148 pub. Nov. 14, 1991 |
| 34 | 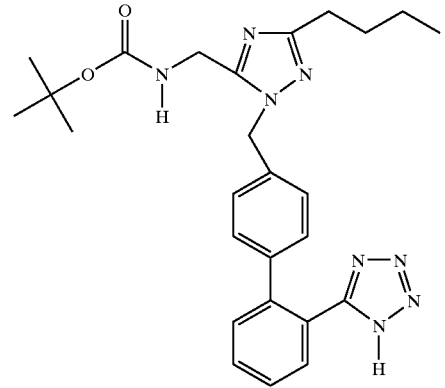 | WO #91/17148 pub. Nov. 14, 1991 |
| 35 | 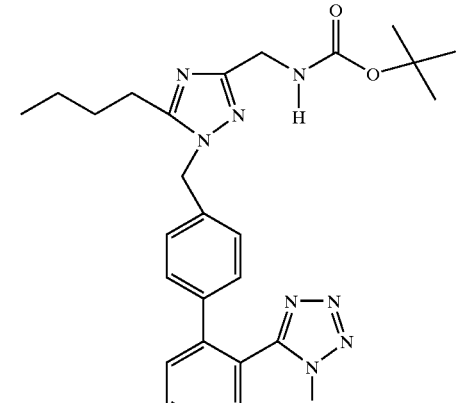 | WO #91/17148 pub. Nov. 14, 1991 |

TABLE II-continued

Angiotensin II Antagonists

| Compound # | Structure | Source |
|---|---|---|
| 36 | 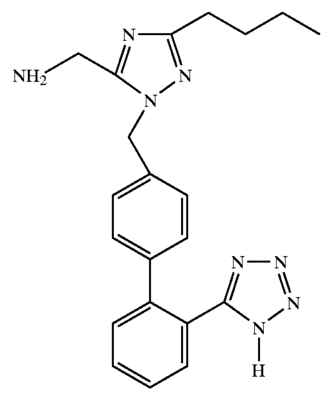 | WO #91/17148 pub. Nov. 14, 1991 |
| 37 | 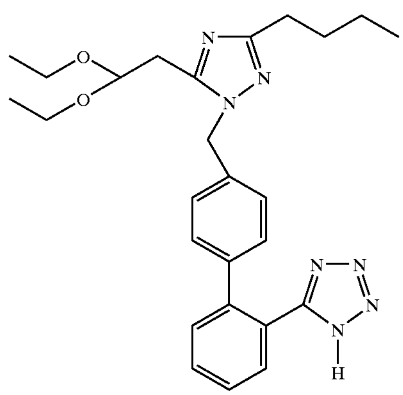 | WO #91/17148 pub. Nov. 14, 1991 |
| 38 | 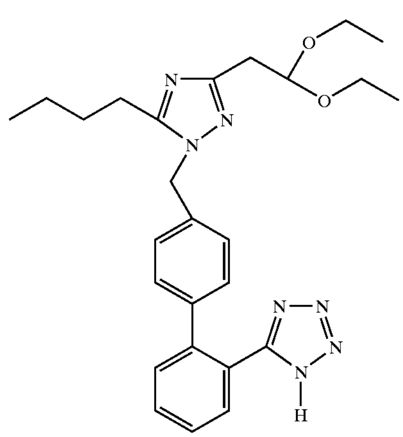 | WO #91/17148 pub. Nov. 14, 1991 |

TABLE II-continued

Angiotensin II Antagonists

| Compound # | Structure | Source |
|---|---|---|
| 39 | 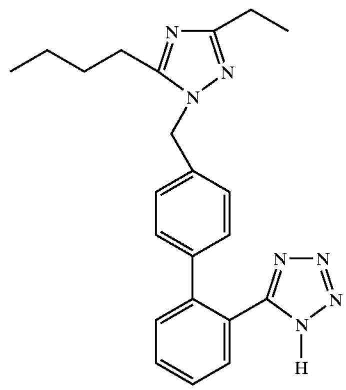 | WO #91/17148 pub. Nov. 14, 1991 |
| 40 | 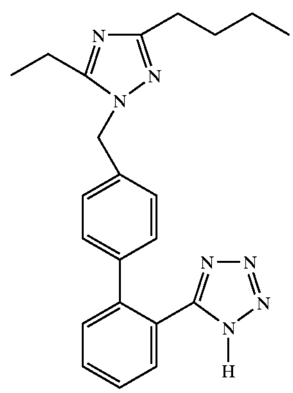 | WO #91/17148 pub. Nov. 14, 1991 |
| 41 | 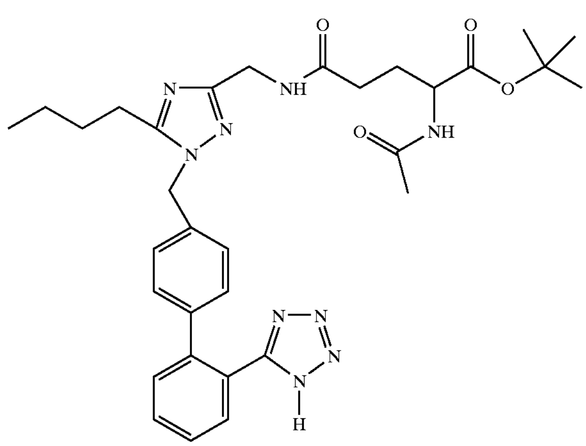 | WO #91/17148 pub. Nov. 14, 1991 |

TABLE II-continued
Angiotensin II Antagonists
| Compound # | Structure | Source |
|---|---|---|
| 42 | 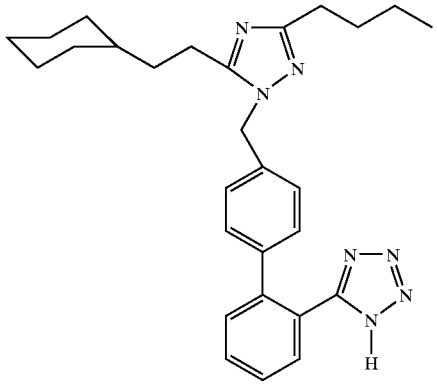 | WO #91/17148 pub. Nov. 14, 1991 |
| 43 | 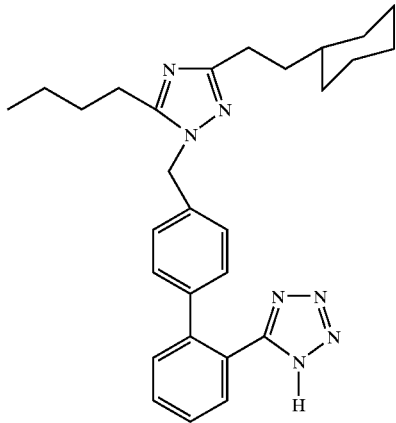 | WO #91/17148 pub. Nov. 14, 1991 |
| 44 | 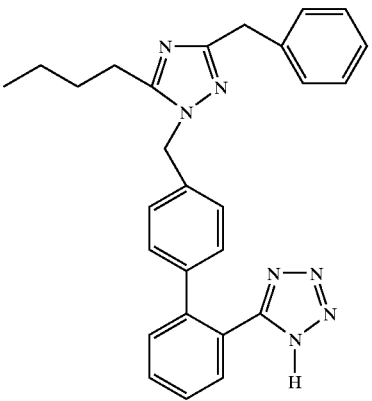 | WO #91/17148 pub. Nov. 14, 1991 |

TABLE II-continued
Angiotensin II Antagonists
| Compound # | Structure | Source |
|---|---|---|
| 45 | 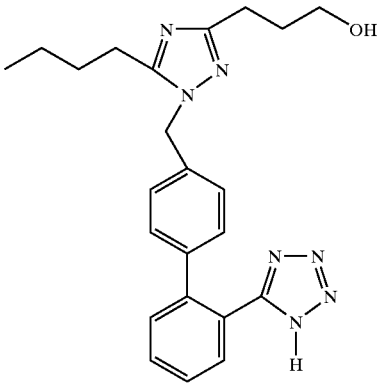 | WO #91/17148 pub. Nov. 14, 1991 |
| 46 | 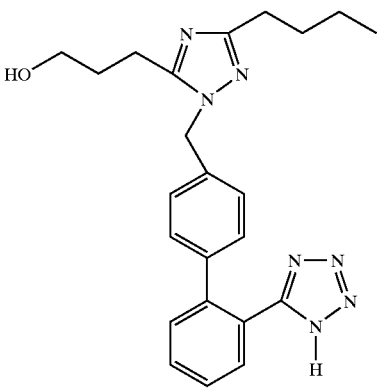 | WO #91/17148 pub. Nov. 14, 1991 |
| 47 | 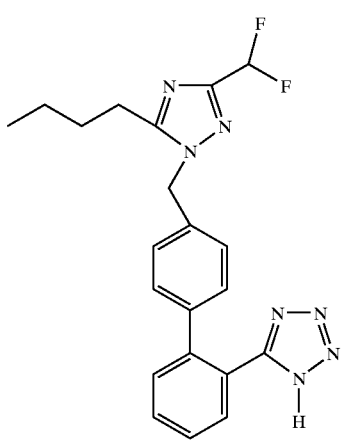 | WO #91/17148 pub. Nov. 14, 1991 |

TABLE II-continued

Angiotensin II Antagonists

| Compound # | Structure | Source |
|---|---|---|
| 48 | 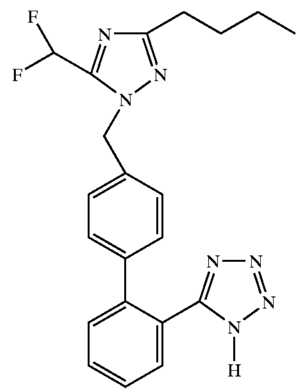 | WO #91/17148 pub. Nov. 14, 1991 |
| 49 | 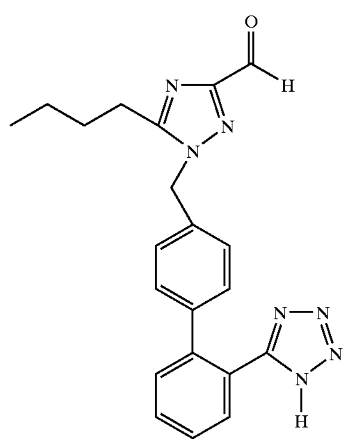 | WO #91/17148 pub. Nov. 14, 1991 |
| 50 | 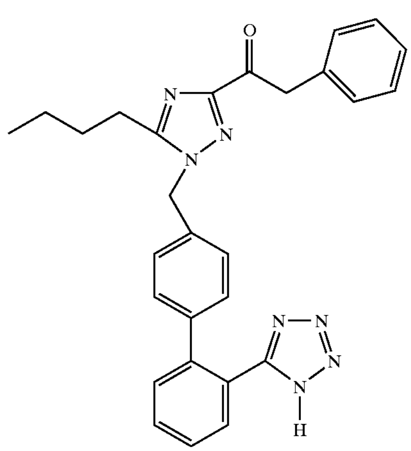 | WO #91/17148 pub. Nov. 14, 1991 |

TABLE II-continued

Angiotensin II Antagonists

| Compound # | Structure | Source |
|---|---|---|
| 51 | 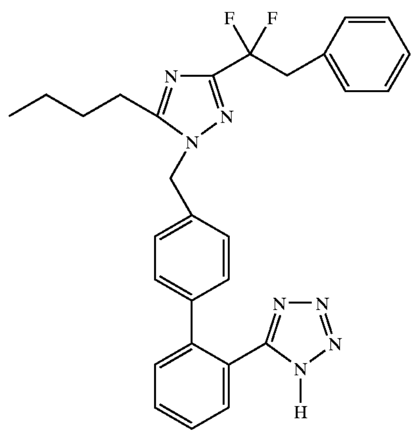 | WO #91/17148 pub. Nov. 14, 1991 |
| 52 | 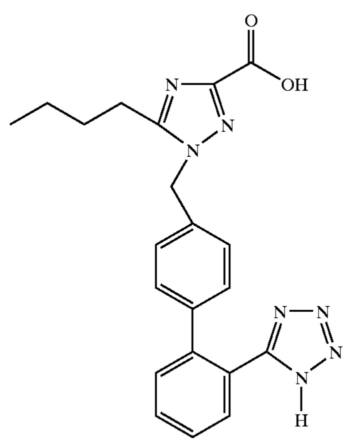 | WO #91/17148 pub. Nov. 14, 1991 |
| 53 | 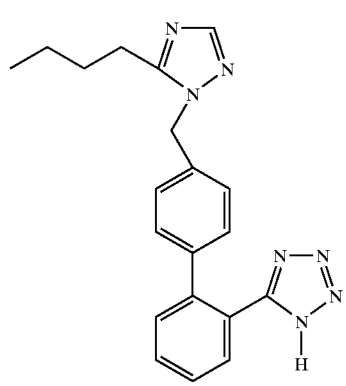 | WO #91/17148 pub. Nov. 14, 1991 |

TABLE II-continued
Angiotensin II Antagonists
| Compound # | Structure | Source |
|---|---|---|
| 54 | 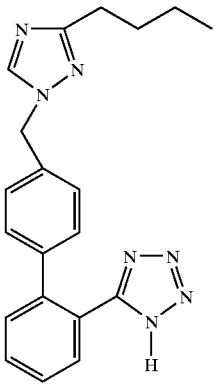 | WO #91/17148 pub. Nov. 14, 1991 |
| 55 | 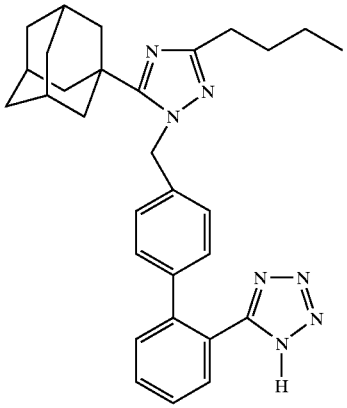 | WO #91/17148 pub. Nov. 14, 1991 |
| 56 | 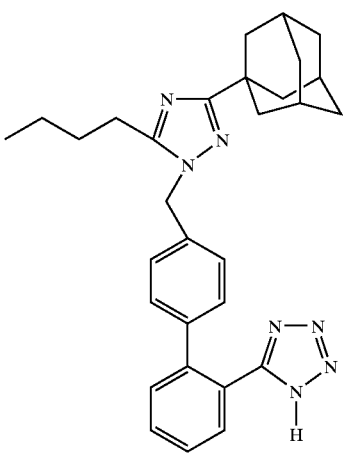 | WO #91/17148 pub. Nov. 14, 1991 |

TABLE II-continued

Angiotensin II Antagonists

| Compound # | Structure | Source |
|---|---|---|
| 57 | 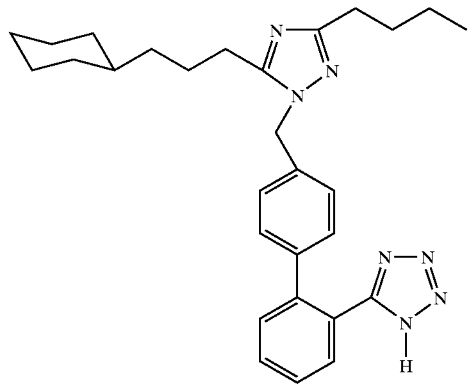 | WO #91/17148 pub. Nov. 14, 1991 |
| 58 | 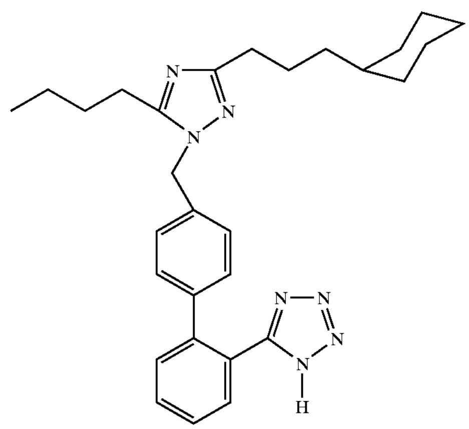 | WO #91/17148 pub. Nov. 14, 1991 |
| 59 | 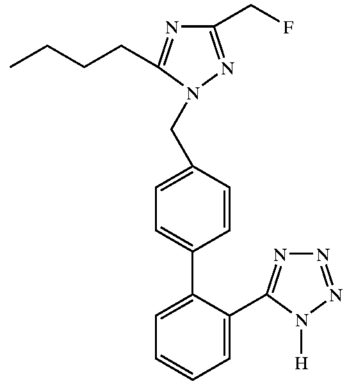 | WO #91/17148 pub. Nov. 14, 1991 |

TABLE II-continued
Angiotensin II Antagonists
| Compound # | Structure | Source |
|---|---|---|
| 60 | 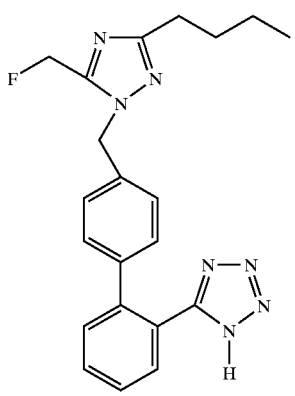 | WO #91/17148<br>pub. Nov. 14, 1991 |
| 61 | 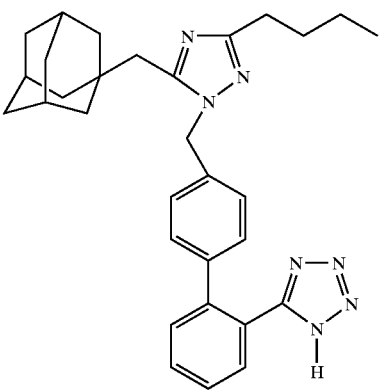 | WO #91/17148<br>pub. Nov. 14, 1991 |
| 62 | 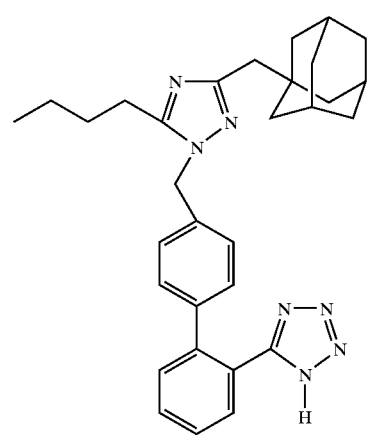 | WO #91/17148<br>pub. Nov. 14, 1991 |

TABLE II-continued

Angiotensin II Antagonists

| Compound # | Structure | Source |
|---|---|---|
| 63 | 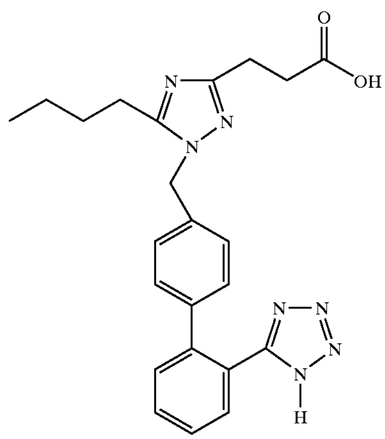 | WO #91/17148 pub. Nov. 14, 1991 |
| 64 | 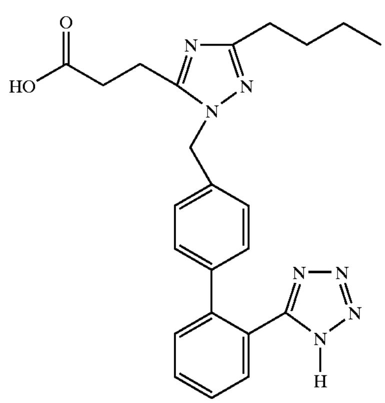 | WO #91/17148 pub. Nov. 14, 1991 |
| 65 | 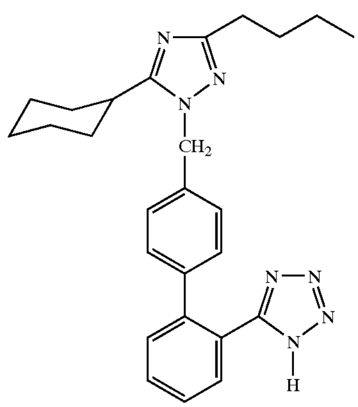 | WO #91/17148 pub. Nov. 14, 1991 |

TABLE II-continued
Angiotensin II Antagonists
| Compound # | Structure | Source |
|---|---|---|
| 66 | 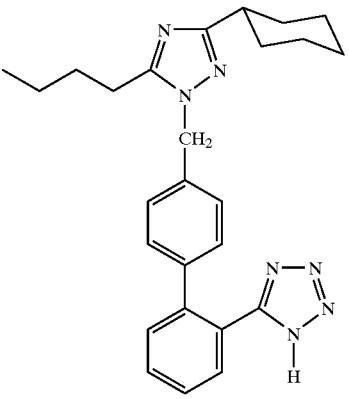 | WO #91/17148<br>pub. Nov. 14, 1991 |
| 67 | 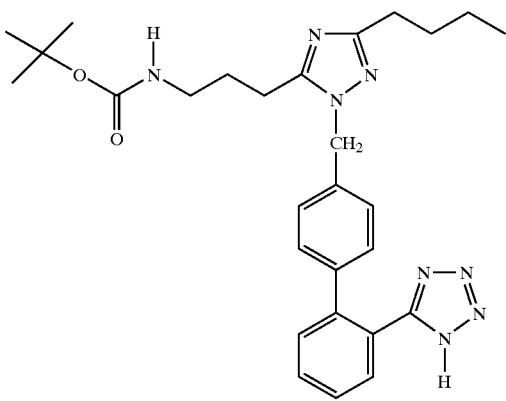 | WO #91/17148<br>pub. Nov. 14, 1991 |
| 68 | 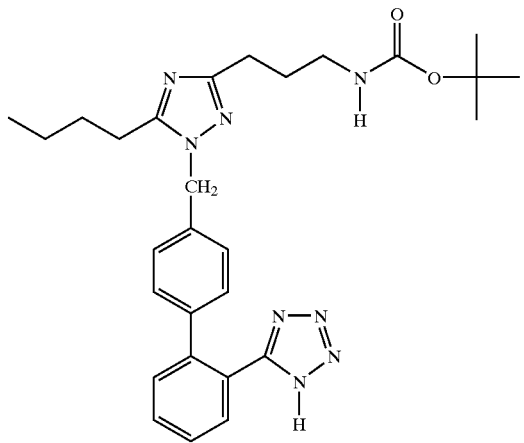 | WO #91/17148<br>pub. Nov. 14, 1991 |

TABLE II-continued
Angiotensin II Antagonists
| Compound # | Structure | Source |
|---|---|---|
| 69 | 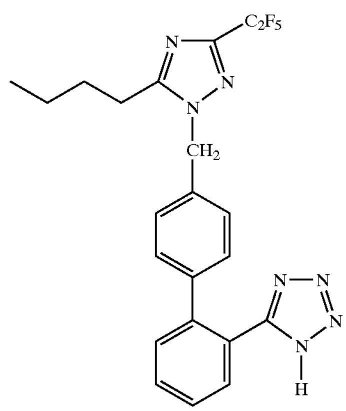 | WO #91/17148 pub. Nov. 14, 1991 |
| 70 | 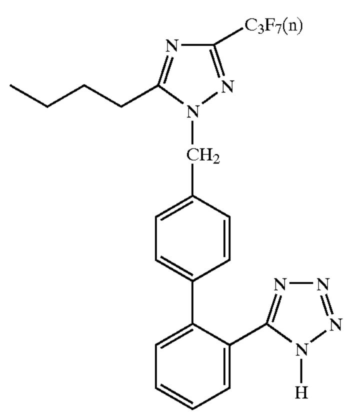 | WO #91/17148 pub. Nov. 14, 1991 |
| 71 | 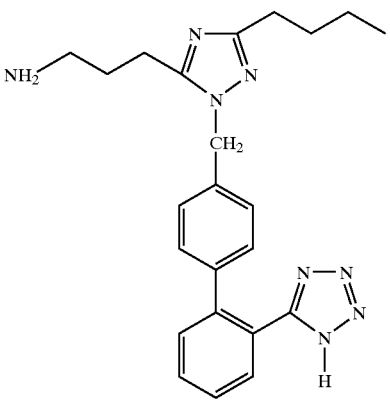 | WO #91/17148 pub. Nov. 14, 1991 |

TABLE II-continued
Angiotensin II Antagonists
| Compound # | Structure | Source |
|---|---|---|
| 72 | 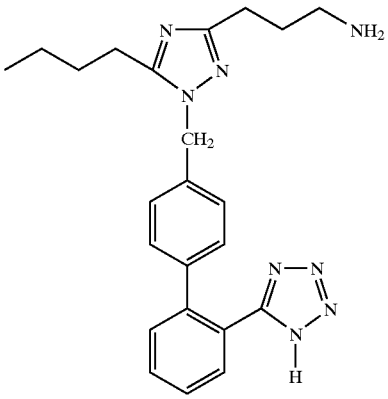 | WO #91/17148 pub. Nov. 14, 1991 |
| 73 | 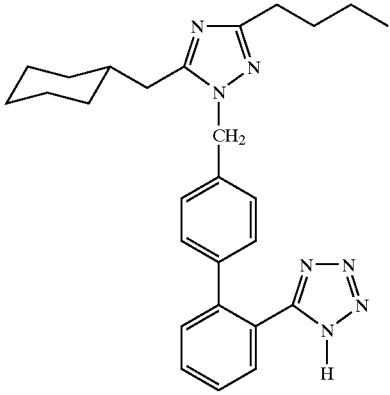 | WO #91/17148 pub. Nov. 14, 1991 |
| 74 | 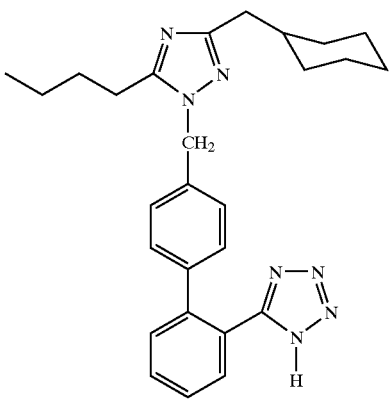 | WO #91/17148 pub. Nov. 14, 1991 |

TABLE II-continued

Angiotensin II Antagonists

| Compound # | Structure | Source |
|---|---|---|
| 75 | 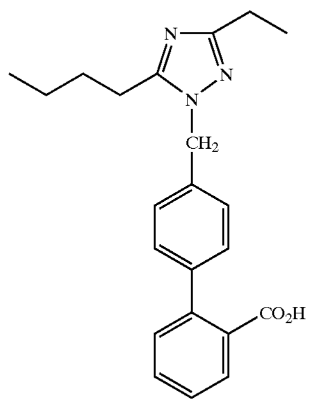 | WO #91/17148 pub. Nov. 14, 1991 |
| 76 | 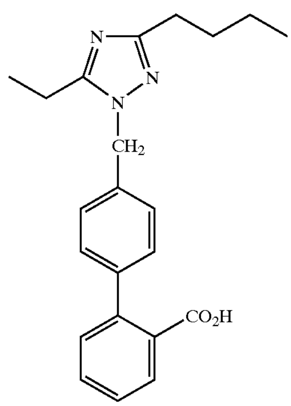 | WO #91/17148 pub. Nov. 14, 1991 |
| 77 | 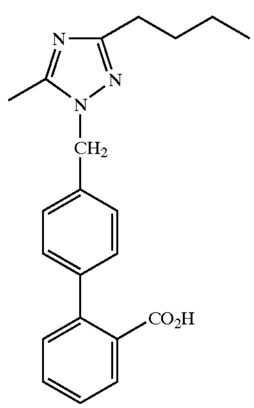 | WO #91/17148 pub. Nov. 14, 1991 |
| 78 | 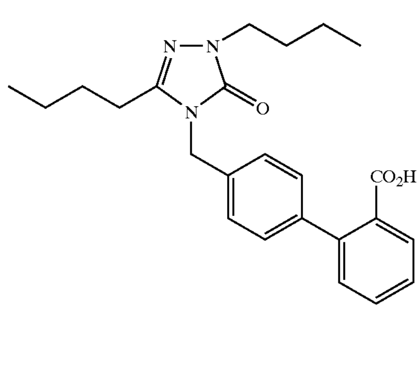 | WO #91/18888 pub. |

TABLE II-continued

Angiotensin II Antagonists

| Compound # | Structure | Source |
|---|---|---|
| 79 | 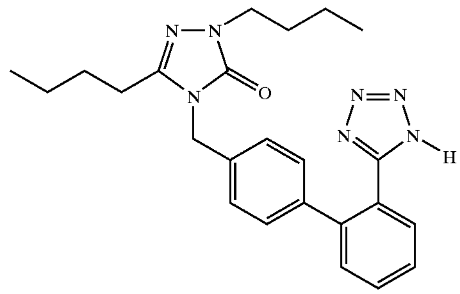 | WO #91/18888 pub. |
| 80 | 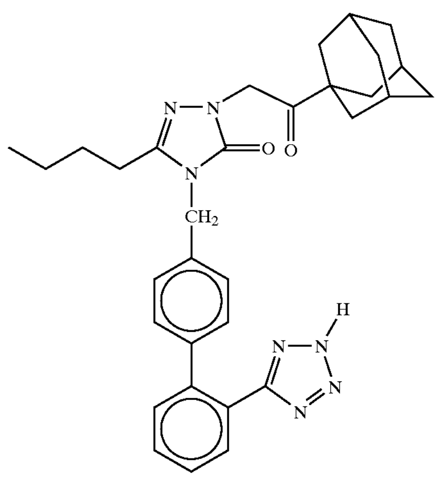 | WO #91/18888 pub. |
| 81 | 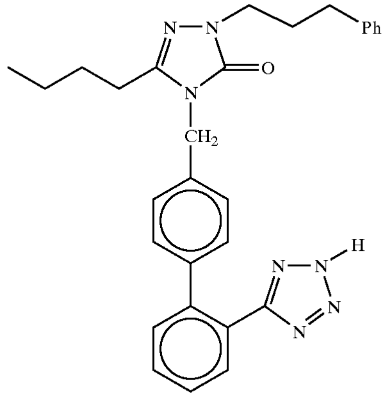 | WO #91/18888 pub. |

TABLE II-continued
Angiotensin II Antagonists
| Compound # | Structure | Source |
|---|---|---|
| 82 | 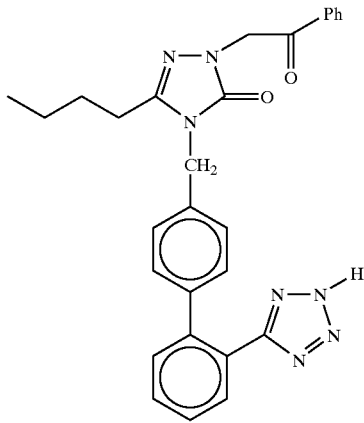 | WO #91/18888 pub. |
| 83 | 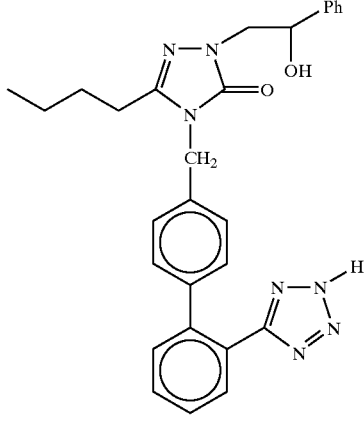 | WO #91/18888 pub. |
| 84 | 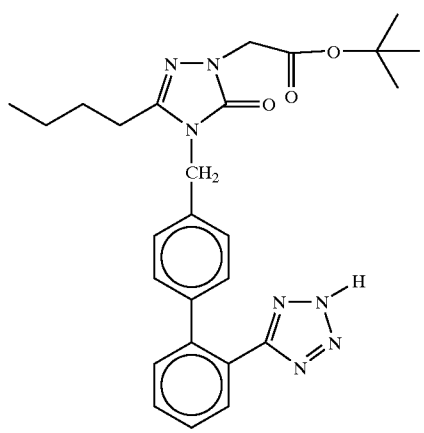 | WO #91/18888 pub. |

TABLE II-continued
Angiotensin II Antagonists
| Compound # | Structure | Source |
|---|---|---|
| 85 | 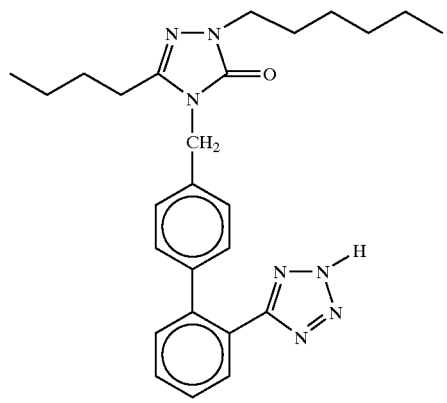 | WO #91/18888 pub. |
| 86 | 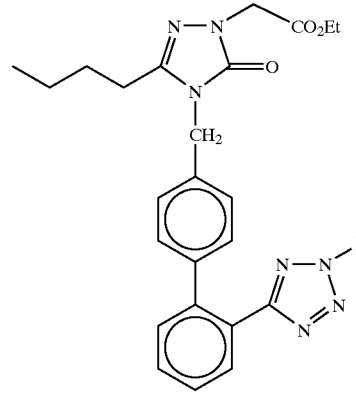 | WO #91/18888 pub. |
| 87 | 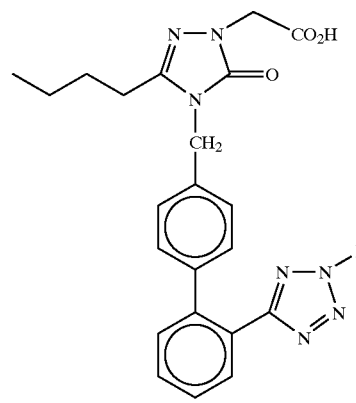 | WO #91/18888 pub. |

TABLE II-continued

Angiotensin II Antagonists

| Compound # | Structure | Source |
|---|---|---|
| 88 | 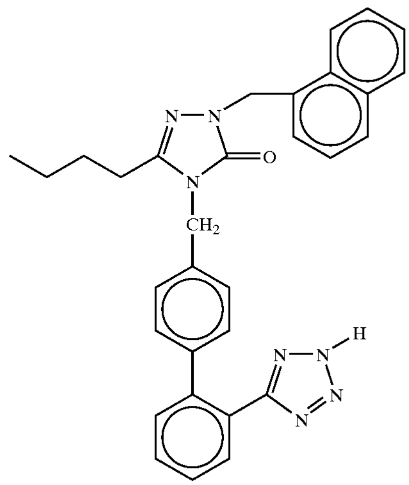 | WO #91/18888 pub. |
| 89 | 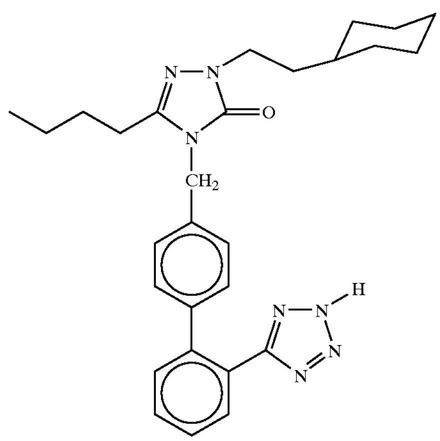 | WO #91/18888 pub. |
| 90 | 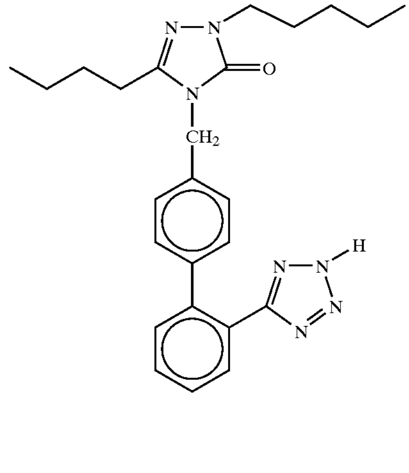 | WO #91/18888 pub. |

TABLE II-continued
Angiotensin II Antagonists
| Compound # | Structure | Source |
|---|---|---|
| 91 | 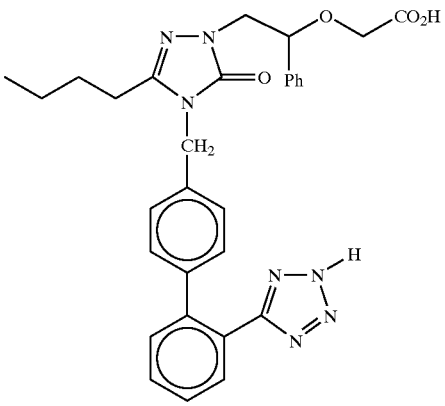 | WO #91/18888 pub. |
| 92 | 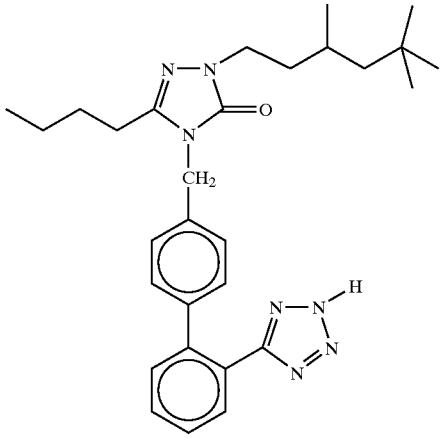 | WO #91/18888 pub. |
| 93 | 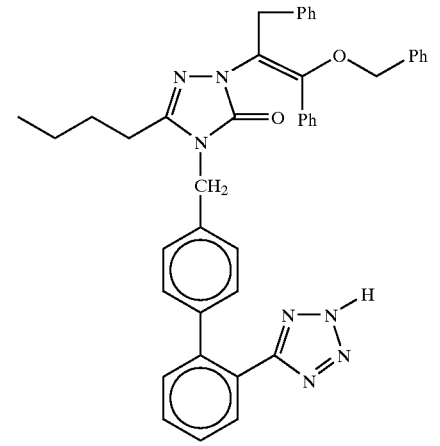 | WO #91/18888 pub. |

TABLE II-continued

Angiotensin II Antagonists

| Compound # | Structure | Source |
|---|---|---|
| 94 | 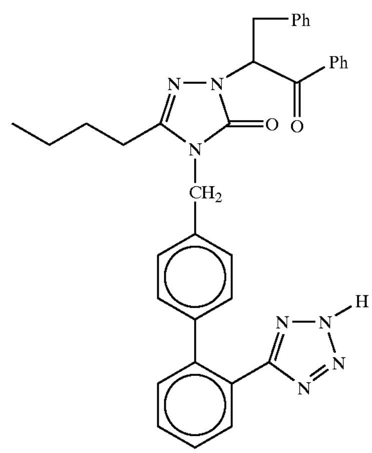 | WO #91/18888 pub. |
| 95 | 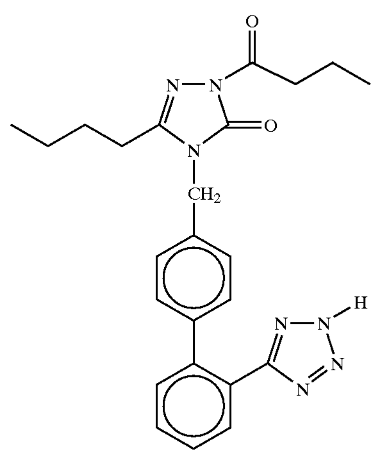 | WO #91/18888 pub. |
| 96 | 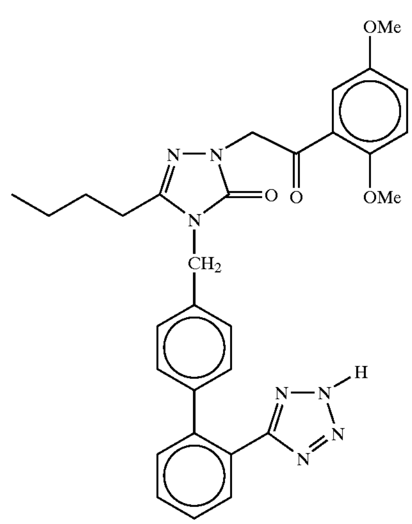 | WO #91/18888 pub. |

TABLE II-continued

Angiotensin II Antagonists

| Compound # | Structure | Source |
|---|---|---|
| 97 | | WO #91/18888 pub. |
| 98 | | WO #91/18888 pub. |
| 99 | | WO #91/18888 pub. |

TABLE II-continued

Angiotensin II Antagonists

| Compound # | Structure | Source |
|---|---|---|
| 100 | 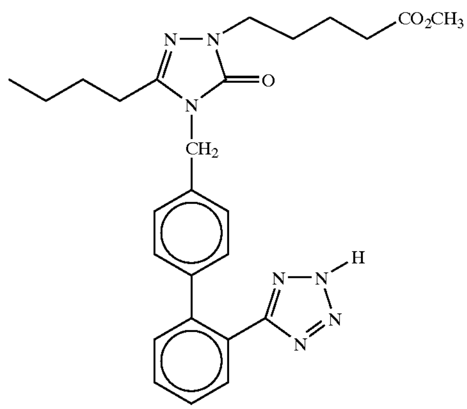 | WO #91/18888 pub. |
| 101 | 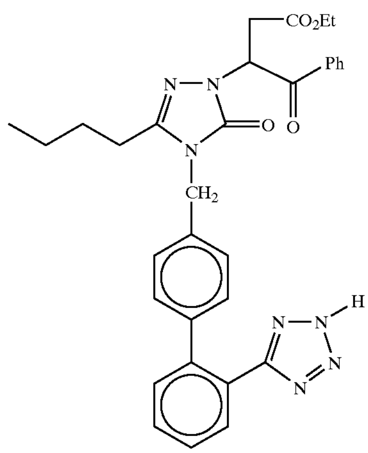 | WO #91/18888 pub. |
| 102 | 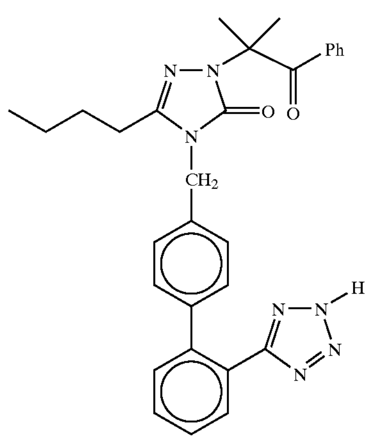 | WO #91/18888 pub. |

TABLE II-continued
Angiotensin II Antagonists
| Compound # | Structure | Source |
|---|---|---|
| 103 | 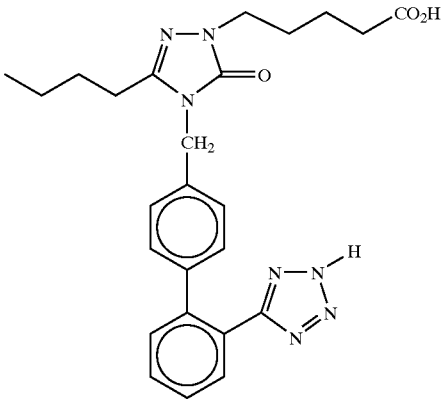 | WO #91/18888 pub. |
| 104 | 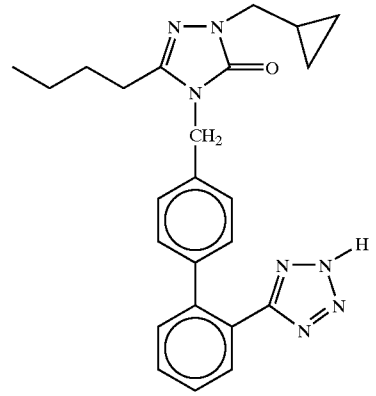 | WO #91/18888 pub. |
| 105 | 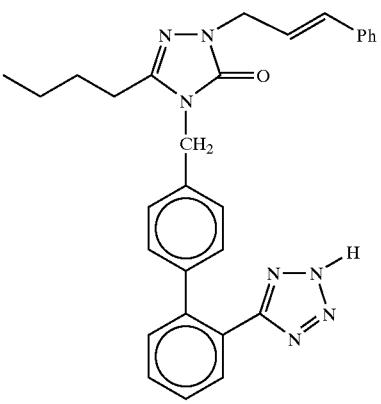 | WO #91/18888 pub. |

TABLE II-continued

Angiotensin II Antagonists

| Compound # | Structure | Source |
|---|---|---|
| 106 | 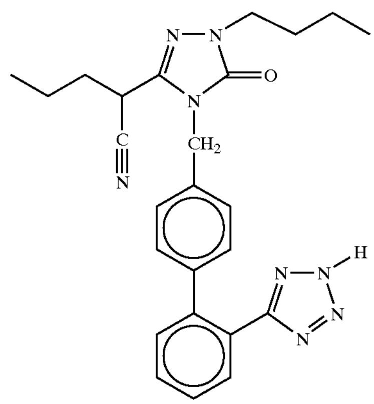 | WO #91/18888 pub. |
| 107 | 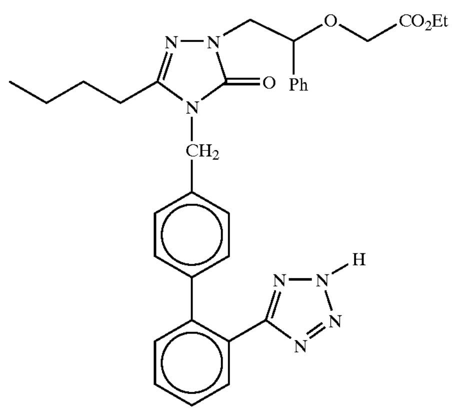 | WO #91/18888 pub. |
| 108 | 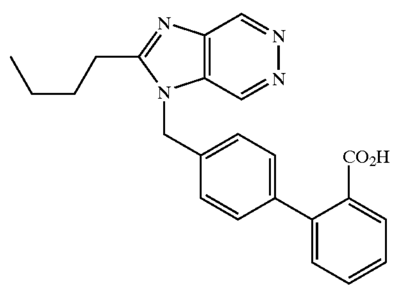 | WO #91/19715 pub. Dec. 26, 1991 |
| 109 | 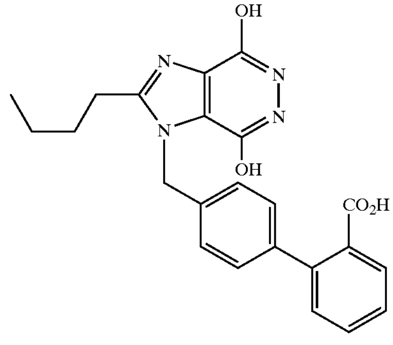 | WO #91/19715 pub. Dec. 26, 1991 |

TABLE II-continued

Angiotensin II Antagonists

| Compound # | Structure | Source |
|---|---|---|
| 110 | 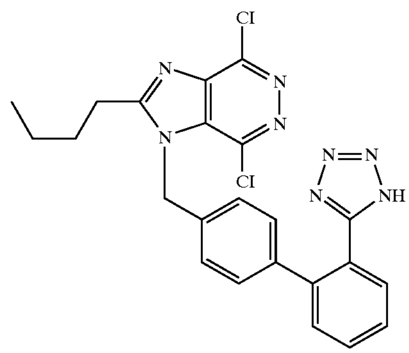 | WO #91/19715 pub. Dec. 26, 1991 |
| 111 | 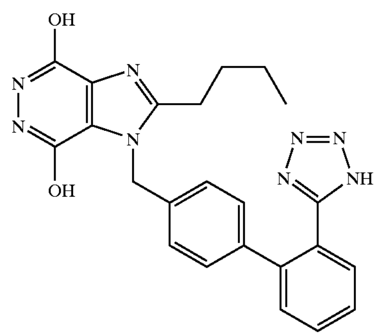 | WO #91/19715 pub. Dec. 26, 1991 |
| 112 | 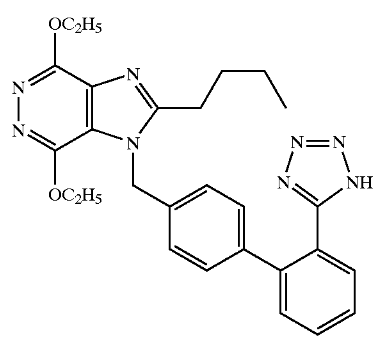 | WO #91/19715 pub. Dec. 26, 1991 |
| 113 | 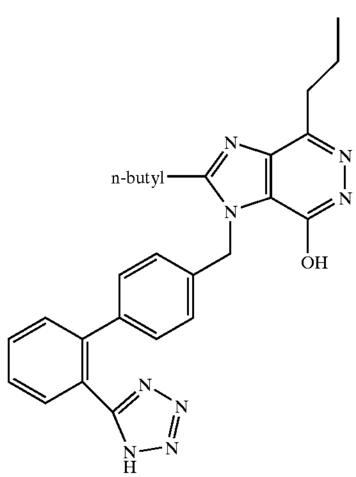 | WO #91/19715 pub. Dec. 26, 1991 |

TABLE II-continued
Angiotensin II Antagonists
| Compound # | Structure | Source |
|---|---|---|
| 114 | 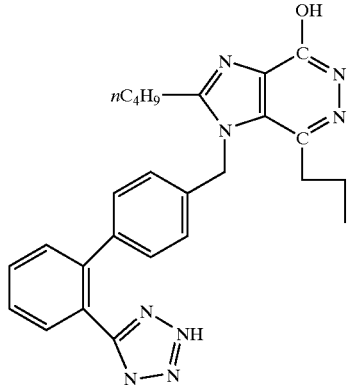 | WO #91/19715<br>pub. Dec. 26, 1991 |
| 115 | 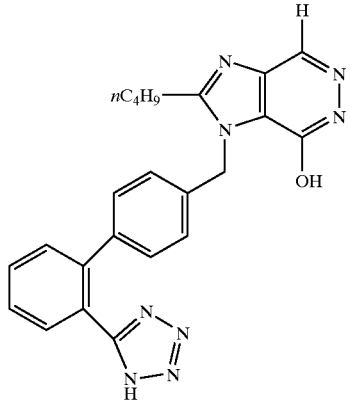 | WO #91/19715<br>pub. Dec. 26, 1991 |
| 116 | 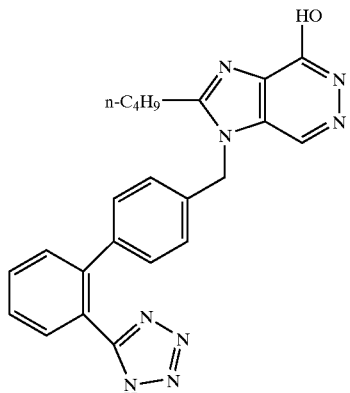 | WO #91/19715<br>pub. Dec. 26, 1991 |

TABLE II-continued
Angiotensin II Antagonists
| Compound # | Structure | Source |
|---|---|---|
| 117 | 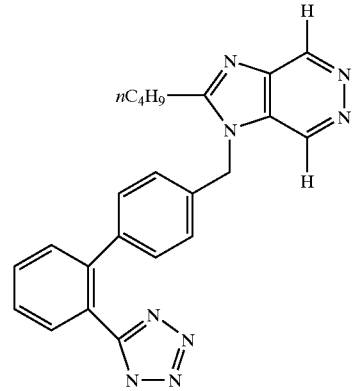 | WO #91/19715 pub. Dec. 26, 1991 |
| 118 | 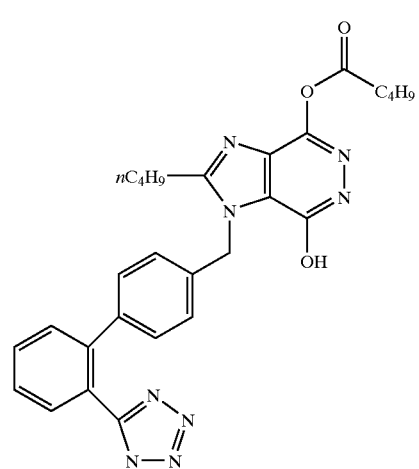 | WO #91/19715 pub. Dec. 26, 1991 |
| 119 | 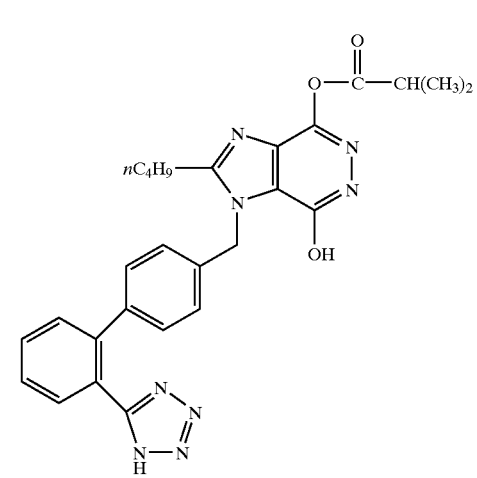 | WO #91/19715 pub. Dec. 26, 1991 |

TABLE II-continued
Angiotensin II Antagonists
| Compound # | Structure | Source |
|---|---|---|
| 120 | 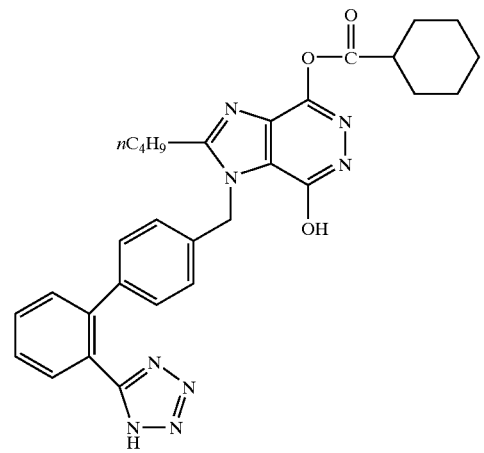 | WO #91/19715 pub. Dec. 26, 1991 |
| 121 | 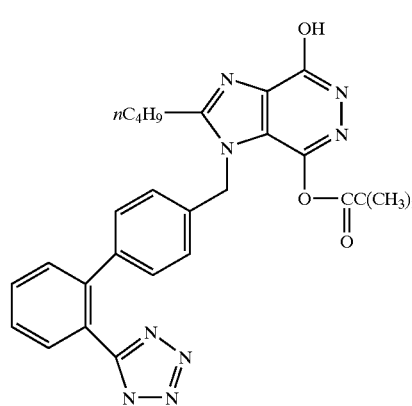 | WO #91/19715 pub. Dec. 26, 1991 |
| 122 | 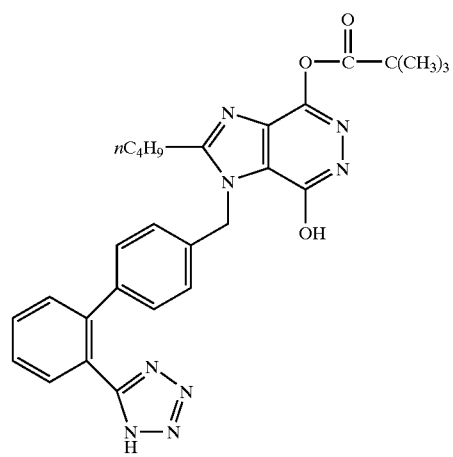 | WO #91/19715 pub. Dec. 26, 1991 |

TABLE II-continued
Angiotensin II Antagonists
| Compound # | Structure | Source |
|---|---|---|
| 123 | 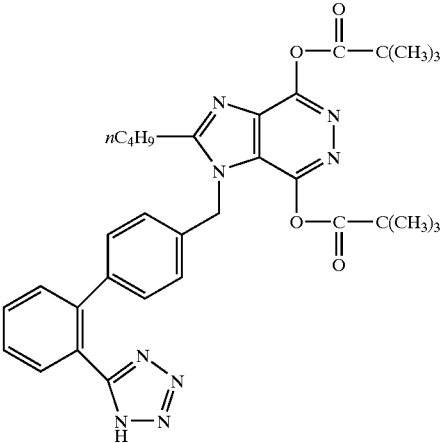 | WO #91/19715 pub. Dec. 26, 1991 |
| 124 | 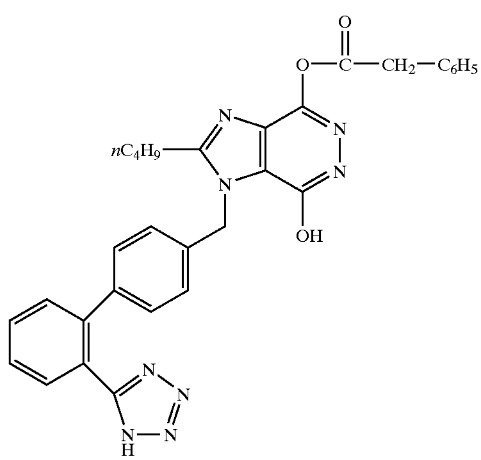 | WO #91/19715 pub. Dec. 26, 1991 |
| 125 | 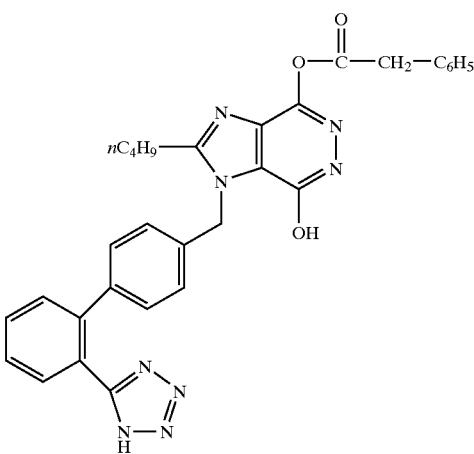 | WO #91/19715 pub. Dec. 26, 1991 |

TABLE II-continued
Angiotensin II Antagonists
| Compound # | Structure | Source |
|---|---|---|
| 126 | 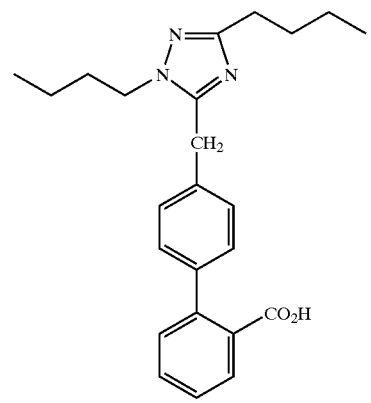 | WO #92/05161 pub. Apr. 2, 1992 |
| 127 | 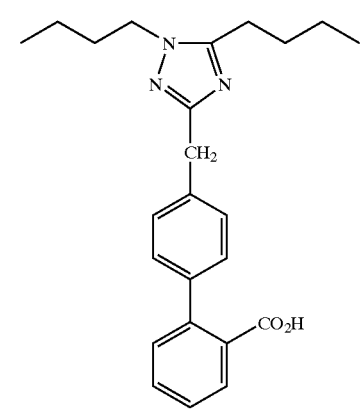 | WO #92/05161 pub. Apr. 2, 1992 |
| 128 | 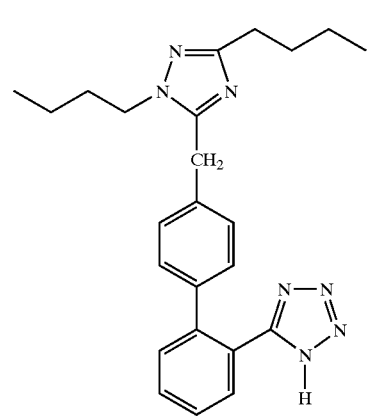 | WO #92/05161 pub. Apr. 2, 1992 |

TABLE II-continued

Angiotensin II Antagonists

| Compound # | Structure | Source |
|---|---|---|
| 129 | 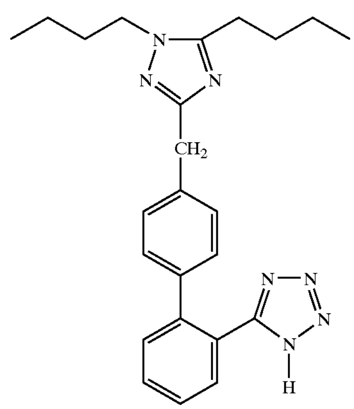 | WO #92/05161 pub. Apr. 2, 1992 |
| 130 | 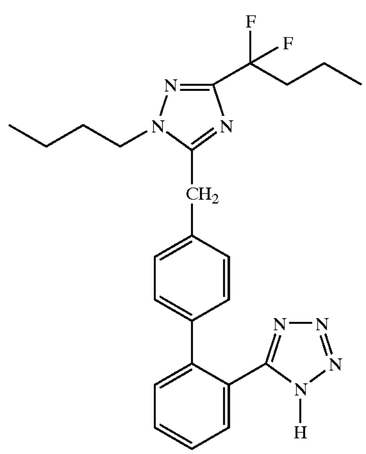 | WO #92/05161 pub. Apr. 2, 1992 |
| 131 | 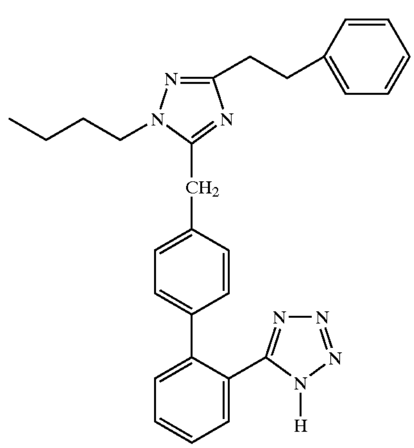 | WO #92/05161 pub. Apr. 2, 1992 |

TABLE II-continued
Angiotensin II Antagonists
| Compound # | Structure | Source |
|---|---|---|
| 132 | 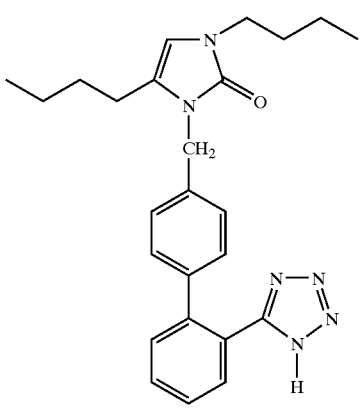 | WO #92/07834 pub. May 14, 1992 |
| 133 | 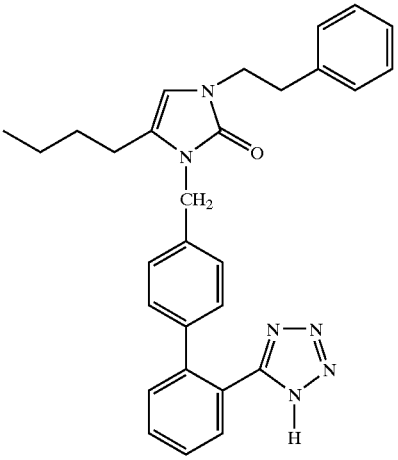 | WO #92/07834 pub. May 14, 1992 |
| 134 | 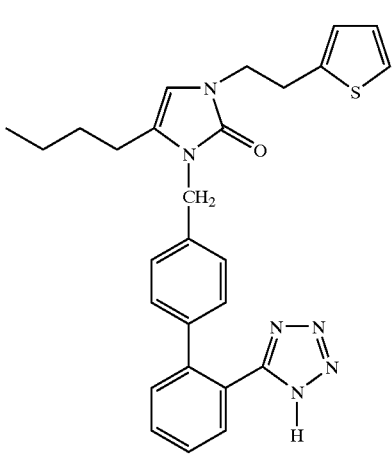 | WO #92/07834 pub. May 14, 1992 |

TABLE II-continued
Angiotensin II Antagonists
| Compound # | Structure | Source |
|---|---|---|
| 135 | 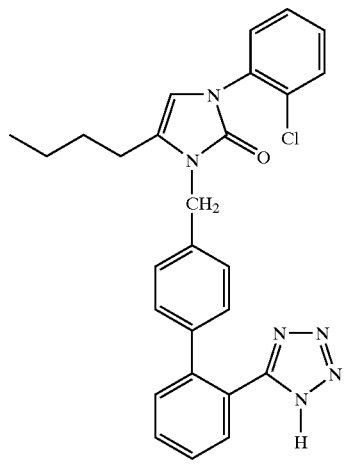 | WO #92/07834 pub. May 14, 1992 |
| 136 | 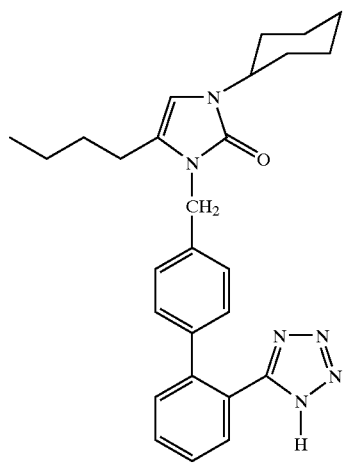 | WO #92/07834 pub. May 14, 1992 |
| 137 | 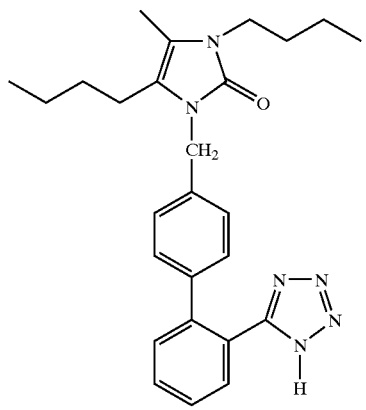 | WO #92/07834 pub. May 14, 1992 |

TABLE II-continued

Angiotensin II Antagonists

| Compound # | Structure | Source |
|---|---|---|
| 138 | 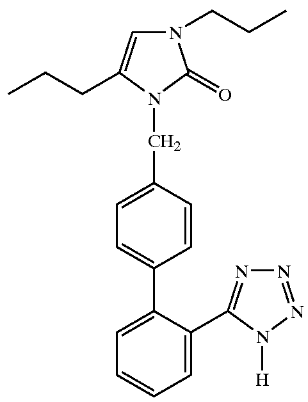 | WO #92/07834 pub. May 14, 1992 |
| 139 | 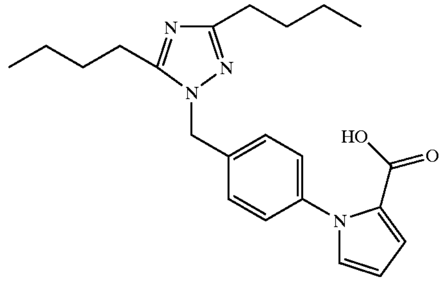 | WO #92/11255 pub. Jul. 9, 1992 |
| 140 | 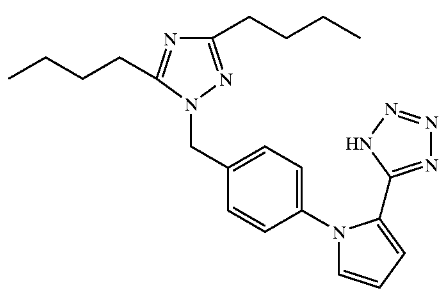 | WO #92/11255 pub. Jul. 9, 1992 |
| 141 | 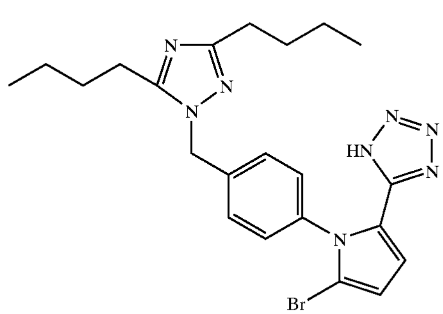 | WO #92/11255 pub. Jul. 9, 19921 |

TABLE II-continued

Angiotensin II Antagonists

| Compound # | Structure | Source |
|---|---|---|
| 142 | 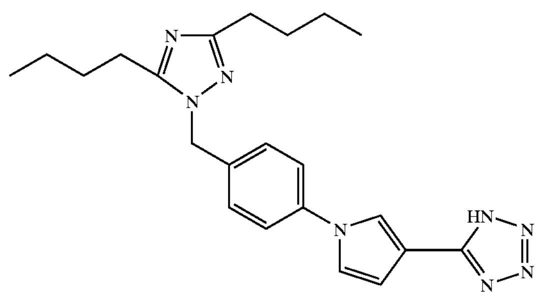 | WO #92/11255 pub. Jul. 9, 1992 |
| 143 | 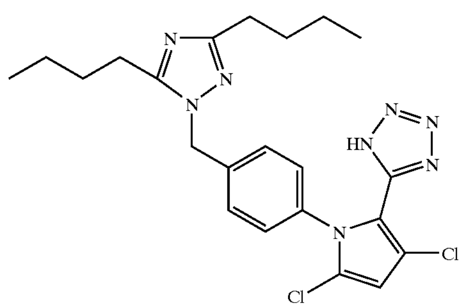 | WO #92/11255 pub. Jul. 9, 1992 |
| 144 | 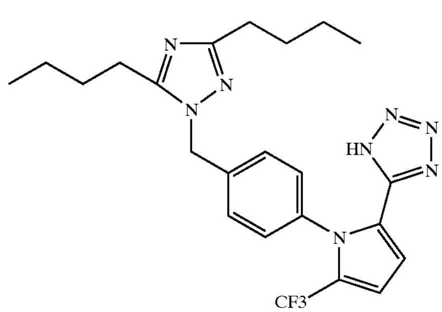 | WO #92/11255 pub. Jul. 9, 1992 |
| 145 | 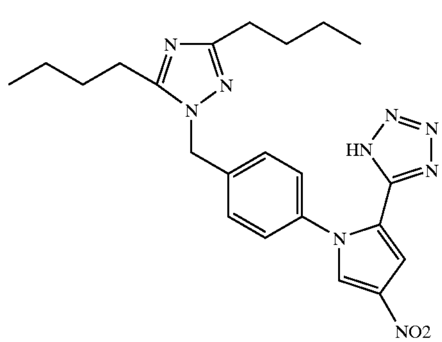 | WO #92/11255 pub. Jul. 9, 1992 |

TABLE II-continued

Angiotensin II Antagonists

| Compound # | Structure | Source |
|---|---|---|
| 146 | 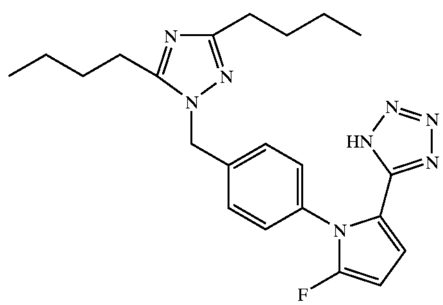 | WO #92/11255 pub. Jul. 9, 1992 |
| 147 | 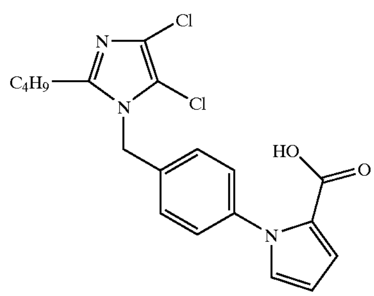 | WO #92/15577 pub. Sep. 17, 1992 |
| 148 | 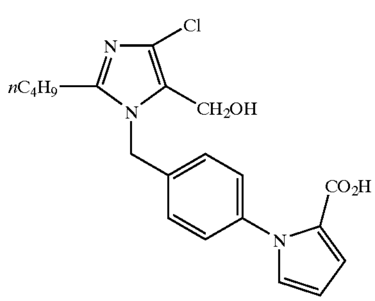 | WO #92/15577 pub. Sep. 17, 1992 |
| 149 | 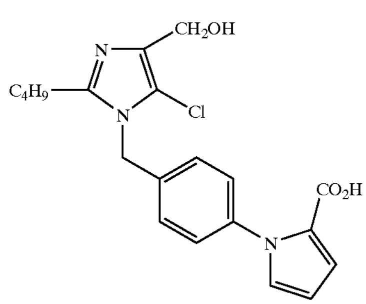 | WO #92/15577 pub. Sep. 17, 1992 |

TABLE II-continued

Angiotensin II Antagonists

| Compound # | Structure | Source |
|---|---|---|
| 150 | | WO #92/16523 pub. Oct. 1, 1992 |
| 151 | | WO #92/16523 pub. Oct. 1, 1992 |
| 152 | | WO #92/16523 pub. Oct. 1, 1992 |

TABLE II-continued

Angiotensin II Antagonists

| Compound # | Structure | Source |
|---|---|---|
| 153 | 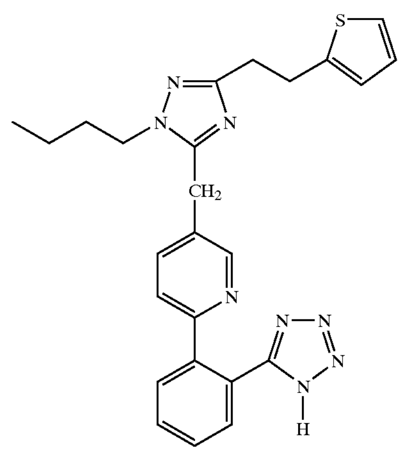 | WO #92/16523 pub. Oct. 1, 1992 |
| 154 | 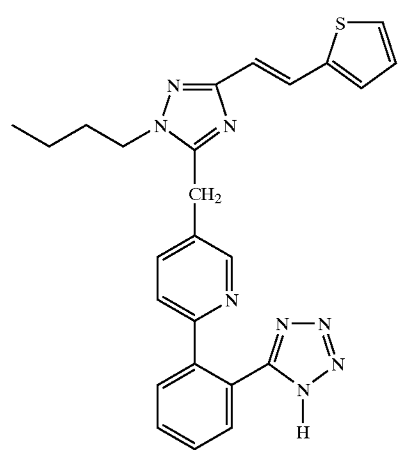 | WO #92/16523 pub. Oct. 1, 1992 |
| 155 | 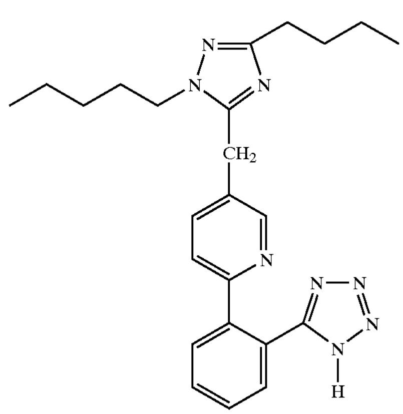 | WO #92/16523 pub. Oct. 1, 1992 |

TABLE II-continued

Angiotensin II Antagonists

| Compound # | Structure | Source |
|---|---|---|
| 156 | 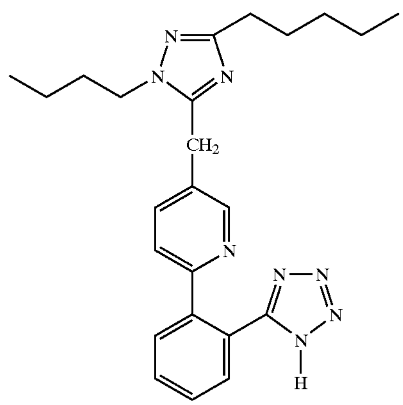 | WO #92/16523 pub. Oct. 1, 1992 |
| 157 | 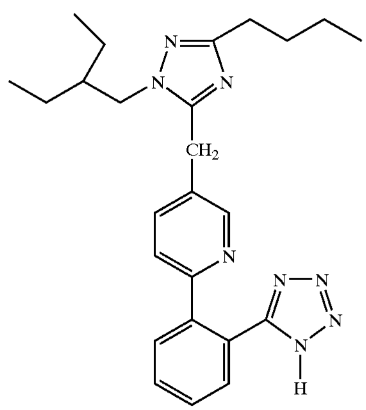 | WO #92/16523 pub. Oct. 1, 1992 |
| 158 | 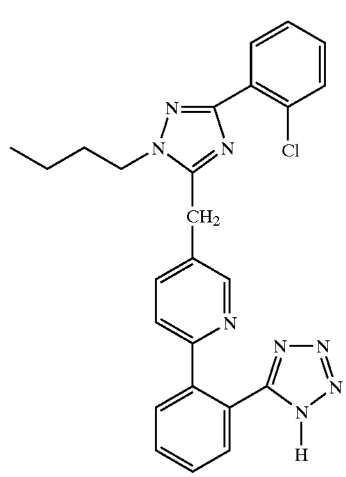 | WO #92/16523 pub. Oct. 1, 1992 |

TABLE II-continued

Angiotensin II Antagonists

| Compound # | Structure | Source |
|---|---|---|
| 159 | 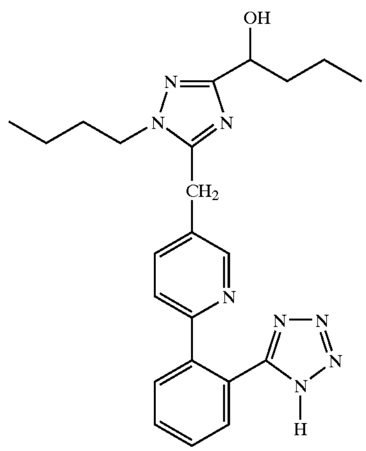 | WO #92/16523 pub. Oct. 1, 1992 |
| 160 | 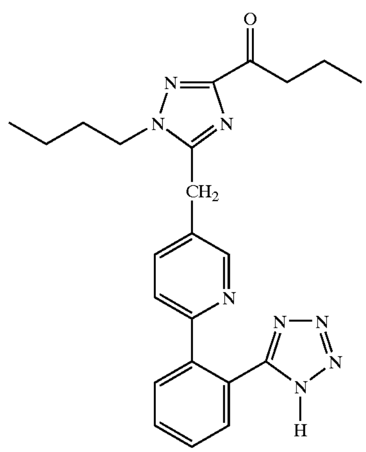 | WO #92/16523 pub. Oct. 1, 1992 |
| 161 | 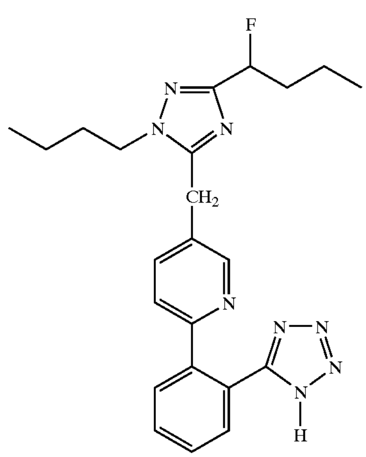 | WO #92/16523 pub. Oct. 1, 1992 |

TABLE II-continued

Angiotensin II Antagonists

| Compound # | Structure | Source |
|---|---|---|
| 162 | 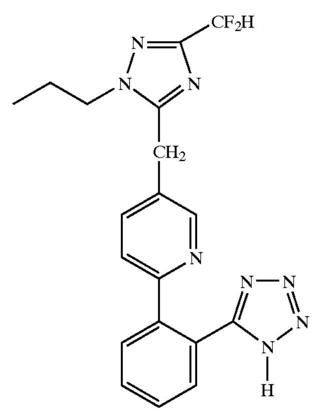 | WO #92/16523 pub. Oct. 1, 1992 |
| 163 | 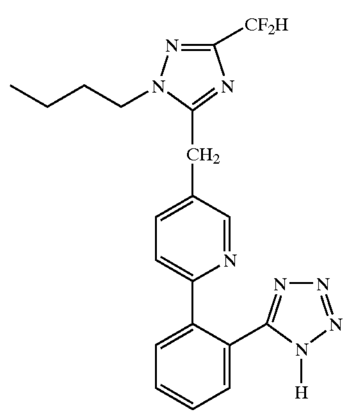 | WO #92/16523 pub. Oct. 1, 1992 |
| 164 | 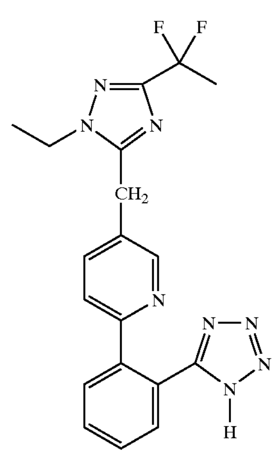 | WO #92/16523 pub. Oct. 1, 1992 |

TABLE II-continued
Angiotensin II Antagonists
| Compound # | Structure | Source |
|---|---|---|
| 165 | 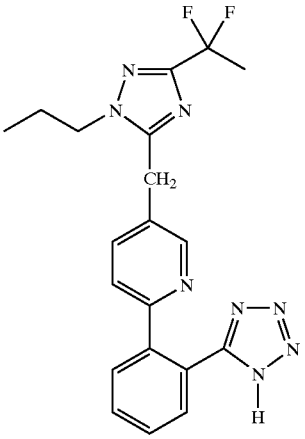 | WO #92/16523 pub. Oct. 1, 1992 |
| 166 | 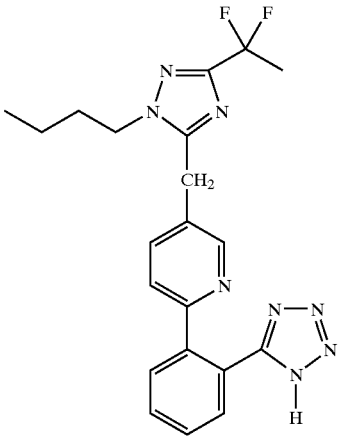 | WO #92/16523 pub. Oct. 1, 1992 |
| 167 | 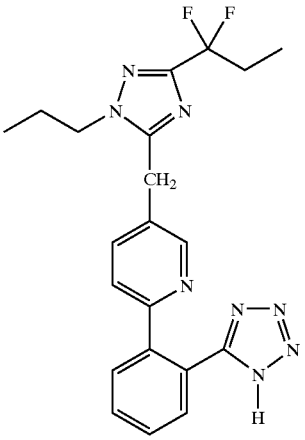 | WO #92/16523 pub. Oct. 1, 1992 |

TABLE II-continued

Angiotensin II Antagonists

| Compound # | Structure | Source |
|---|---|---|
| 168 | 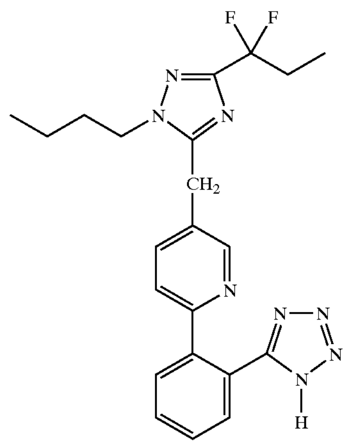 | WO #92/16523 pub. Oct. 1, 1992 |
| 169 | 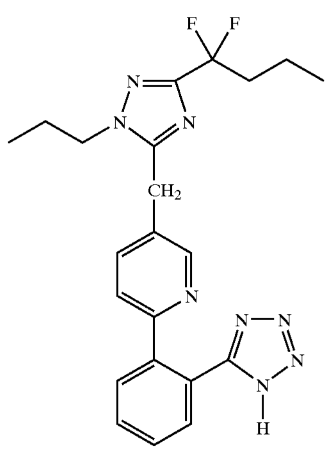 | WO #92/16523 pub. Oct. 1, 1992 |
| 170 | 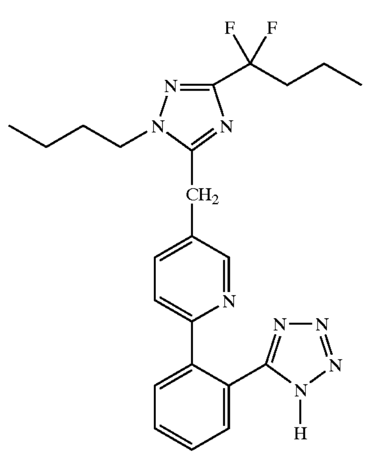 | WO #92/16523 pub. Oct. 1, 1992 |

TABLE II-continued

Angiotensin II Antagonists

| Compound # | Structure | Source |
|---|---|---|
| 171 | 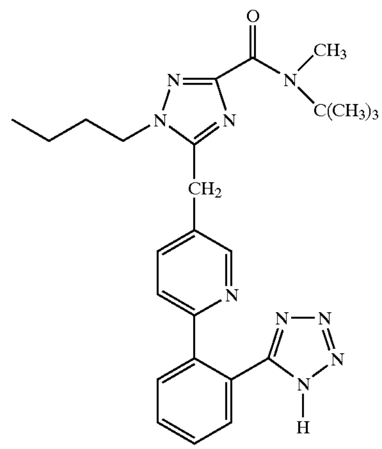 | WO #92/16523 pub. Oct. 1, 1992 |
| 172 | 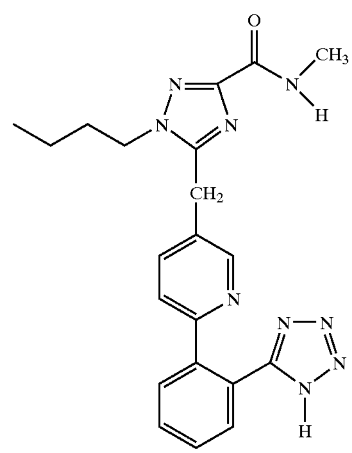 | WO #92/16523 pub. Oct. 1, 1992 |
| 173 | 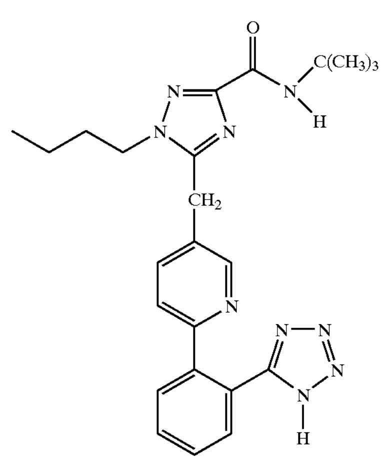 | WO #92/16523 pub. Oct. 1, 1992 |

/ 125 126
TABLE II-continued
Angiotensin II Antagonists
| Compound # | Structure | Source |
|---|---|---|
| 174 | 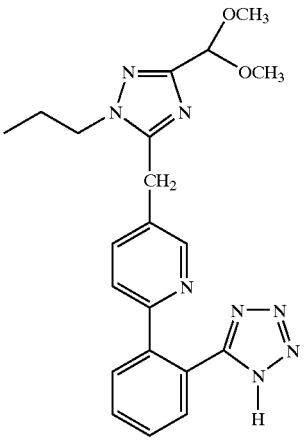 | WO #92/16523 pub. Oct. 1, 1992 |
| 175 | 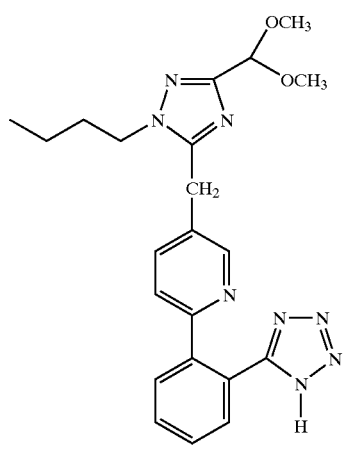 | WO #92/16523 pub. Oct. 1, 1992 |
| 176 | 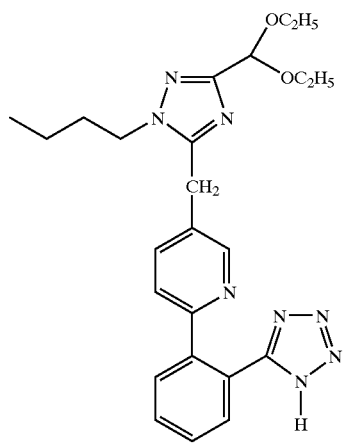 | WO #92/16523 pub. Oct. 1, 1992 |

TABLE II-continued
Angiotensin II Antagonists
| Compound # | Structure | Source |
|---|---|---|
| 177 | 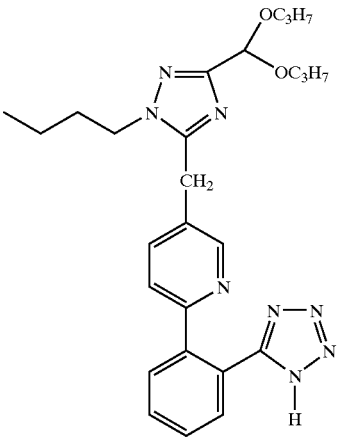 | WO #92/16523 pub. Oct. 1, 1992 |
| 178 | 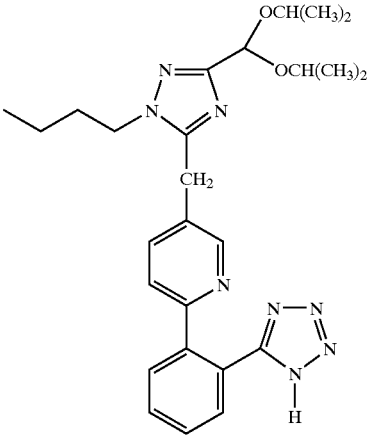 | WO #92/16523 pub. Oct. 1, 1992 |
| 179 | 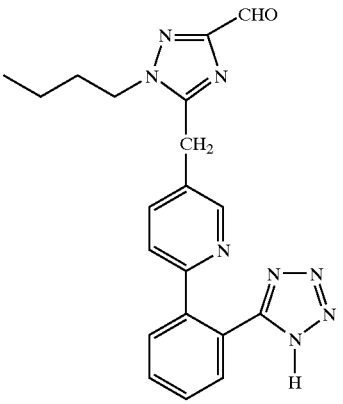 | WO #92/16523 pub. Oct. 1, 1992 |

TABLE II-continued

Angiotensin II Antagonists

| Compound # | Structure | Source |
|---|---|---|
| 180 | 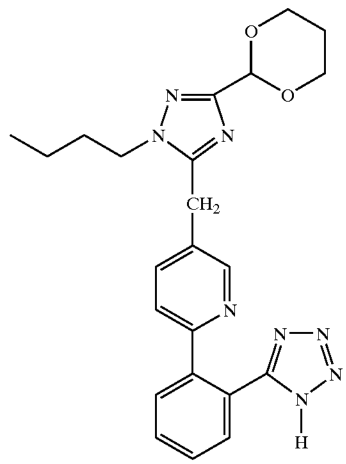 | WO #92/16523 pub. Oct. 1, 1992 |
| 181 | 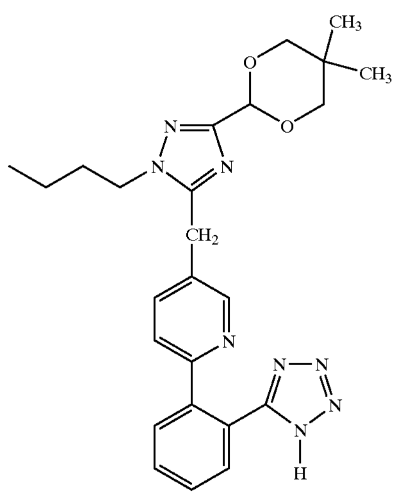 | WO #92/16523 pub. Oct. 1, 1992 |
| 182 | 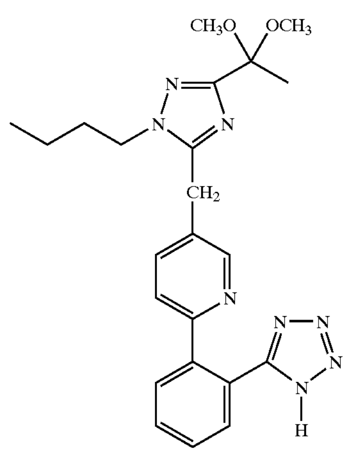 | WO #92/16523 pub. Oct. 1, 1992 |

TABLE II-continued

Angiotensin II Antagonists

| Compound # | Structure | Source |
|---|---|---|
| 183 | 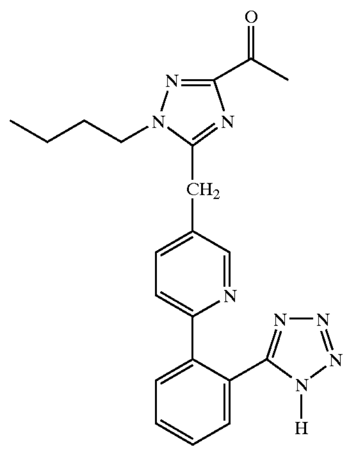 | WO #92/16523 pub. Oct. 1, 1992 |
| 184 | 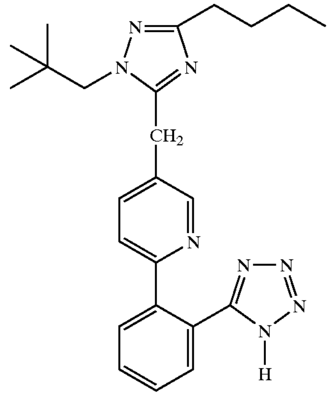 | WO #92/16523 pub. Oct. 1, 1992 |
| 185 | 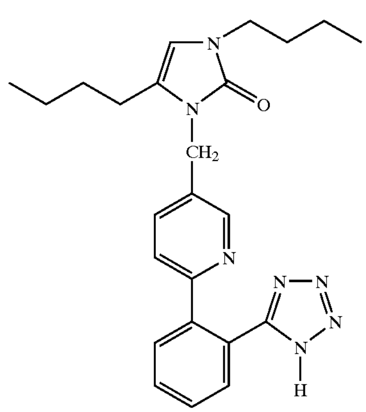 | WO #92/17469 pub. Oct. 15, 1992 |

TABLE II-continued
Angiotensin II Antagonists
| Compound # | Structure | Source |
|---|---|---|
| 186 | 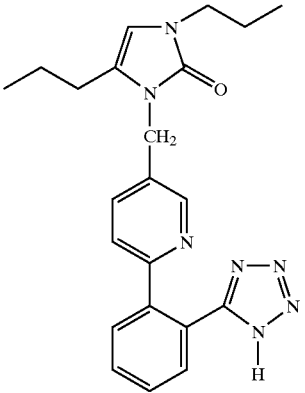 | WO #92/17469<br>pub. Oct. 15, 1992 |
| 187 | 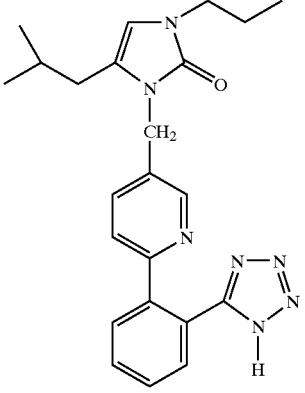 | WO #92/17469<br>pub. Oct. 15, 1992 |
| 188 | 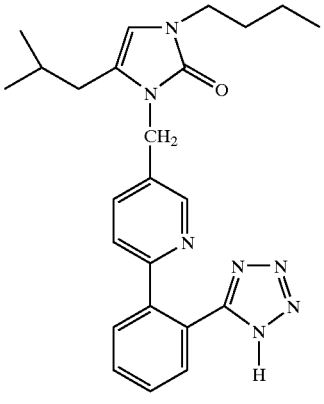 | WO #92/17469<br>pub. Oct. 15, 1992 |

TABLE II-continued

Angiotensin II Antagonists

| Compound # | Structure | Source |
|---|---|---|
| 189 | 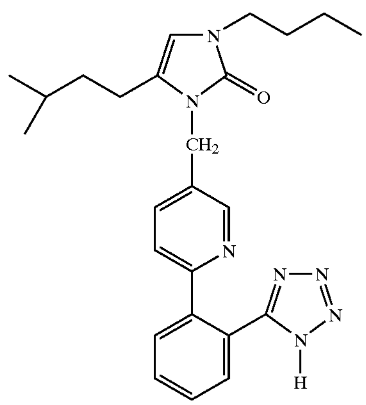 | WO #92/17469 pub. Oct. 15, 1992 |
| 190 | 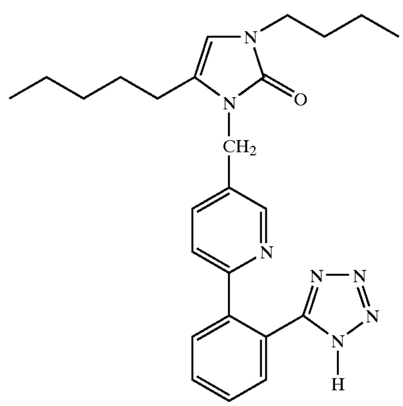 | WO #92/17469 pub. Oct. 15, 1992 |
| 191 | 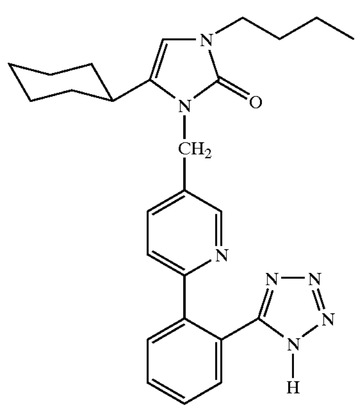 | WO #92/17469 pub. Oct. 15, 1992 |

TABLE II-continued

Angiotensin II Antagonists

| Compound # | Structure | Source |
|---|---|---|
| 192 | 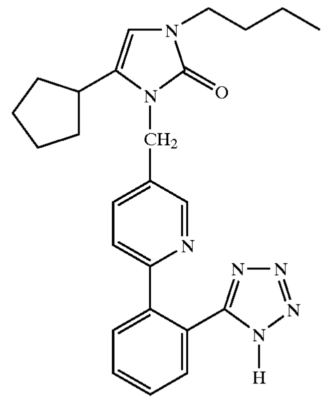 | WO #92/17469 pub. Oct. 15, 1992 |
| 193 | 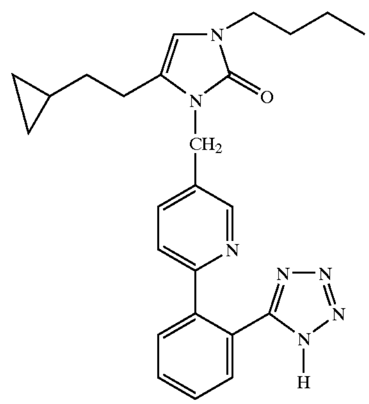 | WO #92/17469 pub. Oct. 15, 1992 |
| 194 | 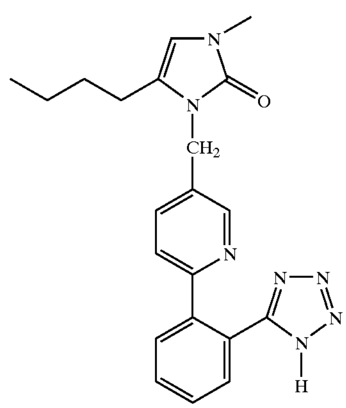 | WO #92/17469 pub. Oct. 15, 1992 |

TABLE II-continued

Angiotensin II Antagonists

| Compound # | Structure | Source |
|---|---|---|
| 195 | 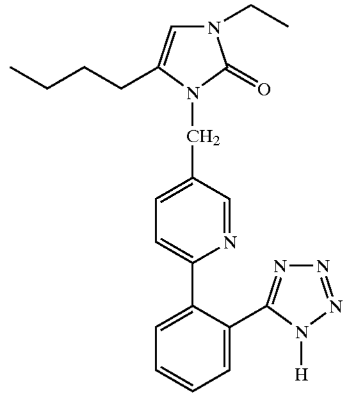 | WO #92/17469 pub. Oct. 15, 1992 |
| 196 | 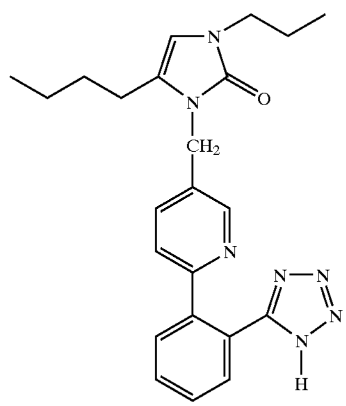 | WO #92/17469 pub. Oct. 15, 1992 |
| 197 | 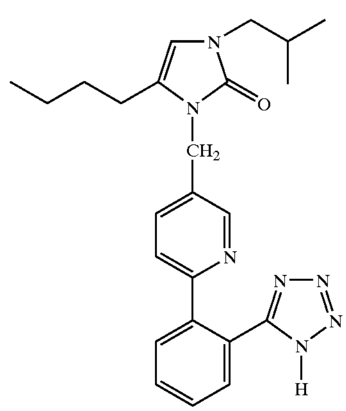 | WO #92/17469 pub. Oct. 15, 1992 |

TABLE II-continued

Angiotensin II Antagonists

| Compound # | Structure | Source |
|---|---|---|
| 198 | 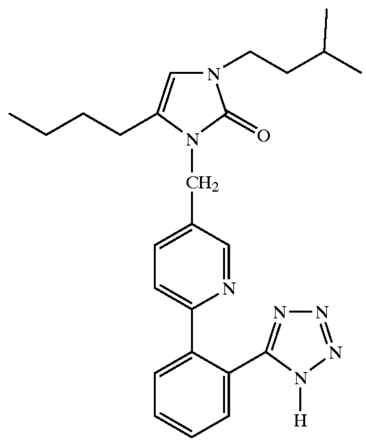 | WO #92/17469 pub. Oct. 15, 1992 |
| 199 | 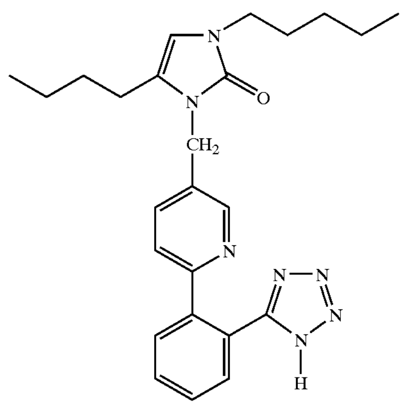 | WO #92/17469 pub. Oct. 15, 1992 |
| 200 | 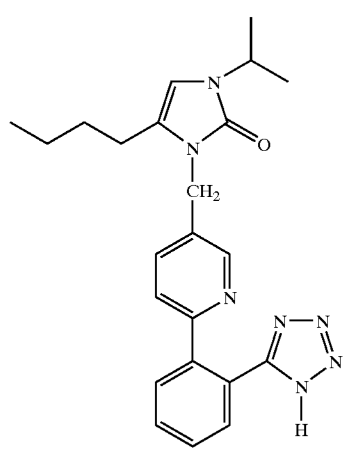 | WO #92/17469 pub. Oct. 15, 1992 |

TABLE II-continued

Angiotensin II Antagonists

| Compound # | Structure | Source |
|---|---|---|
| 201 | 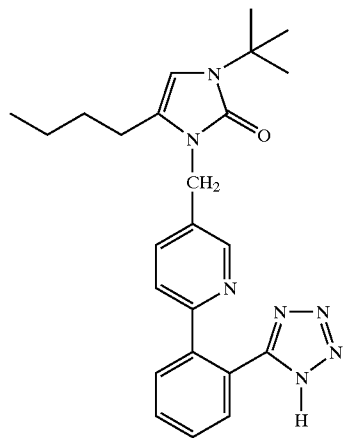 | WO #92/17469 pub. Oct. 15, 1992 |
| 202 | 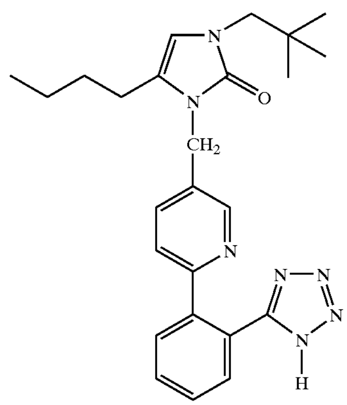 | WO #92/17469 pub. Oct. 15, 1992 |
| 203 | 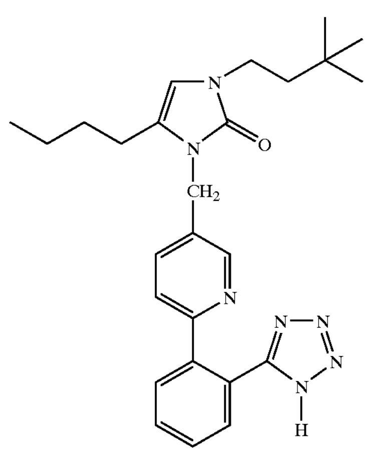 | WO #92/17469 pub. Oct. 15, 1992 |

TABLE II-continued

Angiotensin II Antagonists

| Compound # | Structure | Source |
|---|---|---|
| 204 | 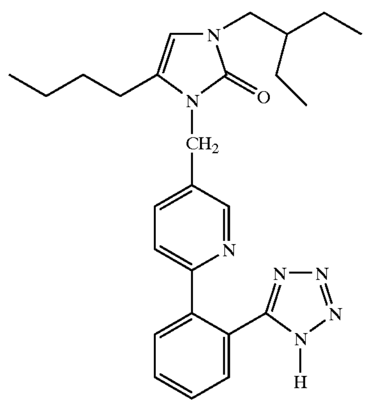 | WO #92/17469 pub. Oct. 15, 1992 |
| 205 | 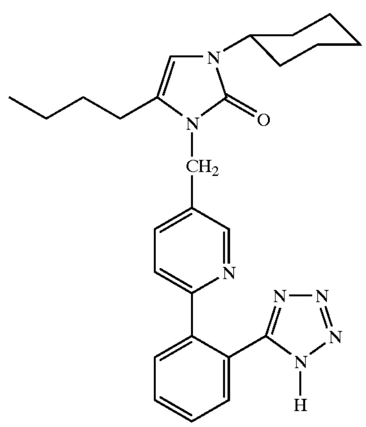 | WO #92/17469 pub. Oct. 15, 1992 |
| 206 | 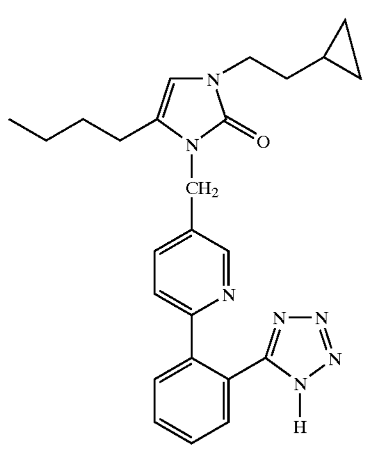 | WO #92/17469 pub. Oct. 15, 1992 |

TABLE II-continued

Angiotensin II Antagonists

| Compound # | Structure | Source |
|---|---|---|
| 207 | 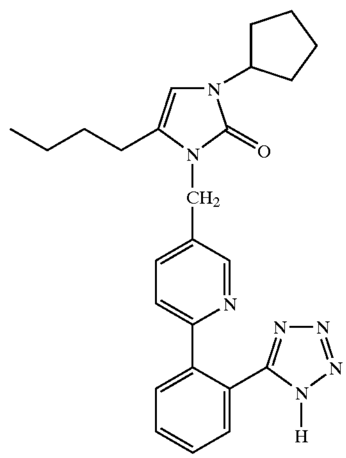 | WO #92/17469 pub. Oct. 15, 1992 |
| 208 | 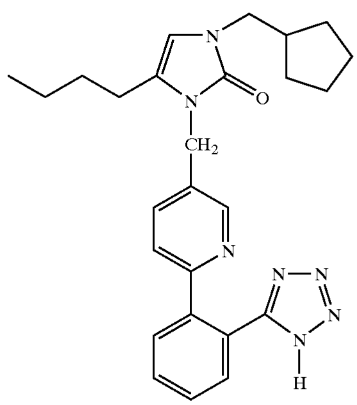 | WO #92/17469 pub. Oct. 15, 1992 |
| 209 | 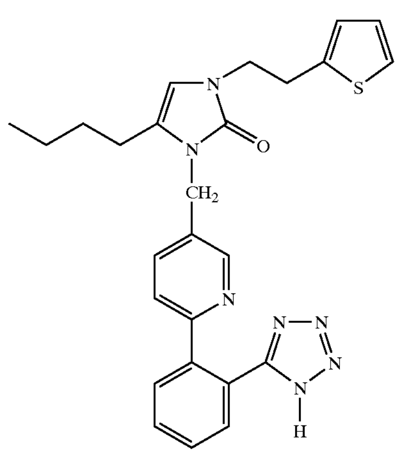 | WO #92/17469 pub. Oct. 15, 1992 |

TABLE II-continued
Angiotensin II Antagonists
| Compound # | Structure | Source |
|---|---|---|
| 210 | 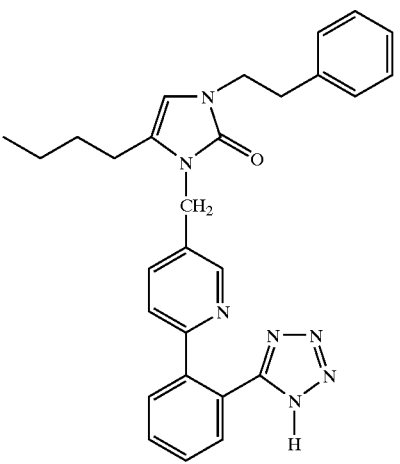 | WO #92/17469 pub. Oct. 15, 1992 |
| 211 | 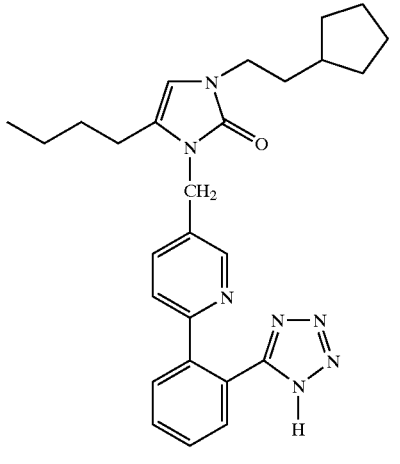 | WO #92/17469 pub. Oct. 15, 1992 |
| 212 | 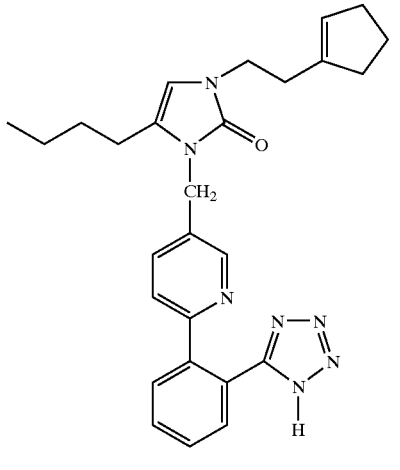 | WO #92/17469 pub. Oct. 15, 1992 |

TABLE II-continued

Angiotensin II Antagonists

| Compound # | Structure | Source |
|---|---|---|
| 213 | 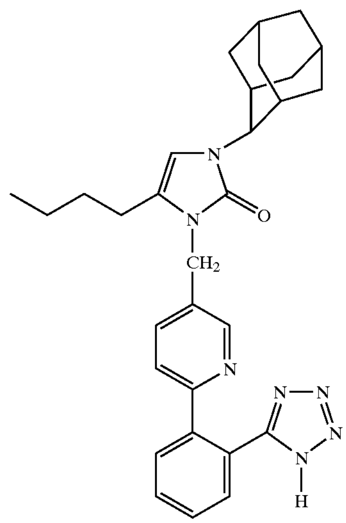 | WO #92/17469 pub. Oct. 15, 1992 |
| 214 | 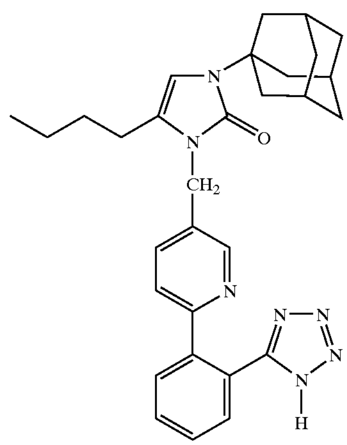 | WO #92/17469 pub. Oct. 15, 1992 |
| 215 | 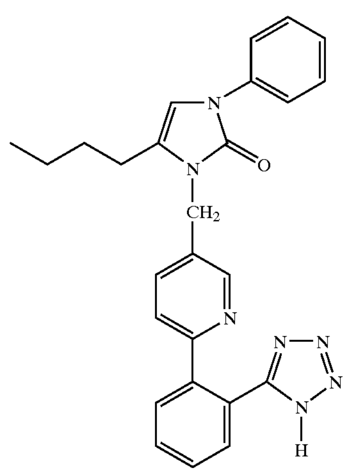 | WO #92/17469 pub. Oct. 15, 1992 |

TABLE II-continued

Angiotensin II Antagonists

| Compound # | Structure | Source |
|---|---|---|
| 216 | 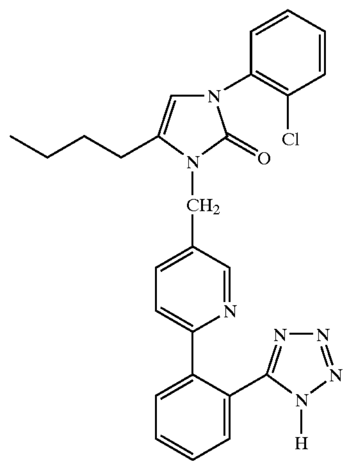 | WO #92/17469 pub. Oct. 15, 1992 |
| 217 | 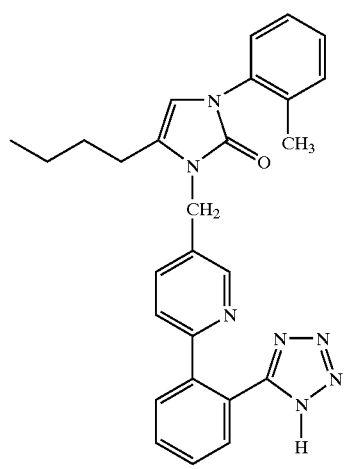 | WO #92/17469 pub. Oct. 15, 1992 |
| 218 | 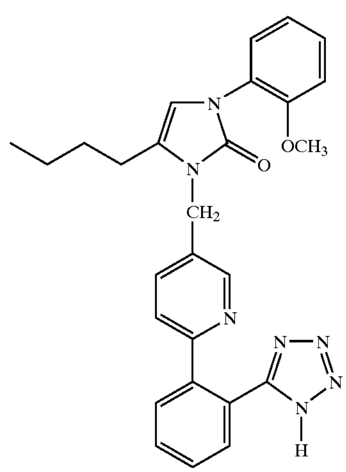 | WO #92/17469 pub. Oct. 15, 1992 |

TABLE II-continued
Angiotensin II Antagonists
| Compound # | Structure | Source |
|---|---|---|
| 219 | 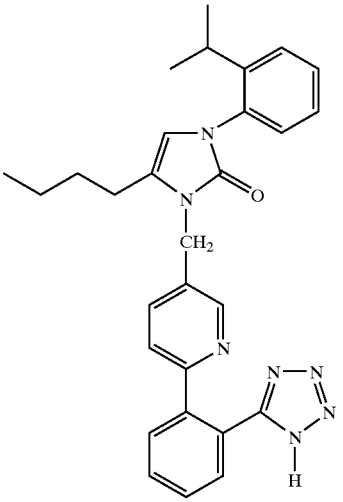 | WO #92/17469 pub. Oct. 15, 1992 |
| 220 | 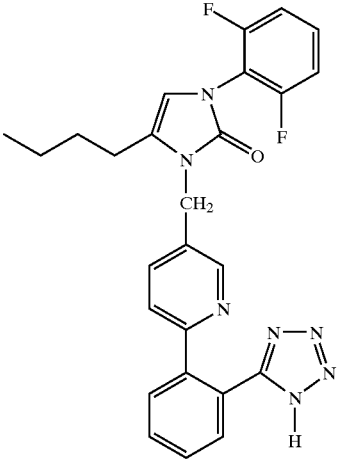 | WO #92/17469 pub. Oct. 15, 1992 |
| 221 | 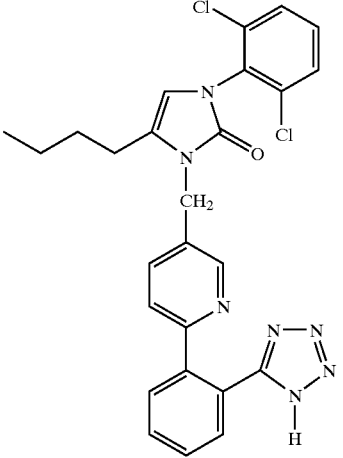 | WO #92/17469 pub. Oct. 15, 1992 |

TABLE II-continued

Angiotensin II Antagonists

| Compound # | Structure | Source |
|---|---|---|
| 222 | 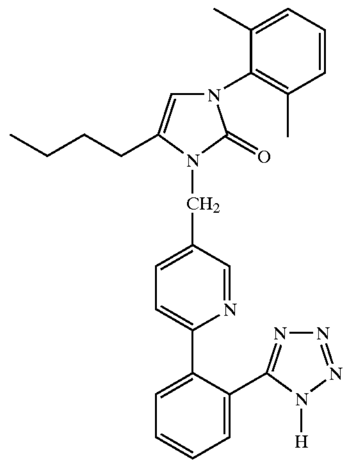 | WO #92/17469 pub. Oct. 15, 1992 |
| 223 | 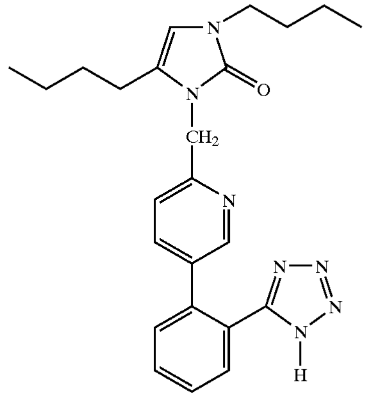 | WO #92/17469 pub. Oct. 15, 1992 |
| 224 | 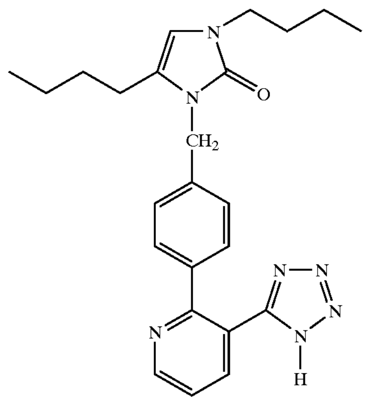 | WO #92/17469 pub. Oct. 15, 1992 |

TABLE II-continued
Angiotensin II Antagonists
| Compound # | Structure | Source |
|---|---|---|
| 225 | 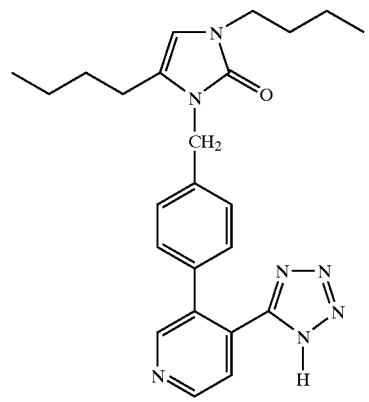 | WO #92/17469 pub. Oct. 15, 1992 |
| 226 | 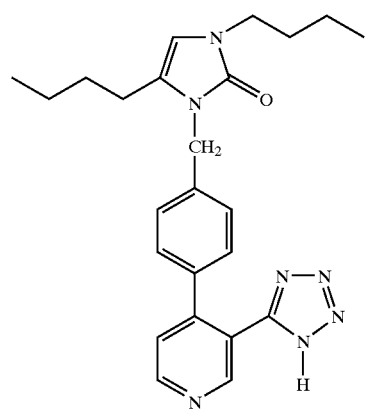 | WO #92/17469 pub. Oct. 15, 1992 |
| 227 | 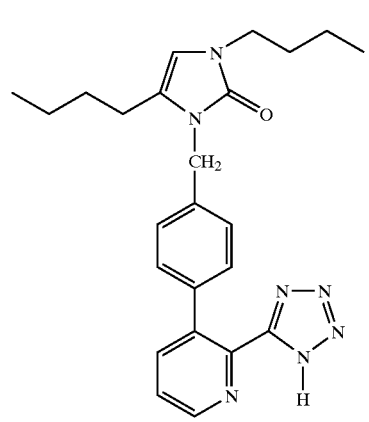 | WO #92/17469 pub. Oct. 15, 1992 |

TABLE II-continued
Angiotensin II Antagonists
| Compound # | Structure | Source |
|---|---|---|
| 228 | 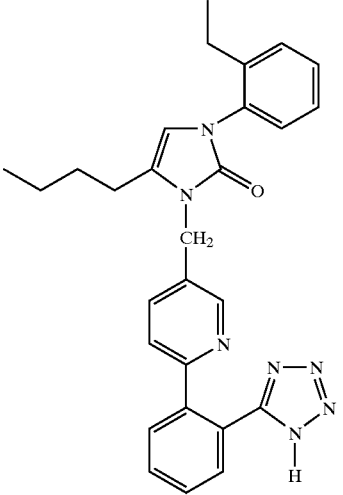 | |
| 229 | 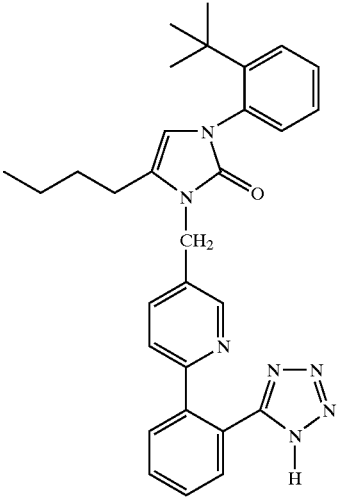 | |
| 230 | 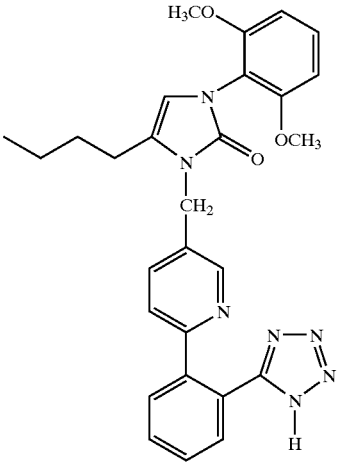 | |

TABLE II-continued
Angiotensin II Antagonists
| Compound # | Structure | Source |
|---|---|---|
| 231 | 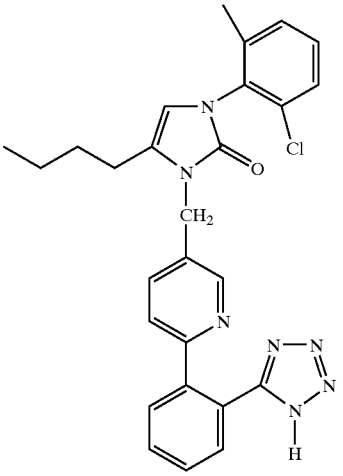 | |
| 232 | 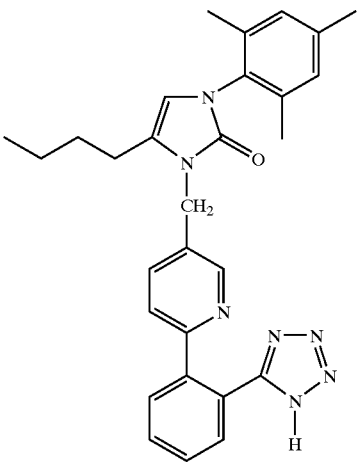 | |
| 233 | 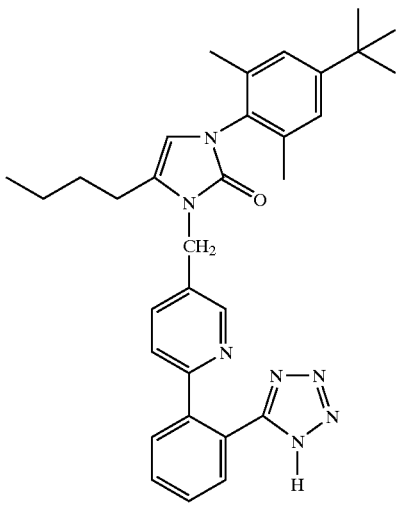 | |

TABLE II-continued

Angiotensin II Antagonists

| Compound # | Structure | Source |
|---|---|---|
| 234 | 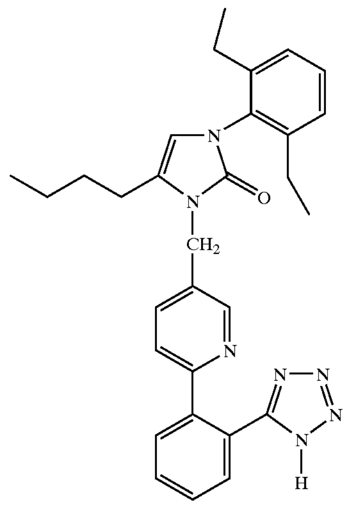 | |
| 235 | 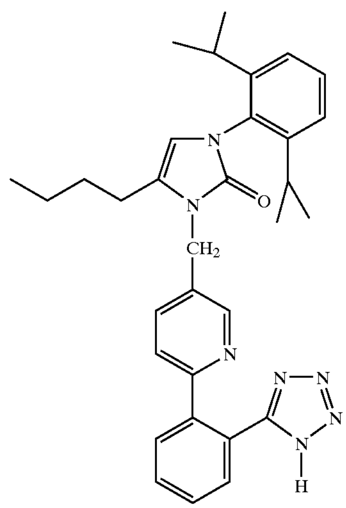 | |
| 236 | 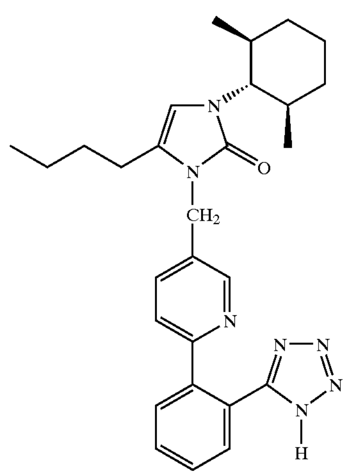 | |

TABLE II-continued
Angiotensin II Antagonists
| Compound # | Structure | Source |
|---|---|---|
| 237 | 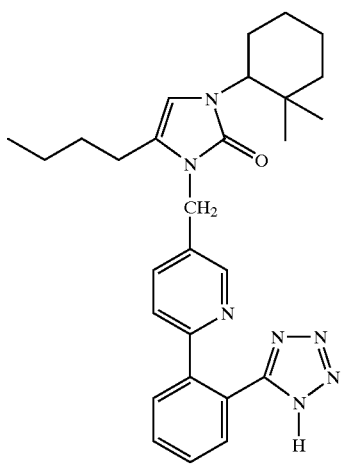 | |
| 238 | 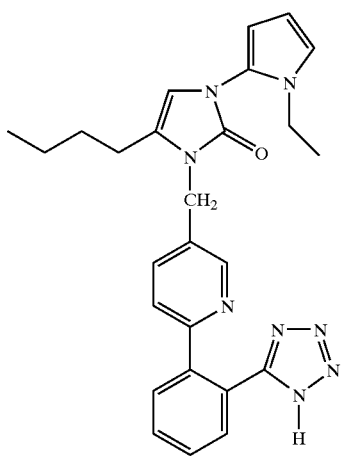 | |
| 239 | 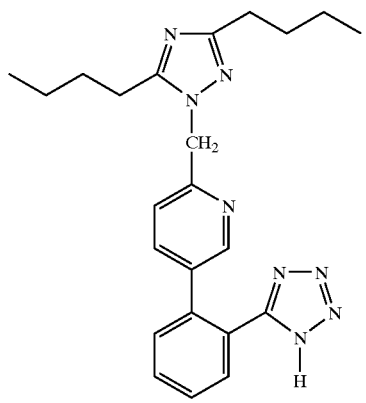 | WO #92/18092 pub. Oct. 29, 1992 |

TABLE II-continued

Angiotensin II Antagonists

| Compound # | Structure | Source |
|---|---|---|
| 240 | | WO #92/18092 pub. Oct. 29, 1992 |
| 241 | | WO #92/18092 pub. Oct. 29, 1992 |
| 242 | | WO #92/18092 pub. Oct. 29, 1992 |

TABLE II-continued

Angiotensin II Antagonists

| Compound # | Structure | Source |
|---|---|---|
| 243 | 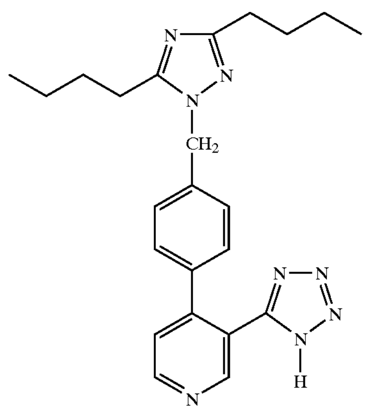 | WO #92/18092 pub. Oct. 29, 1992 |
| 244 | 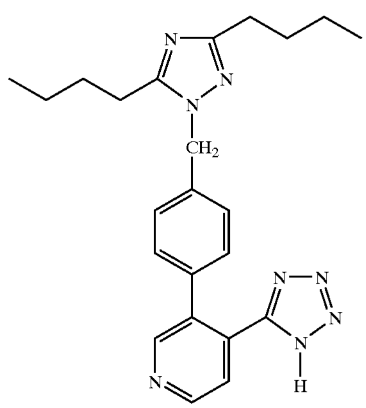 | WO #92/18092 pub. Oct. 29, 1992 |
| 245 | 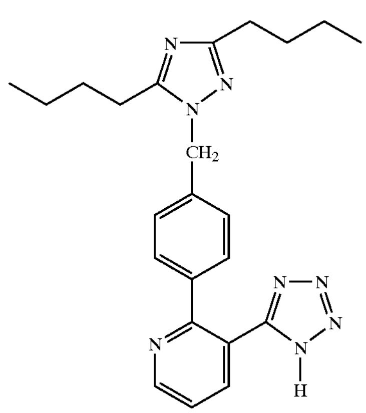 | WO #92/18092 pub. Oct. 29, 1992 |

TABLE II-continued

Angiotensin II Antagonists

| Compound # | Structure | Source |
|---|---|---|
| 246 | 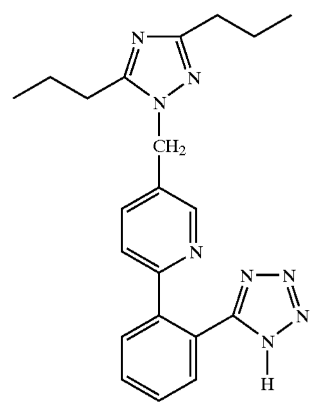 | WO #92/18092 pub. Oct. 29, 1992 |
| 247 | 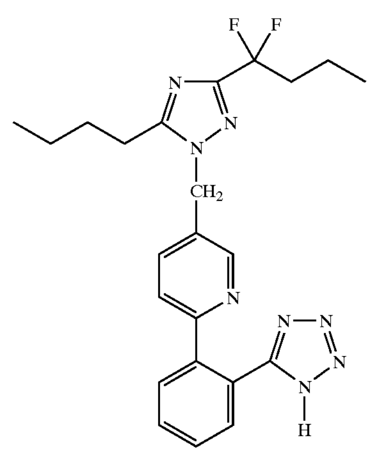 | WO #92/18092 pub. Oct. 29, 1992 |
| 248 | 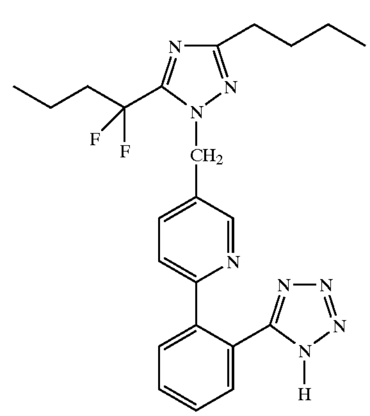 | WO #92/18092 pub. Oct. 29, 1992 |

TABLE II-continued

Angiotensin II Antagonists

| Compound # | Structure | Source |
|---|---|---|
| 249 | 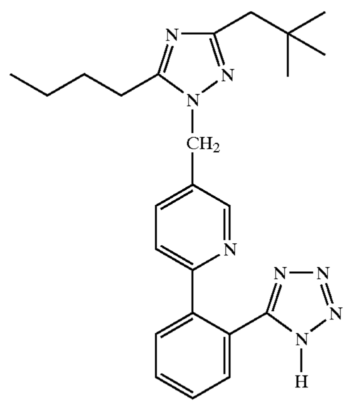 | WO #92/18092 pub. Oct. 29, 1992 |
| 250 | 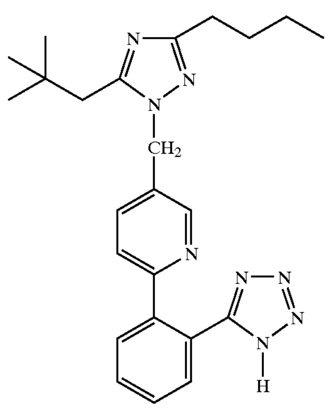 | WO #92/18092 pub. Oct. 29, 1992 |
| 251 | 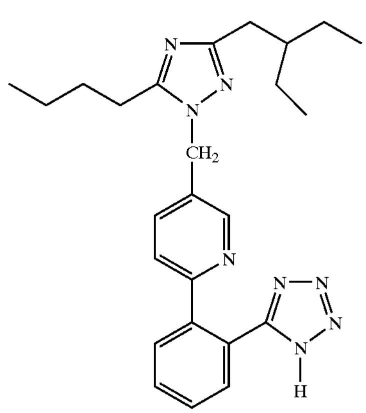 | WO #92/18092 pub. Oct. 29, 1992 |

TABLE II-continued

Angiotensin II Antagonists

| Compound # | Structure | Source |
|---|---|---|
| 252 | 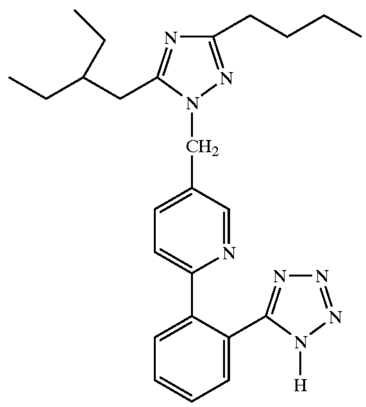 | WO #92/18092 pub. Oct. 29, 1992 |
| 253 | 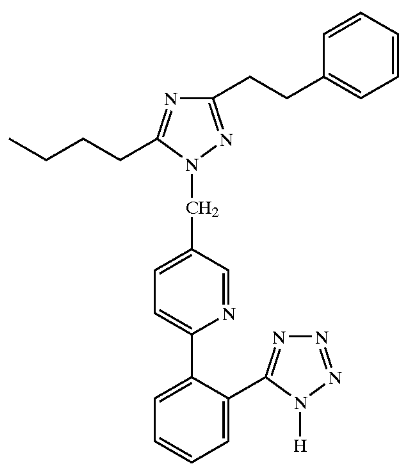 | WO #92/18092 pub. Oct. 29, 1992 |
| 254 | 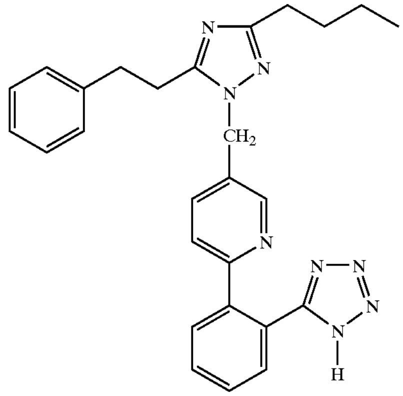 | WO #92/18092 pub. Oct. 29, 1992 |

TABLE II-continued
Angiotensin II Antagonists
| Compound # | Structure | Source |
|---|---|---|
| 255 | 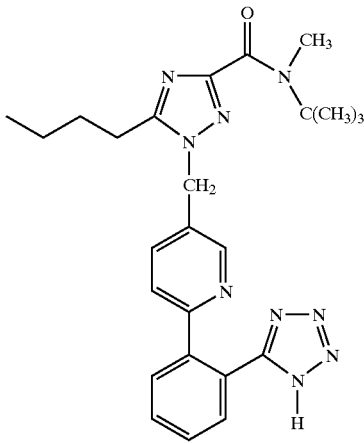 | WO #92/18092 pub. Oct. 29, 1992 |
| 256 | 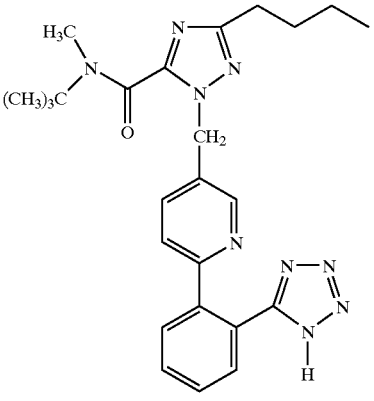 | WO #92/18092 pub. Oct. 29, 1992 |
| 257 | 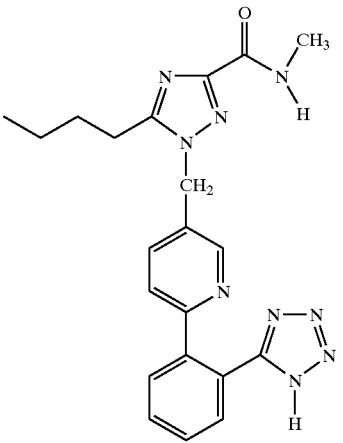 | WO #92/18092 pub. Oct. 29, 1992 |

TABLE II-continued
Angiotensin II Antagonists
| Compound # | Structure | Source |
|---|---|---|
| 258 | 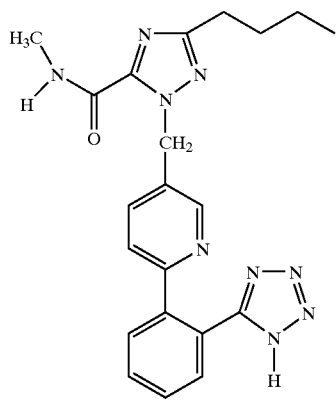 | WO #92/18092 pub. Oct. 29, 1992 |
| 259 | 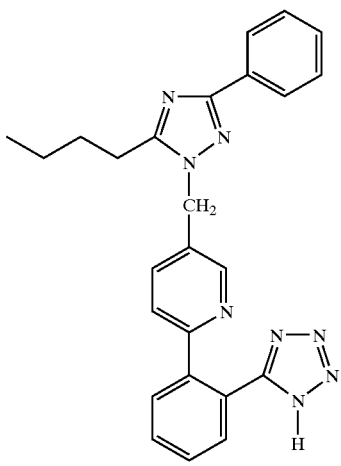 | WO #92/18092 pub. Oct. 29, 1992 |
| 260 | 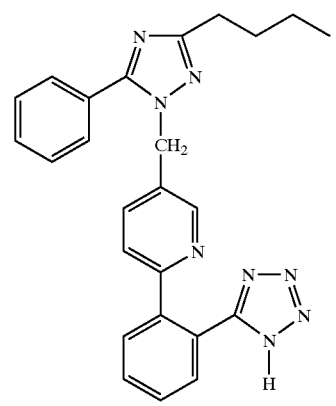 | WO #92/18092 pub. Oct. 29, 1992 |

TABLE II-continued
Angiotensin II Antagonists
| Compound # | Structure | Source |
|---|---|---|
| 261 | 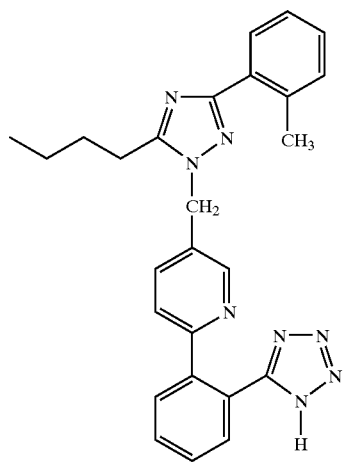 | WO #92/18092 pub. Oct. 29, 1992 |
| 262 | 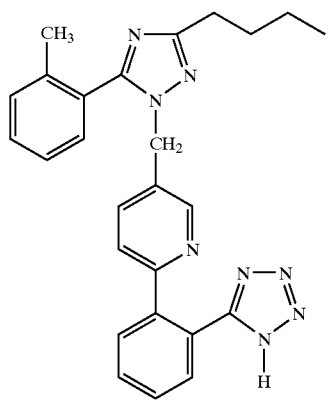 | WO #92/18092 pub. Oct. 29, 1992 |
| 263 | 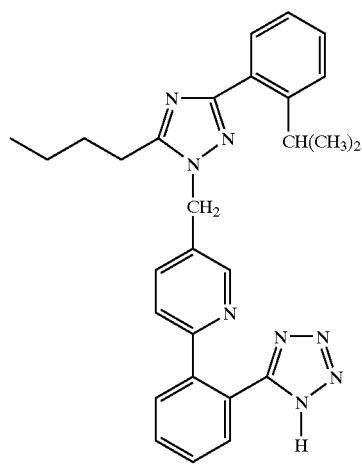 | WO #92/18092 pub. Oct. 29, 1992 |

TABLE II-continued
Angiotensin II Antagonists
| Compound # | Structure | Source |
|---|---|---|
| 264 | 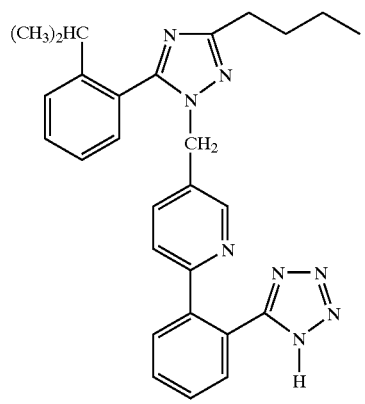 | WO #92/18092 pub. Oct. 29, 1992 |
| 265 | 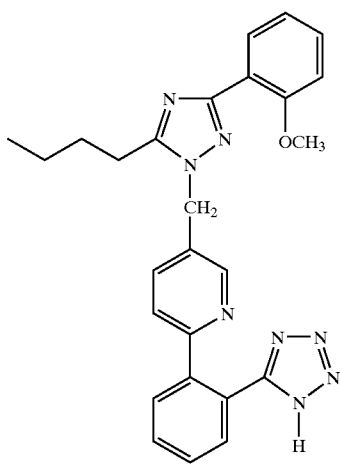 | WO #92/18092 pub. Oct. 29, 1992 |
| 266 | 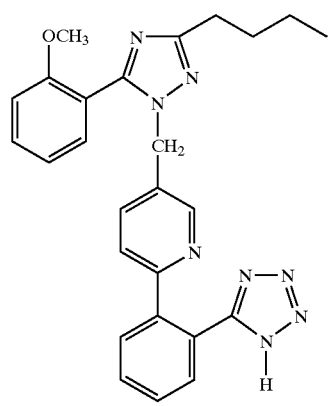 | WO #92/18092 pub. Oct. 29, 1992 |

TABLE II-continued
Angiotensin II Antagonists
| Compound # | Structure | Source |
|---|---|---|
| 267 | 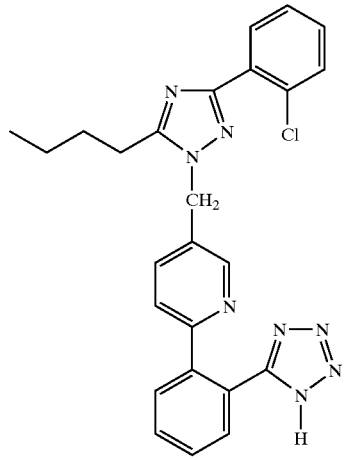 | WO #92/18092 pub. Oct. 29, 1992 |
| 268 | 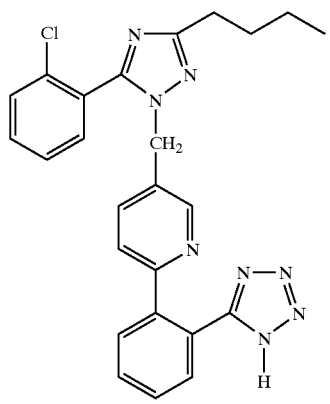 | WO #92/18092 pub. Oct. 29, 1992 |
| 269 | 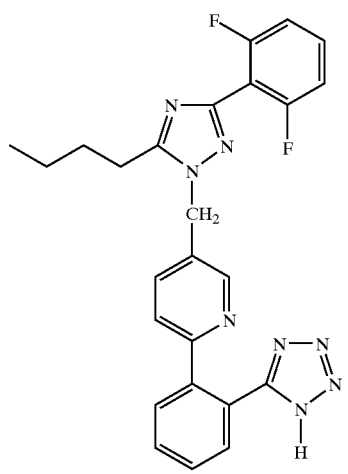 | WO #92/18092 pub. Oct. 29, 1992 |

TABLE II-continued

Angiotensin II Antagonists

| Compound # | Structure | Source |
|---|---|---|
| 270 | 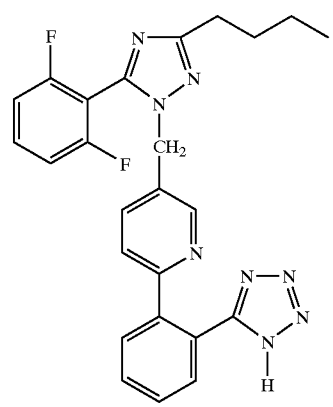 | WO #92/18092<br>pub. Oct. 29, 1992 |
| 271 | 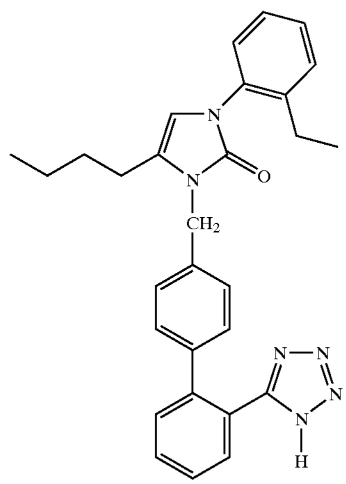 | PCT/US95/02156<br>filed Mar. 8, 1994 |
| 272 | 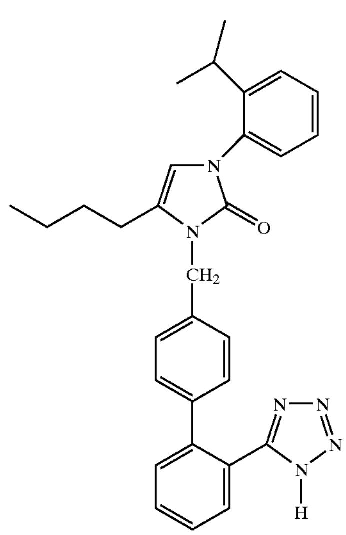 | PCT/US94/02156<br>filed Mar. 8, 1994 |

TABLE II-continued

Angiotensin II Antagonists

| Compound # | Structure | Source |
| --- | --- | --- |
| 273 | 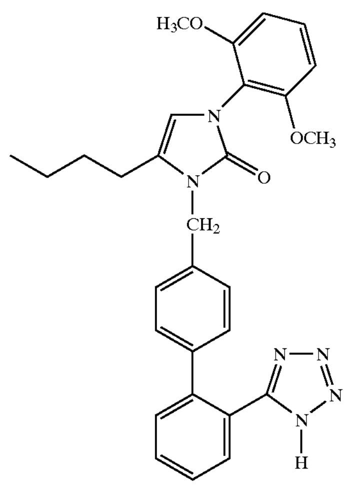 | PCT/US94/02156 filed Mar. 8, 1994 |
| 274 | 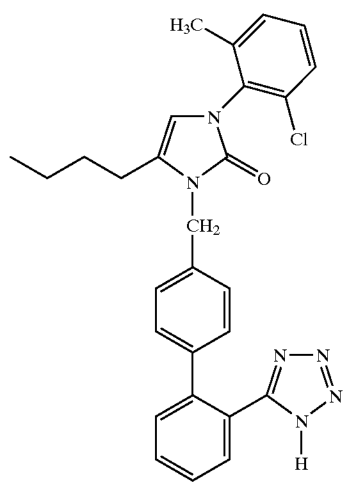 | PCT/US94/02156 filed Mar. 8, 1994 |
| 275 | 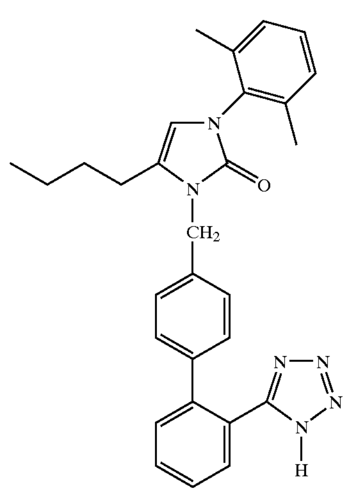 | PCT/US94/02156 filed Mar. 8, 1994 |

TABLE II-continued

Angiotensin II Antagonists

| Compound # | Structure | Source |
|---|---|---|
| 276 | 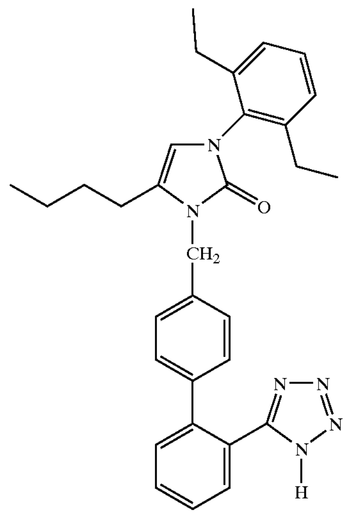 | PCT/US94/02156 filed Mar. 8, 1994 |
| 277 | 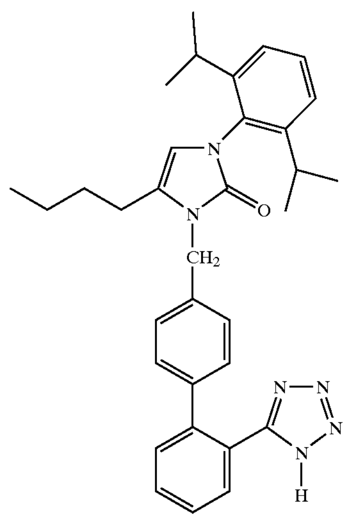 | PCT/US94/02156 filed Mar. 8, 1994 |
| 278 | 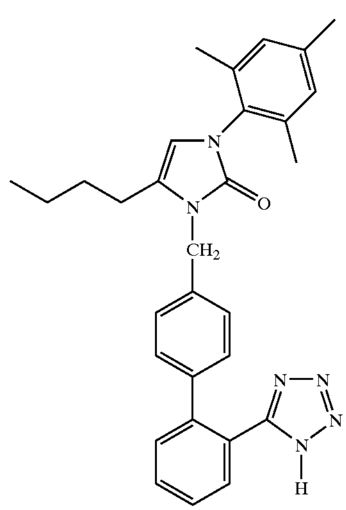 | PCT/US94/02156 filed Mar. 8, 1994 |

TABLE II-continued

Angiotensin II Antagonists

| Compound # | Structure | Source |
|---|---|---|
| 279 | 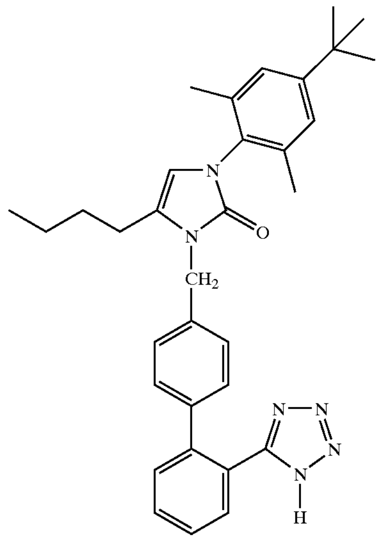 | PCT/US94/02156 filed Mar. 8, 1994 |
| 280 | 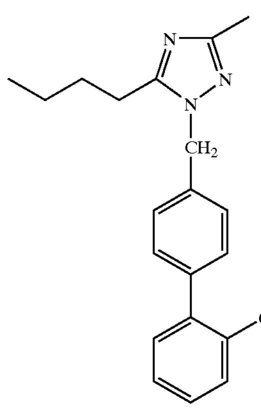 | WO #91/17148 pub. Nov. 14, 1991 |
| 281 | 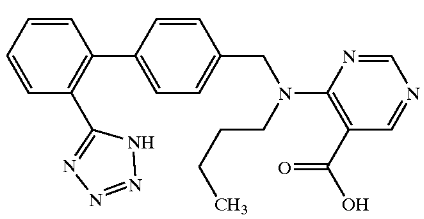 | EP #475,206 pub. Mar. 18, 1992 |
| 282 | 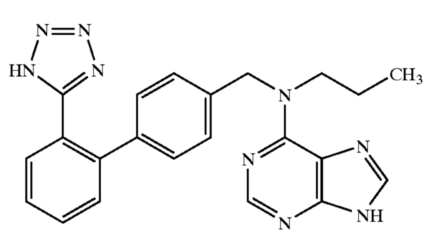 | WO #93/18035 pub. Sep. 16, 1993 |

TABLE II-continued

Angiotensin II Antagonists

| Compound # | Structure | Source |
|---|---|---|
| 283 | 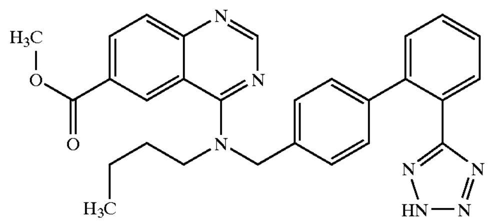 | WO #93/17628 pub. Sep. 16, 1993 |
| 284 | 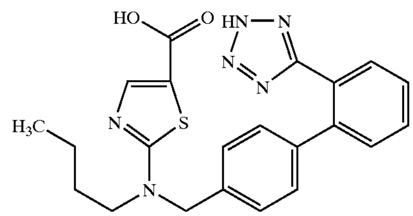 | WO #93/17681 pub. Sep. 16, 1993 |
| 285 | 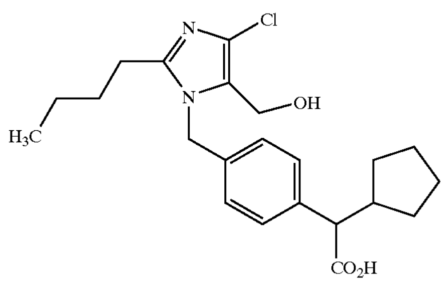 | EP #513,533 pub. Nov. 19, 1992 |
| 286 | 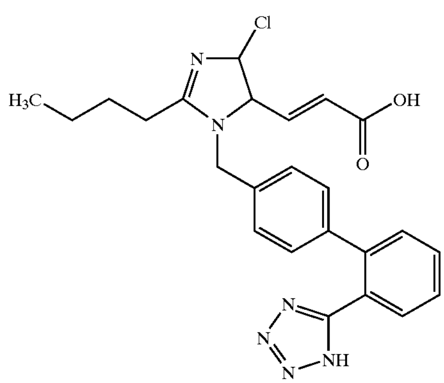 | EP #535,463 pub. Apr. 7, 1993 |
| 287 | 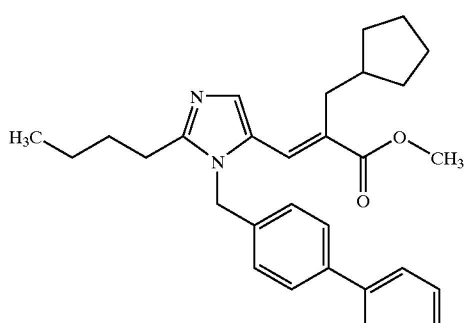 | EP #535,465 pub. Apr. 7, 1993 |

TABLE II-continued

Angiotensin II Antagonists

| Compound # | Structure | Source |
|---|---|---|
| 288 | 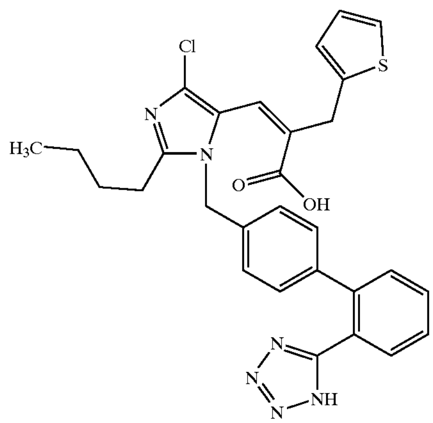 | EP #539,713<br>pub. May 5, 1993 |
| 289 | 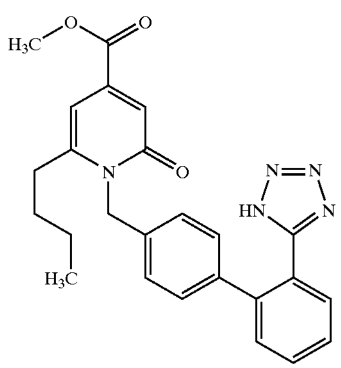 | EP #542,059<br>pub. May 19, 1993 |
| 290 | 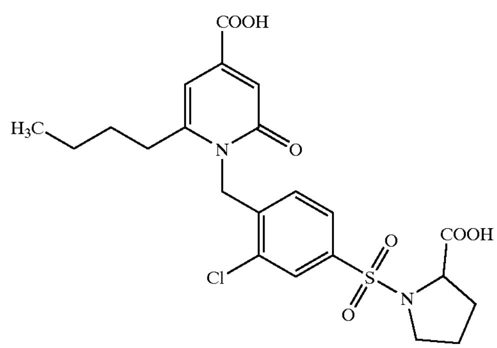 | EP #05 557,843<br>pub. Sep. 1, 1993 |
| 291 | 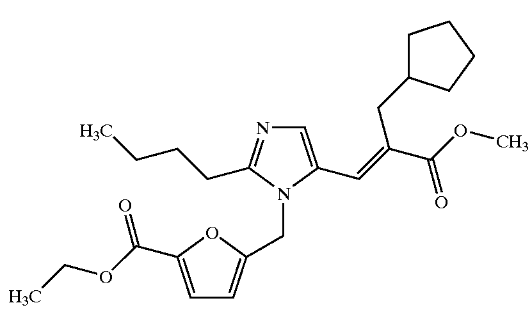 | EP #563,705<br>pub. Oct. 6, 1993 |

TABLE II-continued

Angiotensin II Antagonists

| Compound # | Structure | Source |
|---|---|---|
| 292 | 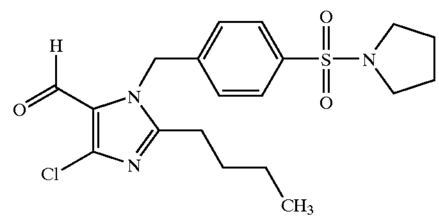 | EP #562,261<br>pub. Sep. 29, 1993 |
| 293 | 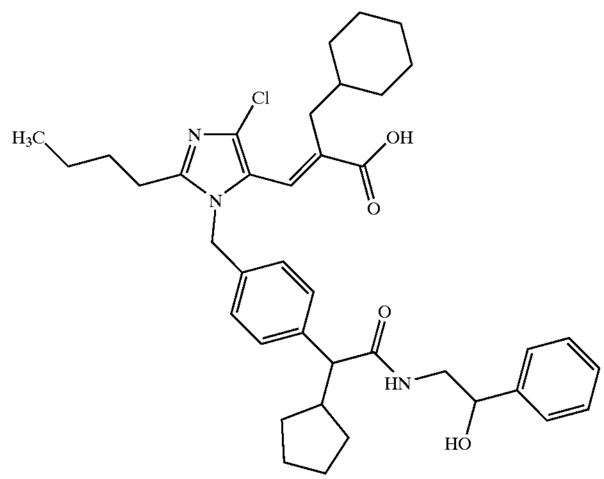 | EP #05 557,843<br>pub. Sep. 15, 1993 |
| 294 | 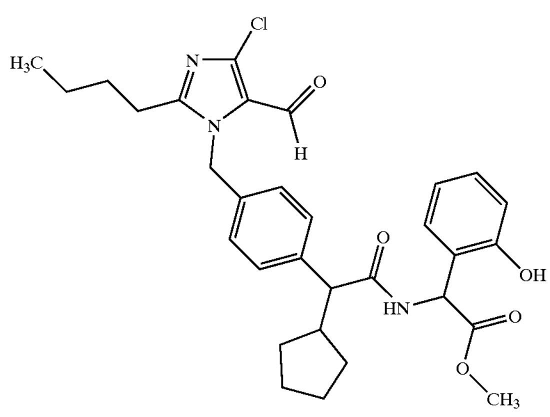 | EP #560,163<br>pub. Sep. 15, 1993 |
| 295 | 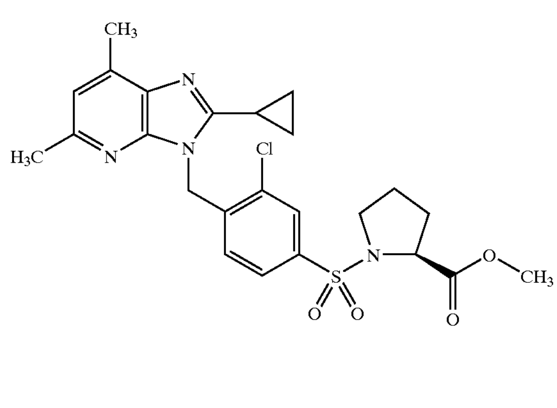 | EP #564,788<br>pub. Oct. 13, 1993 |

TABLE II-continued

Angiotensin II Antagonists

| Compound # | Structure | Source |
|---|---|---|
| 296 | 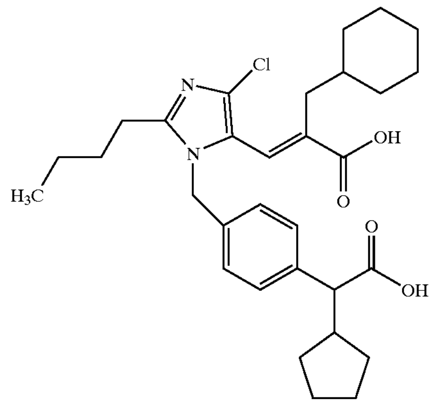 | EP #565,986 pub. Oct. 20, 1993 |
| 297 | 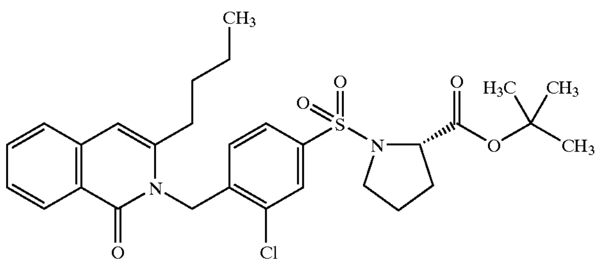 | EP #0,569,795 pub. Nov. 18, 1993 |
| 298 | 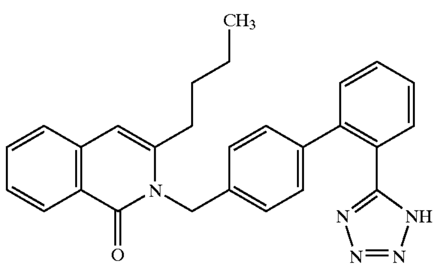 | EP #0,569,794 pub. Nov. 18, 1993 |
| 299 | 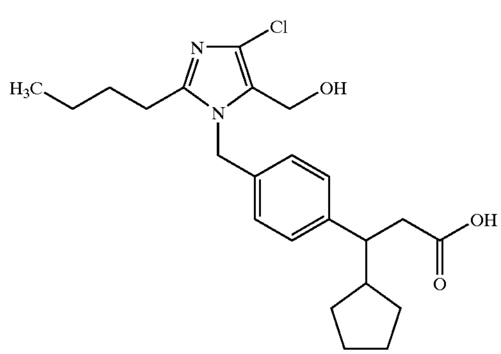 | EP #0,578,002 pub. Jan. 12, 1994 |

TABLE II-continued

Angiotensin II Antagonists

| Compound # | Structure | Source |
|---|---|---|
| 300 | 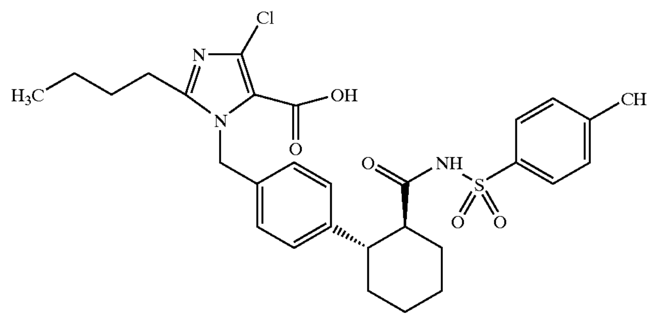 | EP #581,003 pub. Feb. 2, 1994 |
| 301 | 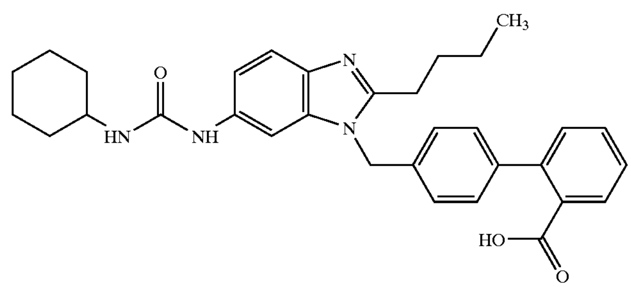 | EP #392,317 pub. Oct. 17, 1990 |
| 302 | 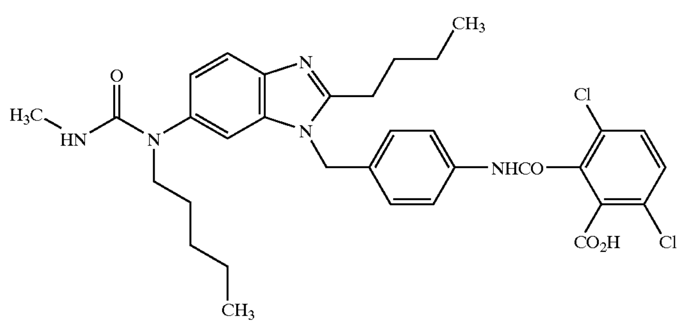 | EP #392,317 pub. Oct. 17, 1990 |
| 303 | 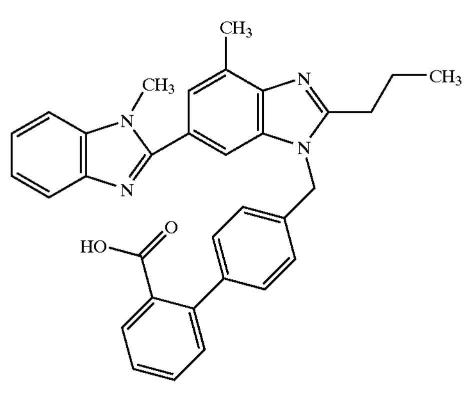 | EP #502,314 pub. Sep. 9, 1992 |

TABLE II-continued

Angiotensin II Antagonists

| Compound # | Structure | Source |
|---|---|---|
| 304 | 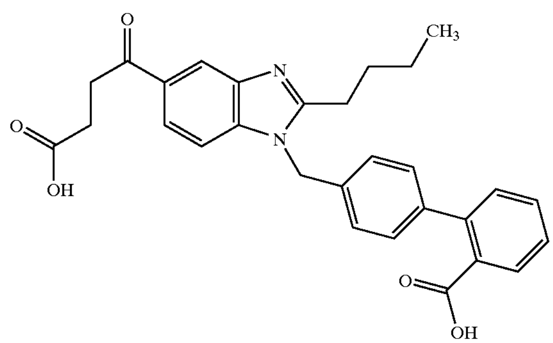 | EP #468,740<br>pub. Jan. 29, 1992 |
| 305 | 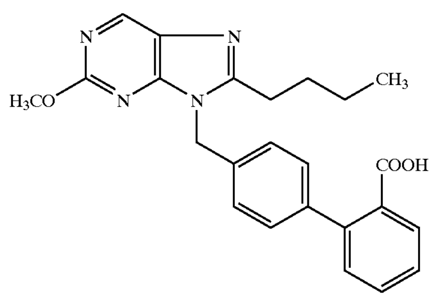 | EP #470,543<br>pub. Feb. 12, 1992 |
| 306 | 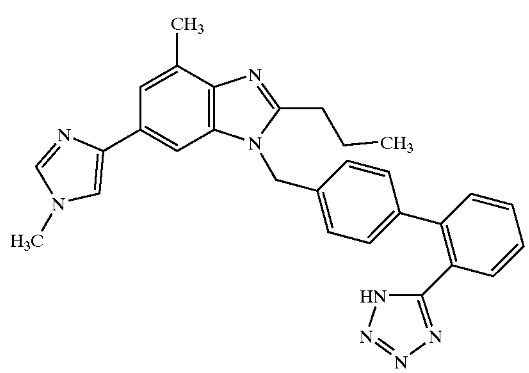 | EP #502,314<br>pub. Sep. 9, 1992 |
| 307 | 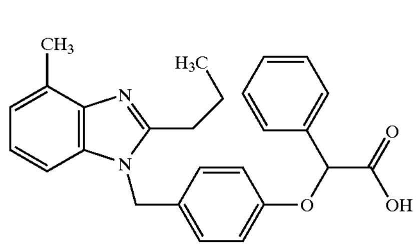 | EP #529,253<br>pub. Mar. 3, 1993 |

TABLE II-continued

Angiotensin II Antagonists

| Compound # | Structure | Source |
|---|---|---|
| 308 | 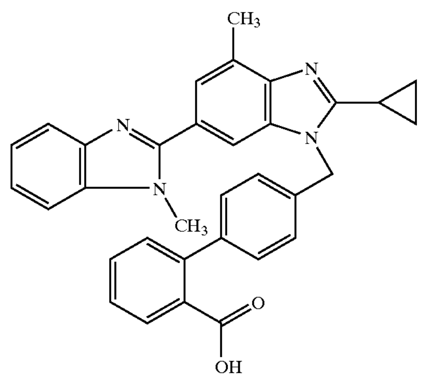 | EP #543,263 pub. May 26, 1993 |
| 309 | 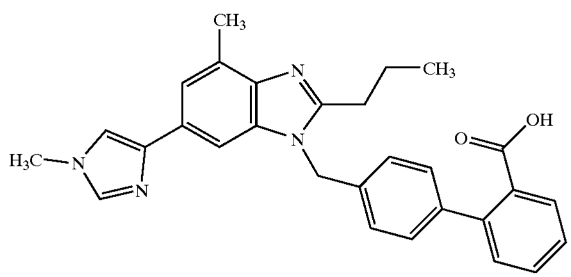 | EP #552,765 pub. Jul. 28, 1993 |
| 310 | 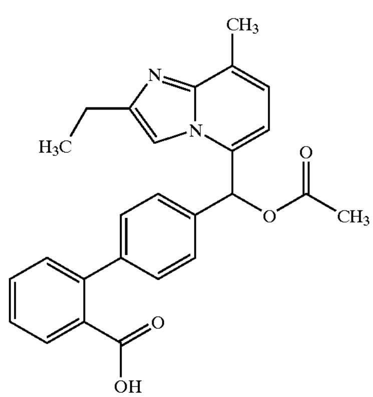 | EP #555,825 pub. Aug. 18, 1993 |
| 311 | 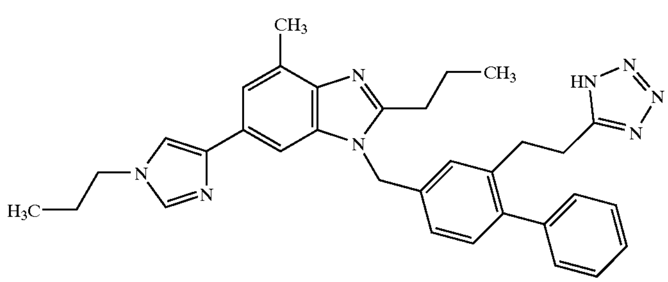 | EP #556,789 pub. Aug. 25, 1993 |

TABLE II-continued

Angiotensin II Antagonists

| Compound # | Structure | Source |
|---|---|---|
| 312 | 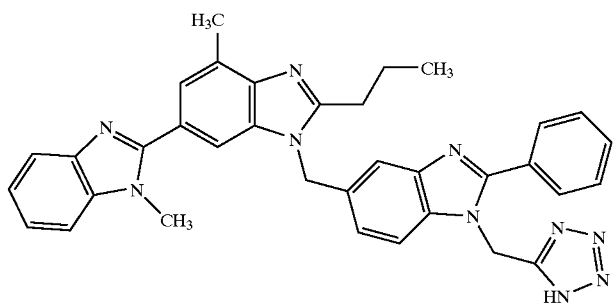 | EP #560,330 pub. Sep. 15, 1993 |
| 313 | 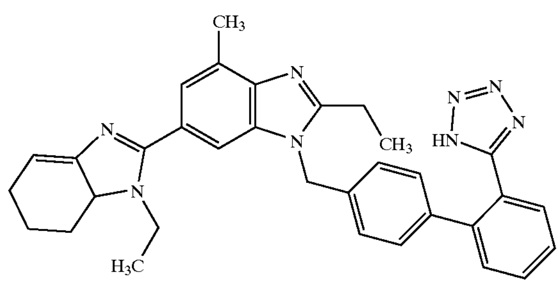 | EP #566,020 pub. Oct. 20, 1993 |
| 314 | 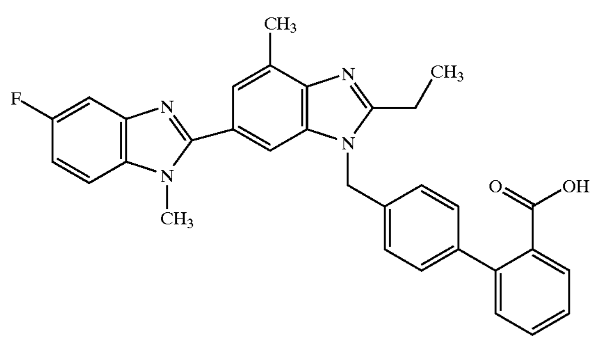 | EP #581,166 pub. Feb. 2, 1994 |
| 315 | 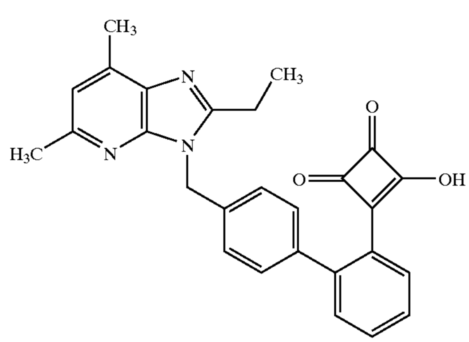 | WO #94/01436 pub. Jan. 20, 1994 |

TABLE II-continued

Angiotensin II Antagonists

| Compound # | Structure | Source |
|---|---|---|
| 316 | 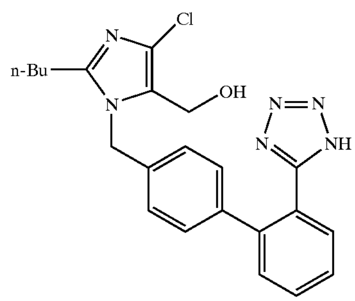 | EP #253,310 pub. Jan. 20, 1988 |
| 317 | 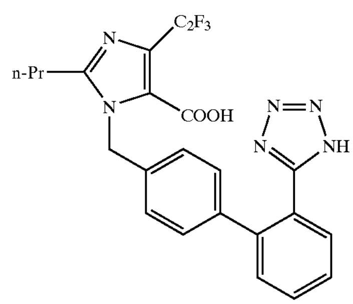 | EP #324,377 pub. Jul. 19, 1989 |
| 318 | 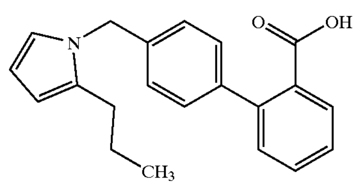 | U.S. Pat. No. 5,043,349 issued Aug. 27, 1991 |
| 319 | 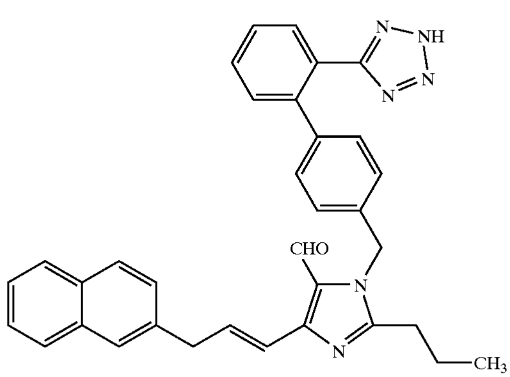 | WO #91/00281 pub. Jan. 10, 1991 |
| 320 | 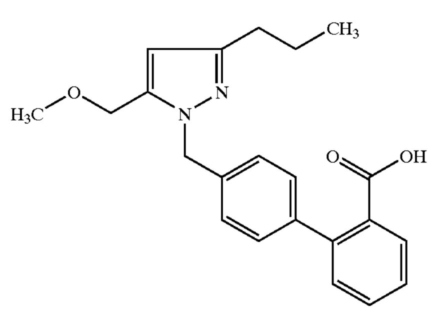 | U.S. Pat. No. 5,015,651 pub. May 14, 1991 |

TABLE II-continued
Angiotensin II Antagonists
| Compound # | Structure | Source |
|---|---|---|
| 321 | 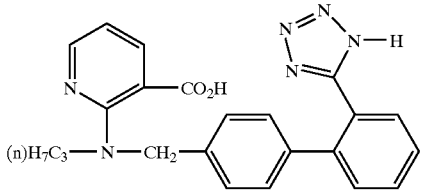 | |
| 322 | 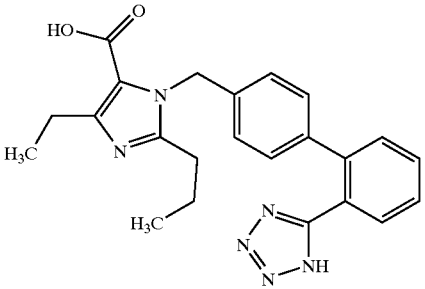 | WO #92/00977 pub. Jan. 23, 1992 |
| 323 | 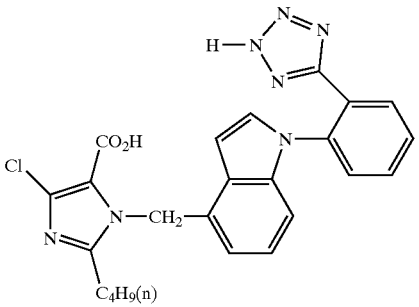 | |
| 324 | 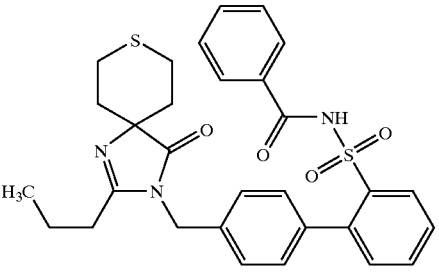 | WO #93/04046 pub. Mar. 4, 1993 |
| 325 | 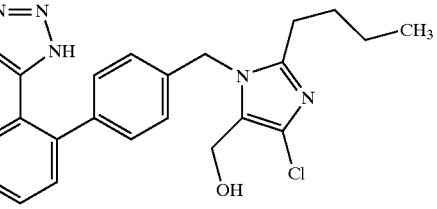 | WO #93/10106 pub. May 27, 1993 |

TABLE II-continued
Angiotensin II Antagonists
| Compound # | Structure | Source |
|---|---|---|
| 326 | 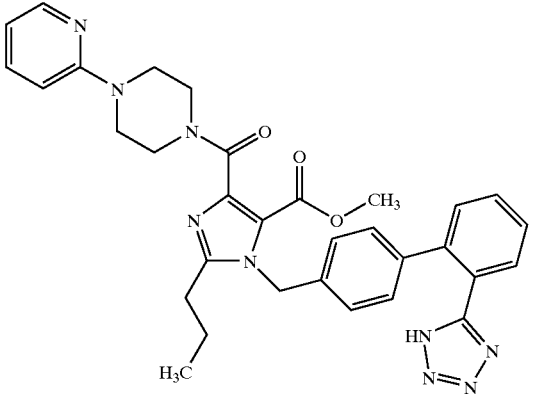 | U.S. Pat. No. 5,219,856<br>pub. Jun. 15, 1993 |
| 327 | 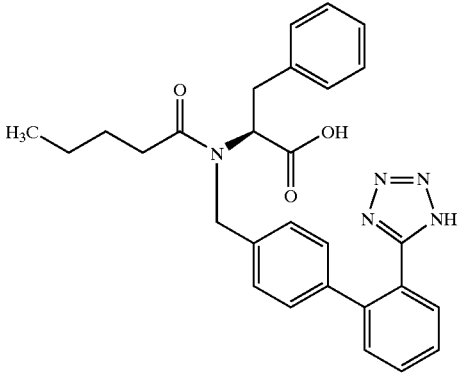 | U.S. Pat. No. 5,260,325<br>pub. Nov. 9, 1993 |
| 328 | 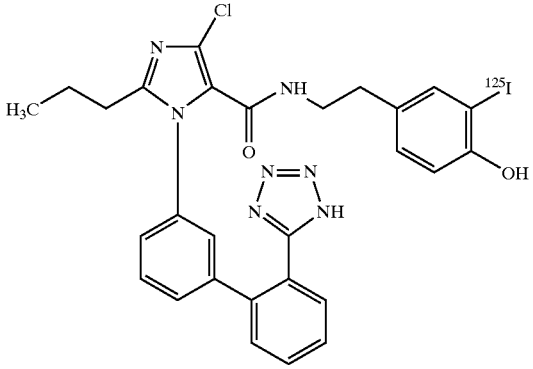 | U.S. Pat. No. 5,264,581<br>pub. Nov. 23 1993 |
| 329 | 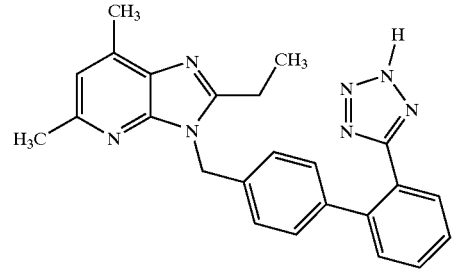 | EP #400,974<br>pub. Dec. 5, 1990 |

TABLE II-continued

Angiotensin II Antagonists

| Compound # | Structure | Source |
|---|---|---|
| 330 | | EP #411,766 pub. Feb. 6, 1991 |
| 331 | | EP #412,594 pub. Feb. 13, 1991 |
| 332 | | EP #419,048 pub. Mar. 27, 1991 |
| 333 | | WO #91/12,001 pub. Aug. 22, 1991 |

TABLE II-continued

Angiotensin II Antagonists

| Compound # | Structure | Source |
|---|---|---|
| 334 | 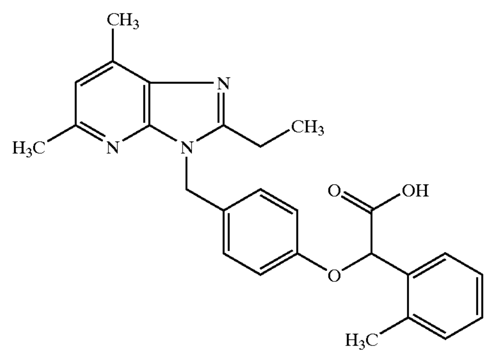 | WO #91/11,999 pub. Aug. 22, 1991 |
| 335 | 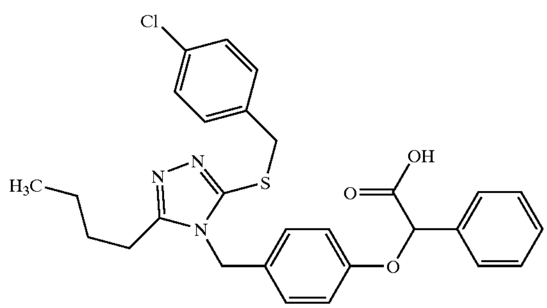 | WO #91/11,909 pub. Aug. 22, 1991 |
| 336 | 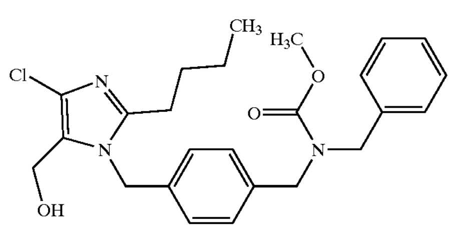 | WO #91/12,002 pub. Aug. 22, 1991 |
| 337 | 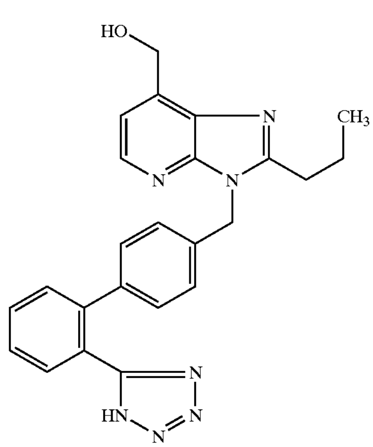 | U.S. Pat. No. 5,053,329 pub. Oct. 1, 1991 |

TABLE II-continued

Angiotensin II Antagonists

| Compound # | Structure | Source |
|---|---|---|
| 338 | 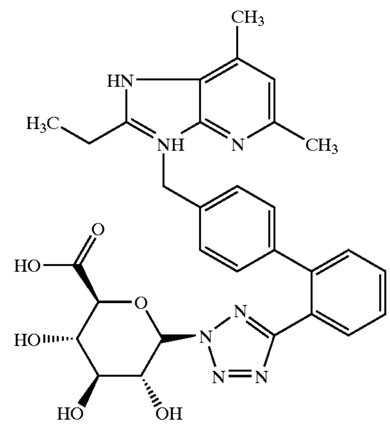 | U.S. Pat. No. 5,057,522 pub Oct. 15, 1991 |
| 339 | 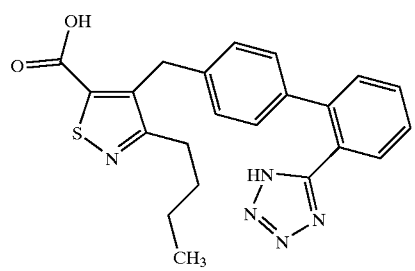 | WO #91/15,479 pub. Oct. 17, 1991 |
| 340 | 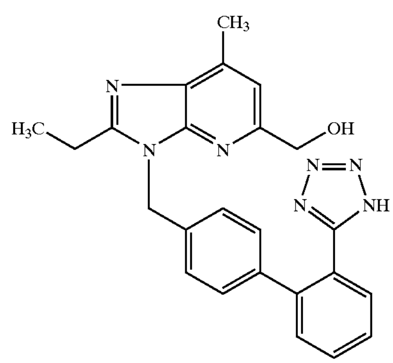 | EP #456,510 pub. Nov. 13, 1991 |
| 341 | 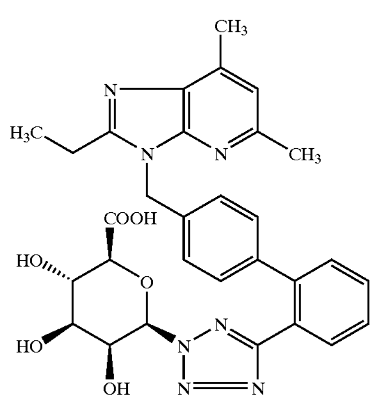 | EP #467,715 pub. Jan. 22, 1992 |

TABLE II-continued

Angiotensin II Antagonists

| Compound # | Structure | Source |
|---|---|---|
| 342 | 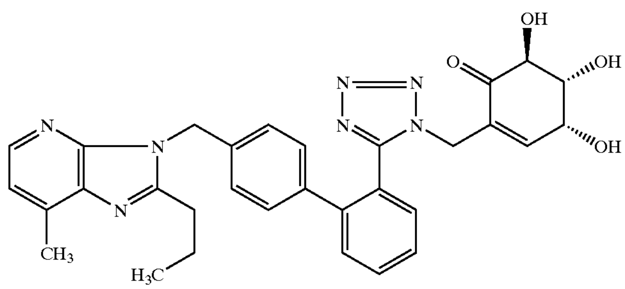 | U.S. Pat. No. 5,087,702 pub. Feb. 11, 1992 |
| 343 | 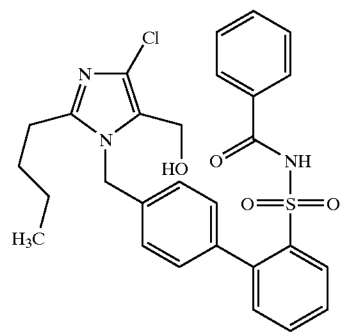 | EP #479,479 pub. Apr. 8, 1992 |
| 344 | 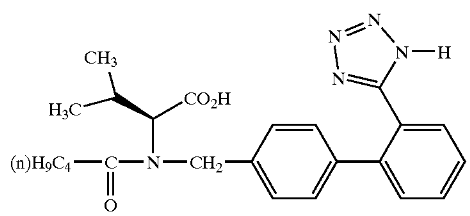 | |
| 345 | 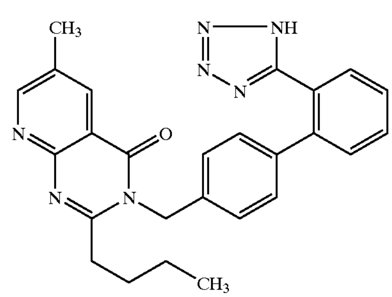 | EP #481,614 pub. Apr. 22, 1992 |
| 346 | 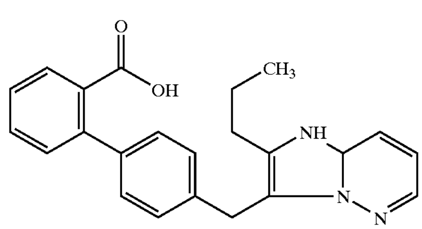 | EP #490,587 pub. Jun. 17, 1992 |

TABLE II-continued
Angiotensin II Antagonists
| Compound # | Structure | Source |
|---|---|---|
| 347 | 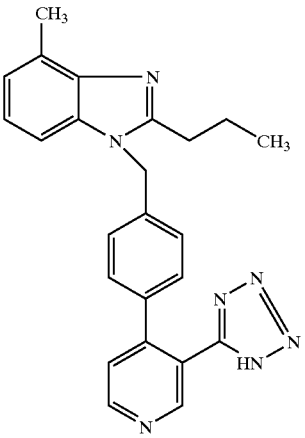 | U.S. Pat. No. 5,128,327 pub. Jul. 7, 1992 |
| 348 | 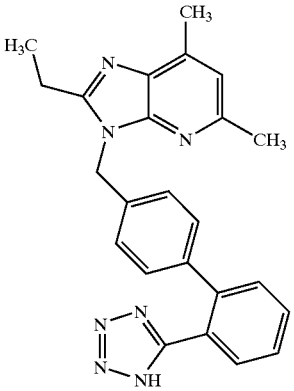 | U.S. Pat. No. 5,132,216 pub. Jul. 21, 1992 |
| 349 | 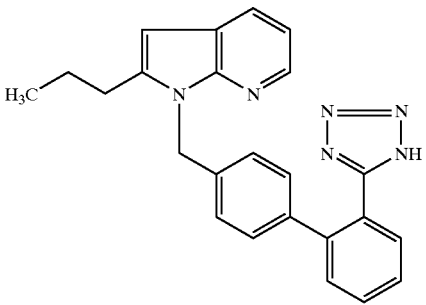 | EP #497,516 pub. Aug. 5, 1992 |

TABLE II-continued

Angiotensin II Antagonists

| Compound # | Structure | Source |
|---|---|---|
| 350 | 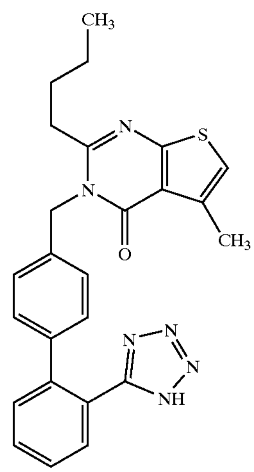 | EP #502,725 pub. Sep. 9, 1992 |
| 351 | 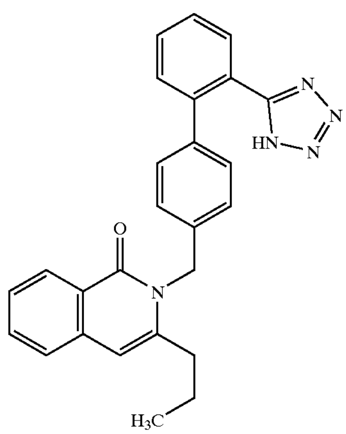 | EP #502,575 pub. Sep. 9, 1992 |
| 352 | 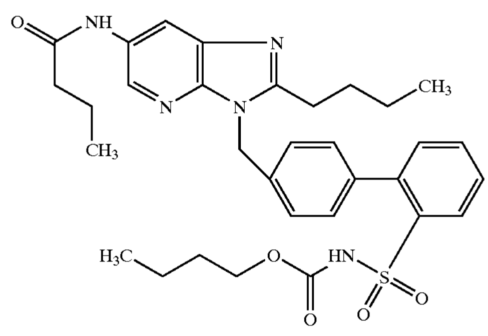 | EP #503,838 pub. Sep. 16, 1992 |

TABLE II-continued

Angiotensin II Antagonists

| Compound # | Structure | Source |
|---|---|---|
| 353 | 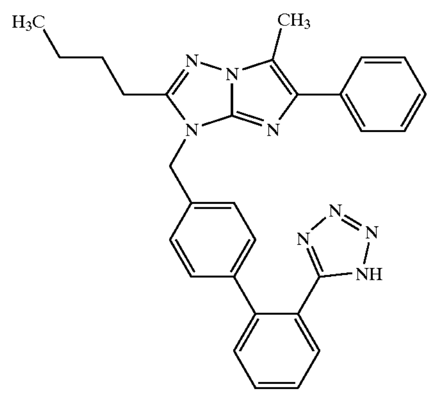 | EP #505,111<br>pub. Sep. 23, 1992 |
| 354 | 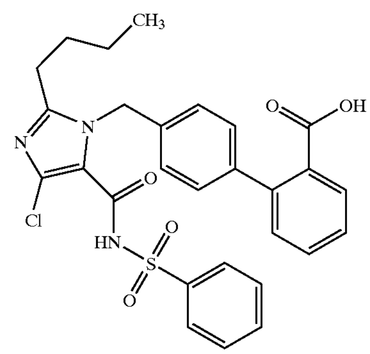 | EP #505,098<br>pub. Sep. 23, 1992 |
| 355 | 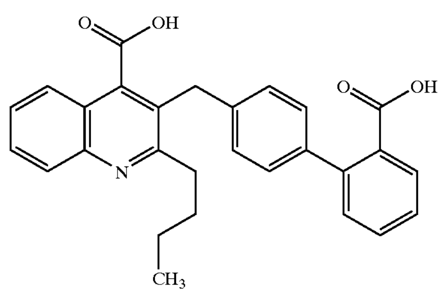 | EP #507,594<br>pub. Oct. 7, 1992 |
| 356 | 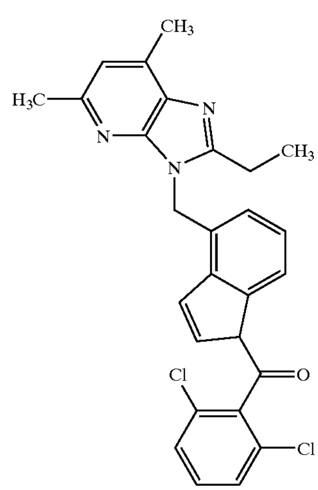 | EP #508,723<br>pub. Oct. 14, 1992 |

TABLE II-continued

Angiotensin II Antagonists

| Compound # | Structure | Source |
|---|---|---|
| 357 | 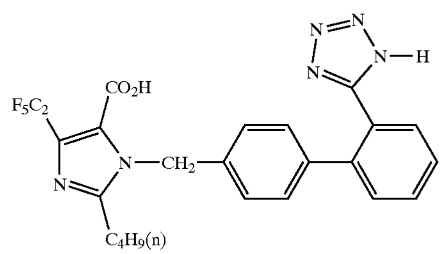 | |
| 358 | 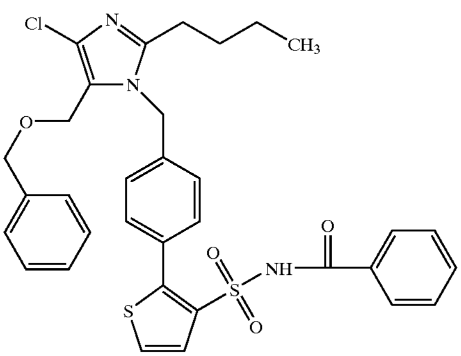 | EP #512,675<br>pub. Nov. 11, 1992 |
| 359 | 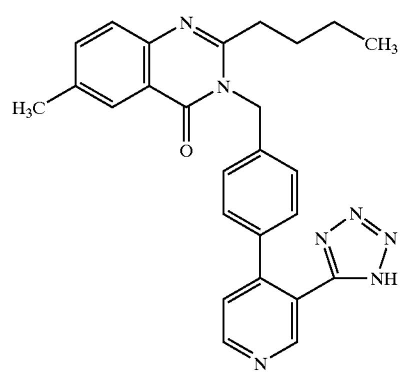 | EP #512,676<br>pub. Nov. 11, 1992 |
| 360 | 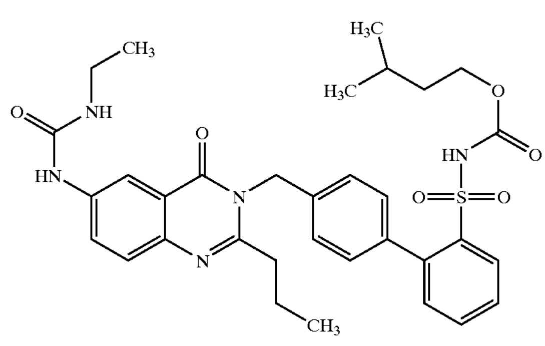 | EP #512,870<br>pub. Nov. 11, 1992 |

TABLE II-continued

Angiotensin II Antagonists

| Compound # | Structure | Source |
|---|---|---|
| 361 | 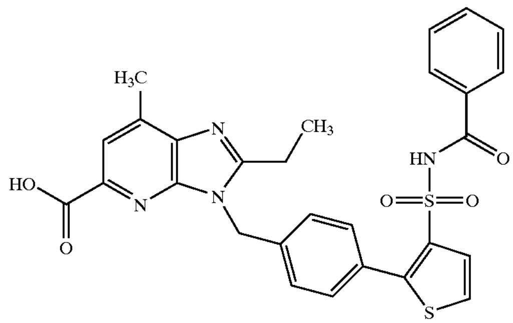 | EP #513,979<br>pub. Nov. 19, 1992 |
| 362 | 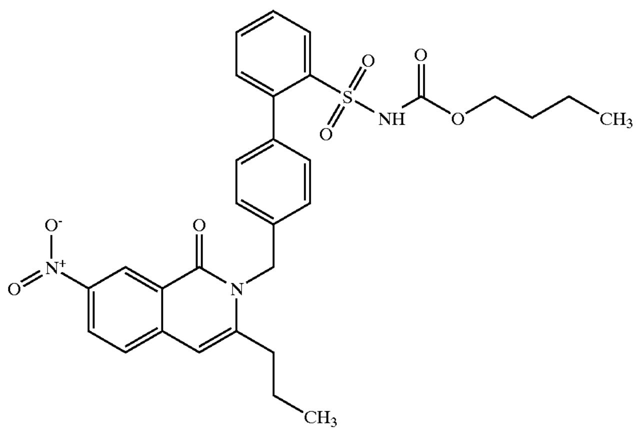 | WO #92/20,660<br>pub. Nov. 26, 1992 |
| 363 | 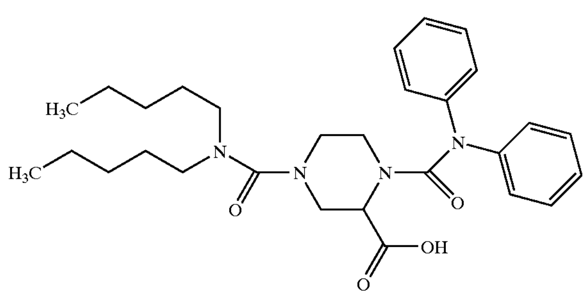 | WO #92,20,661<br>pub. Nov. 26, 1992 |
| 364 | 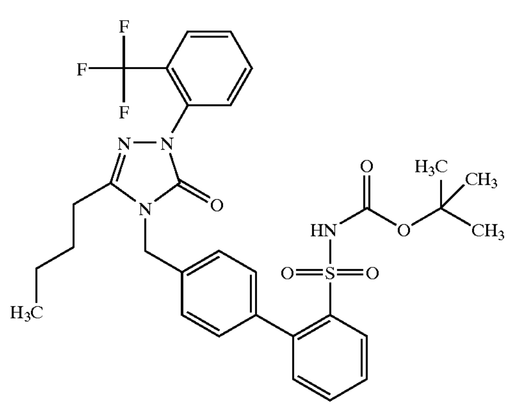 | WO #92/20,662<br>pub. Nov. 26, 1992 |

TABLE II-continued

Angiotensin II Antagonists

| Compound # | Structure | Source |
|---|---|---|
| 365 | 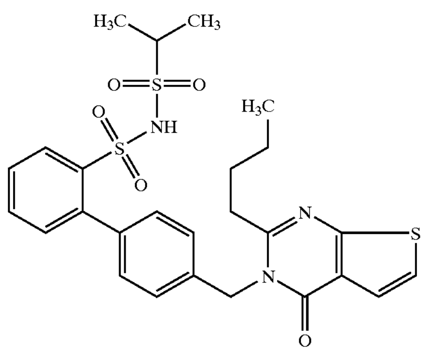 | WO #92/20,687<br>pub. Nov. 26, 1992 |
| 366 | 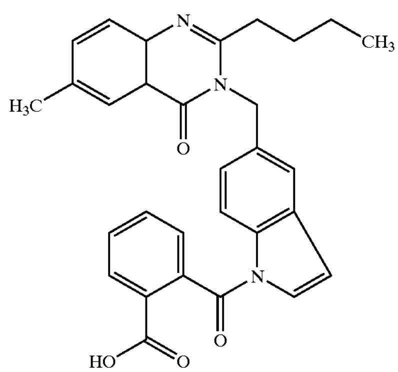 | EP #517,357<br>pub. Dec. 9, 1992 |
| 367 | 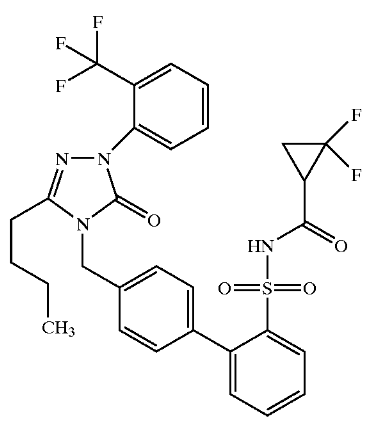 | WO #93/01177<br>pub. Jan. 21, 1993 |
| 368 | 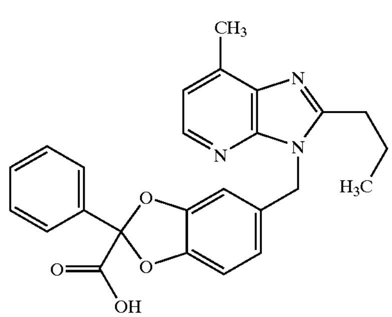 | U.S. Pat. No. 5,187,159<br>pub. Feb. 16, 1993 |

TABLE II-continued

Angiotensin II Antagonists

| Compound # | Structure | Source |
|---|---|---|
| 369 | 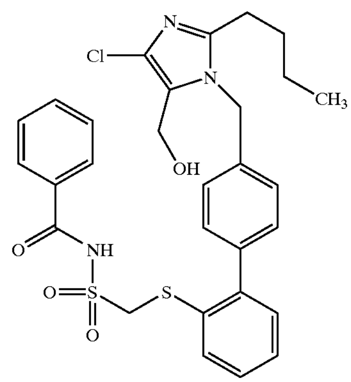 | U.S. Pat. No. 5,198,438<br>pub. Mar. 30, 1993 |
| 370 | 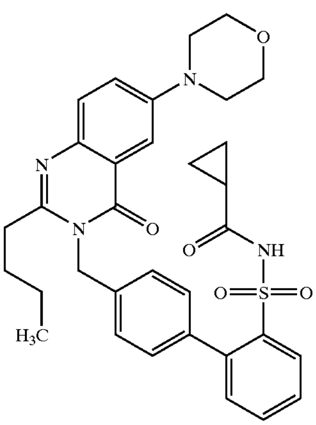 | U.S. Pat. No. 5,202,322<br>pub. Apr. 13, 1993 |
| 371 | 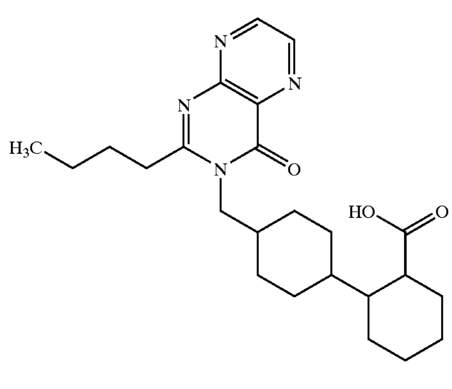 | EP #537,937<br>pub. Apr. 21, 1993 |

TABLE II-continued

Angiotensin II Antagonists

| Compound # | Structure | Source |
|---|---|---|
| 372 | 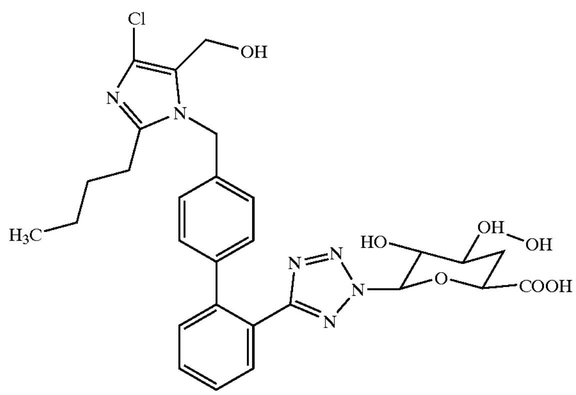 | U.S. Pat. No. 5,217,882 pub. Jun. 8, 1993 |
| 373 | 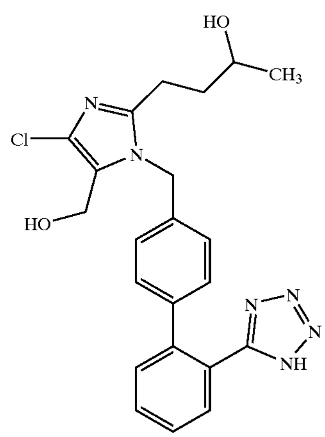 | U.S. Pat. No. 5,214,153 pub. May 25, 1993 |
| 374 | 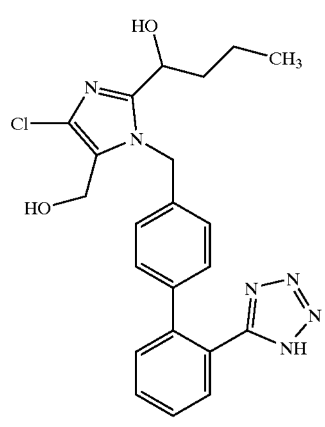 | U.S. Pat. No. 5,218,125 pub. Jun. 8, 1993 |

TABLE II-continued

Angiotensin II Antagonists

| Compound # | Structure | Source |
|---|---|---|
| 375 | 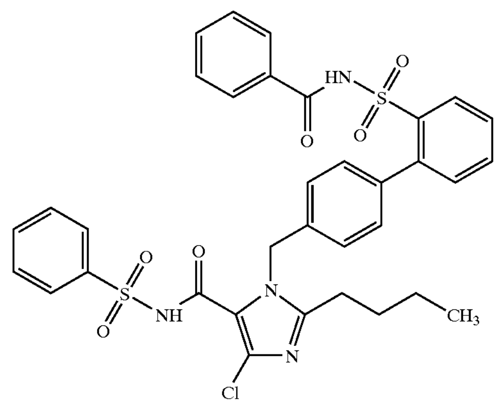 | U.S. Pat. No. 5,236,928 pub. Aug. 17, 1993 |
| 376 | 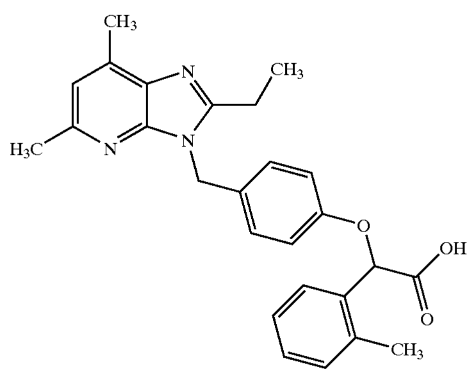 | U.S. Pat. No. 5,240,938 pub. Aug. 31, 1993 |
| 377 | 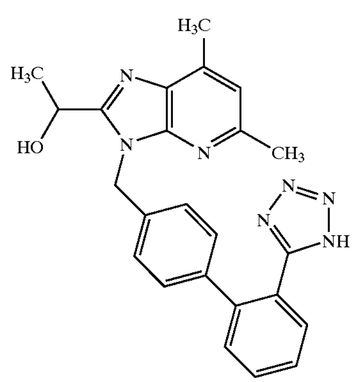 | GB #2,264,709 pub. Sep. 8, 1993 |
| 378 | 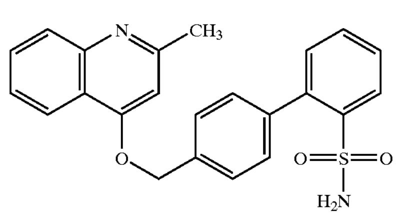 | GB #2,264,710 pub. Sep. 8, 1993 |

TABLE II-continued
Angiotensin II Antagonists
| Compound # | Structure | Source |
|---|---|---|
| 379 | 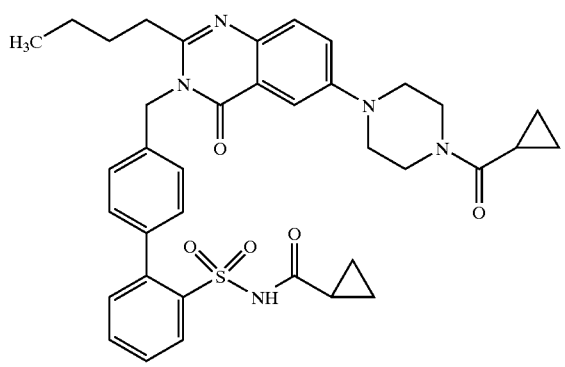 | U.S. Pat. No. 5,256,667<br>pub. Oct. 26, 1993 |
| 380 | 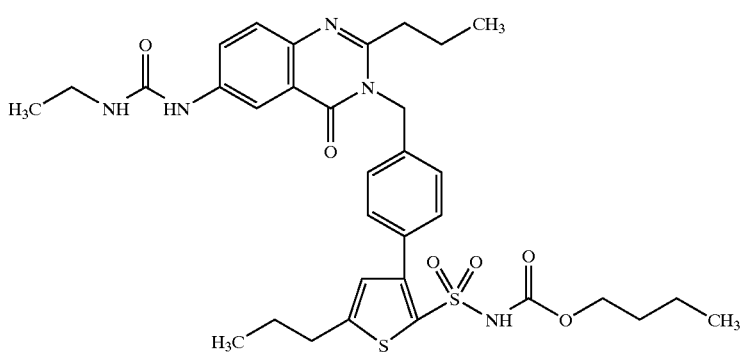 | U.S. Pat. No. 5,525,574<br>pub. Oct. 12, 1993 |
| 381 | 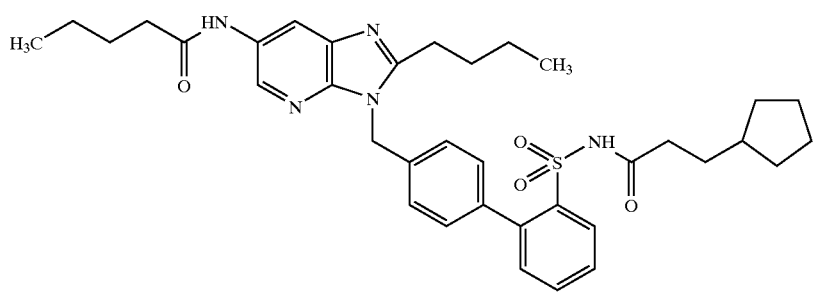 | WO #93/23,399<br>pub. Nov. 25, 1993 |
| 382 | 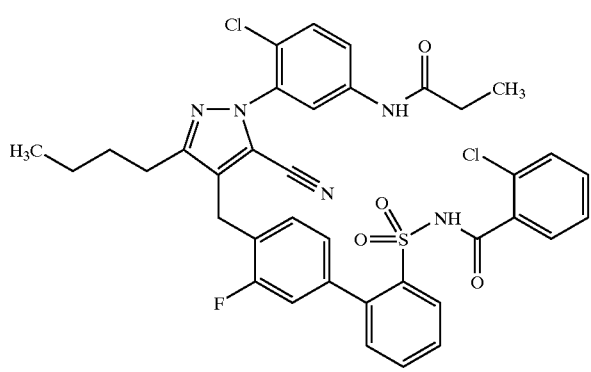 | U.S. Pat. No. 5,262,412<br>pub. Nov. 16, 1993 |

TABLE II-continued

Angiotensin II Antagonists

| Compound # | Structure | Source |
|---|---|---|
| 383 | 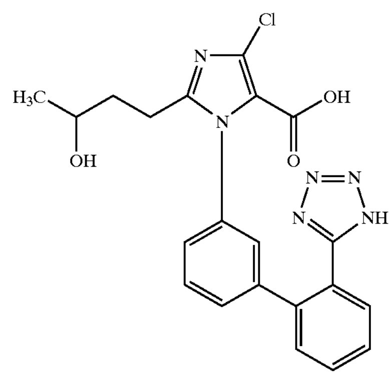 | U.S. Pat. No. 5,264,447 pub. Nov. 23, 1993 |
| 384 | 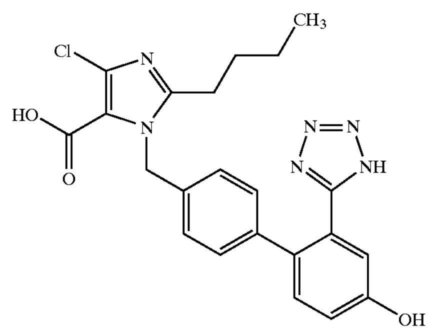 | U.S. Pat. No. 5,266,583 pub. Sep. 1, 1992 |
| 385 | 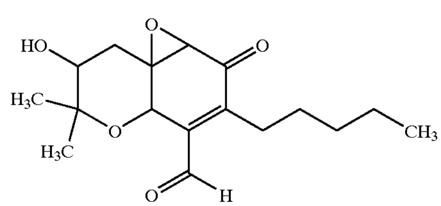 | U.S. Pat. No. 5,276,054 pub. Jan. 4, 1994 |
| 386 | 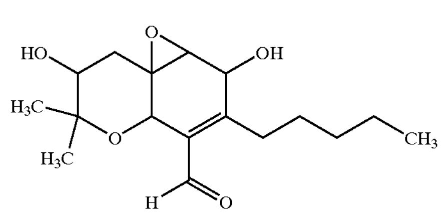 | U.S. Pat. No. 5,278,068 pub. Jan. 11, 1994 |

TABLE II-continued

Angiotensin II Antagonists

| Compound # | Structure | Source |
|---|---|---|
| 387 | 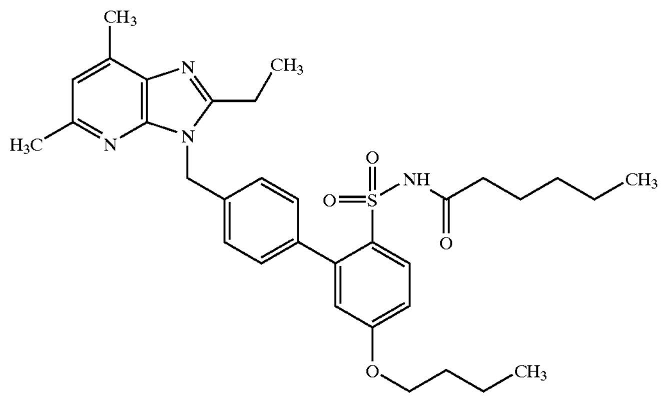 | WO #94/02142 pub. Feb. 3, 1994 |
| 388 | 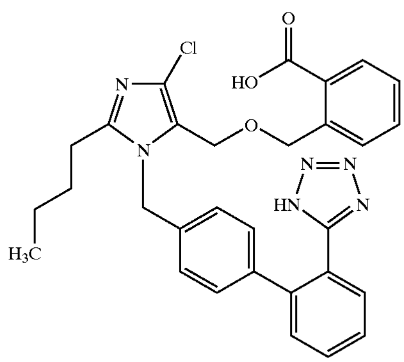 | WO #94/02467 pub. Feb. 3, 1994 |
| 389 | 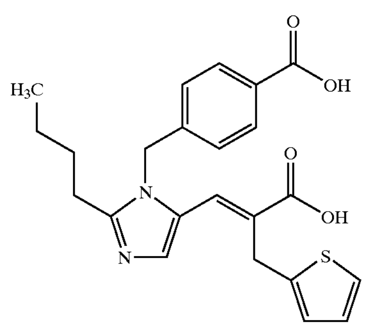 | EP #403,159 pub. Dec. 19, 1990 |
| 390 | 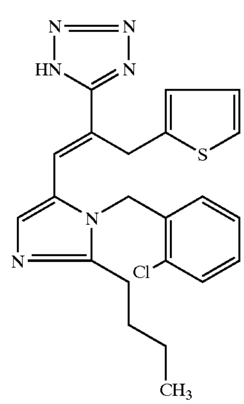 | EP #425,211 pub. May 2, 1991 |

TABLE II-continued

Angiotensin II Antagonists

| Compound # | Structure | Source |
|---|---|---|
| 391 | 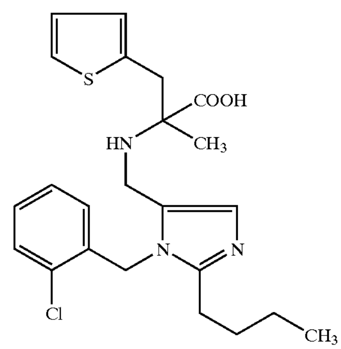 | EP #427,463<br>pub May 15, 1991 |
| 392 | 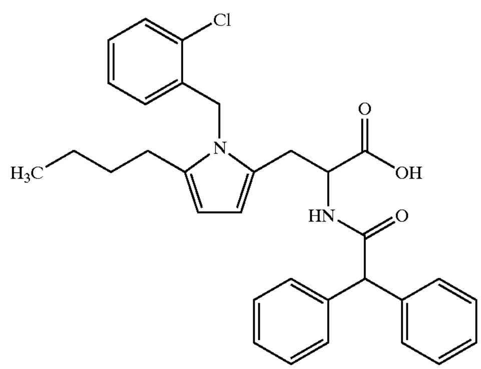 | WO #92/00068<br>pub. Jan. 9, 1992 |
| 393 | 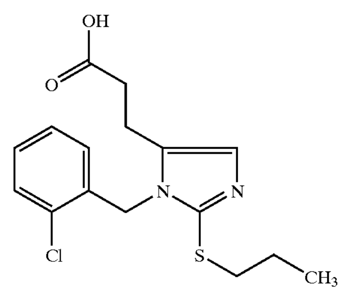 | WO #92/02,510<br>pub. Feb. 20, 1992 |
| 394 | 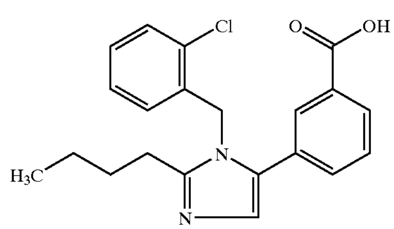 | WO #92/09278<br>pub. Jun. 11, 1992 |
| 395 | 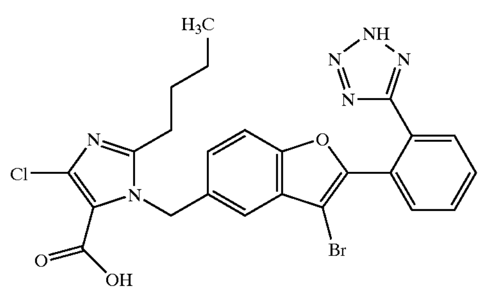 | WO #92/10181<br>pub. Jun. 25, 1992 |

TABLE II-continued

Angiotensin II Antagonists

| Compound # | Structure | Source |
|---|---|---|
| 396 | 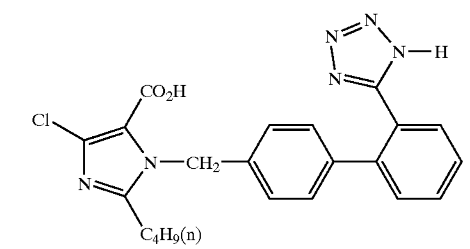 | |
| 397 | 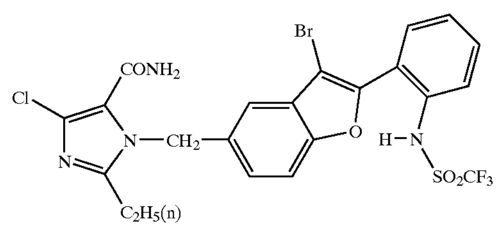 | |
| 398 | 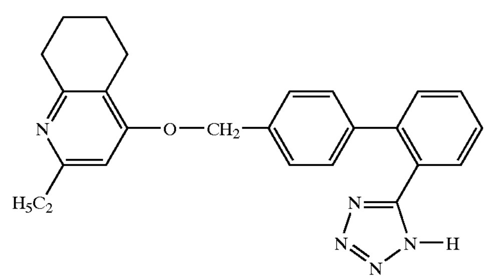 | |
| 399 | 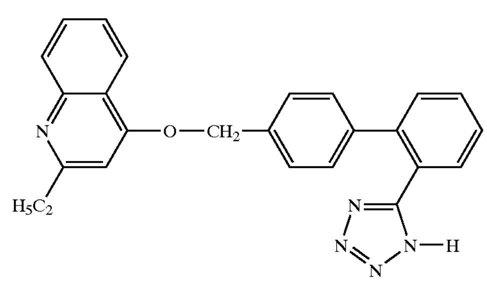 | |
| 400 | 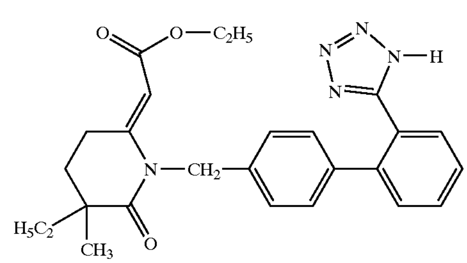 | |

TABLE II-continued

Angiotensin II Antagonists

| Compound # | Structure | Source |
|---|---|---|
| 401 | 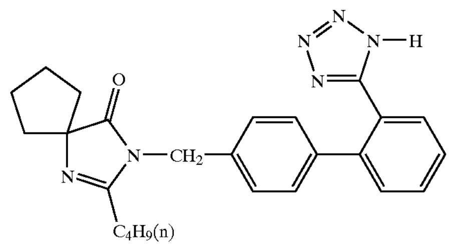 | |
| 402 | 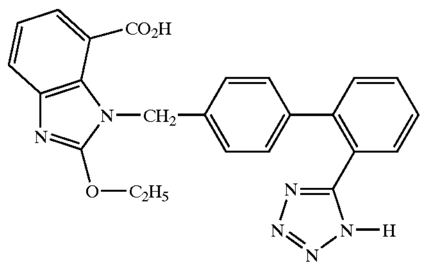 | |
| 403 | 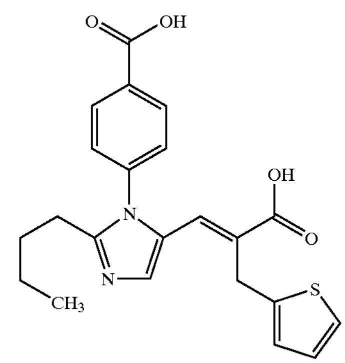 | WO #92/10097 pub. Jun. 25, 1992 |
| 404 | 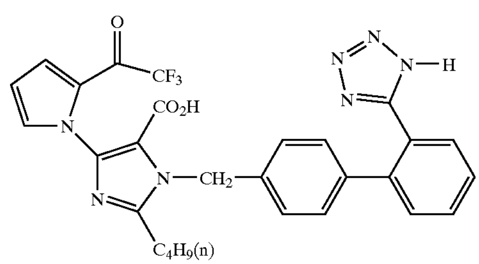 | |
| 405 | 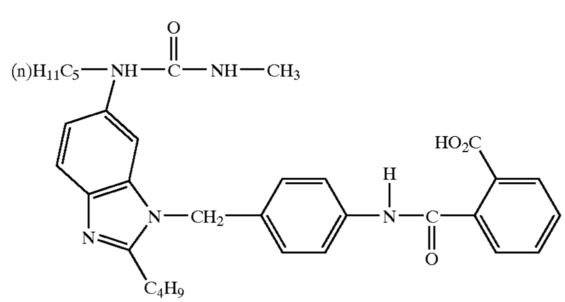 | |

TABLE II-continued

Angiotensin II Antagonists

| Compound # | Structure | Source |
|---|---|---|
| 406 | 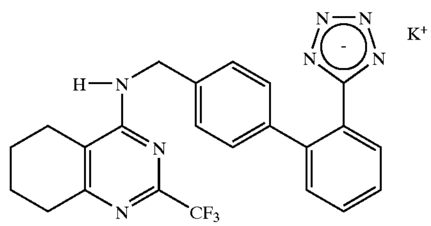 | |
| 407 | 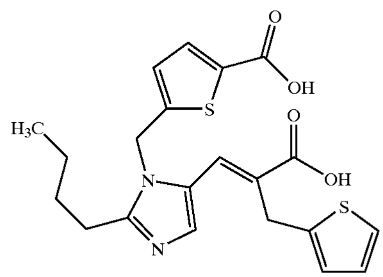 | WO #92/20651 pub. Nov. 26, 1992 |
| 408 | 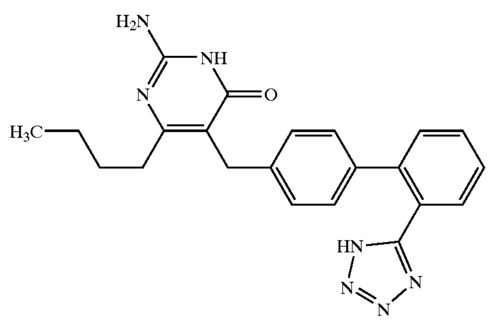 | WO #93/03018 pub. Feb. 18, 1993 |
| 409 | 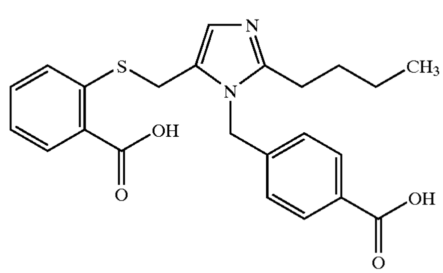 | WO #94/00120 pub. Jan. 6, 1994 |
| 410 | 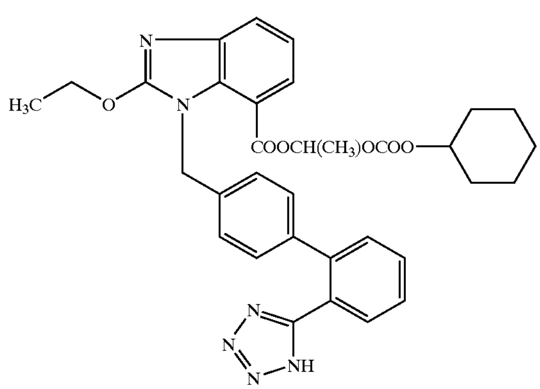 | EP #459,136 pub. Dec. 4, 1991 |

TABLE II-continued
Angiotensin II Antagonists
| Compound # | Structure | Source |
|---|---|---|
| 411 | 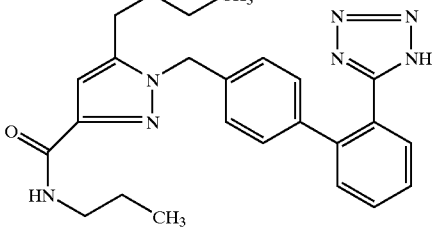 | EP #411,507<br>pub. Feb. 5, 1991 |
| 412 | 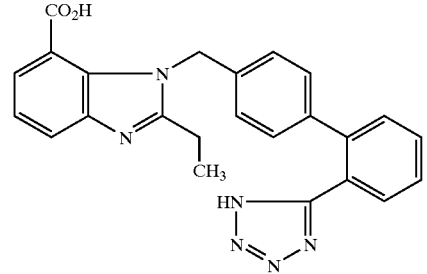 | EP #425,921<br>pub. May 8, 1991 |
| 413 | 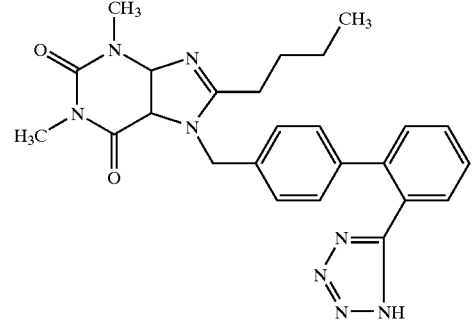 | EP #430,300<br>pub. Jun. 5, 1991 |
| 414 | 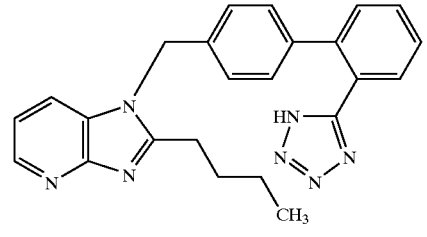 | EP #434,038<br>pub. Jun. 26, 1991 |
| 415 | 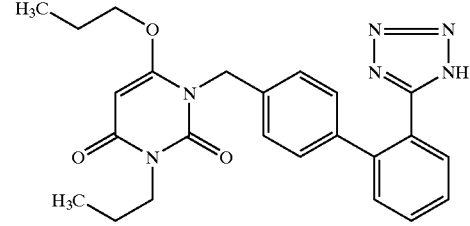 | EP #442,473<br>pub. Aug. 21, 1991 |

TABLE II-continued

Angiotensin II Antagonists

| Compound # | Structure | Source |
|---|---|---|
| 416 | 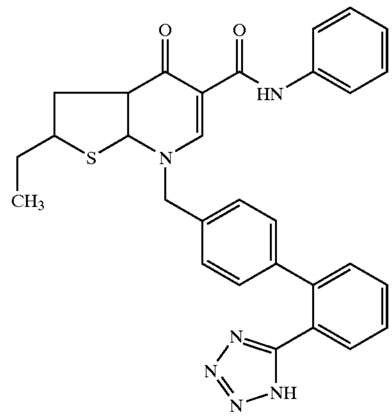 | EP #443,568 pub. Aug. 28, 1991 |
| 417 | 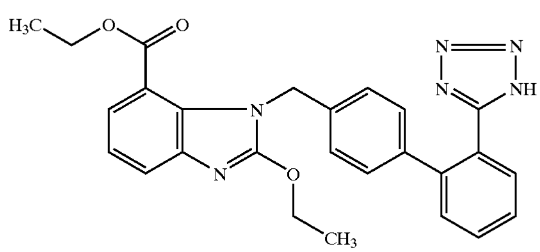 | EP #459,136 pub. Dec. 4, 1991 |
| 418 | 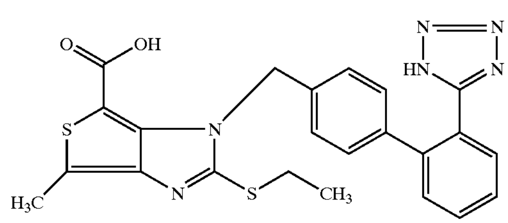 | EP #483,683 pub. May 5, 1992 |
| 419 | 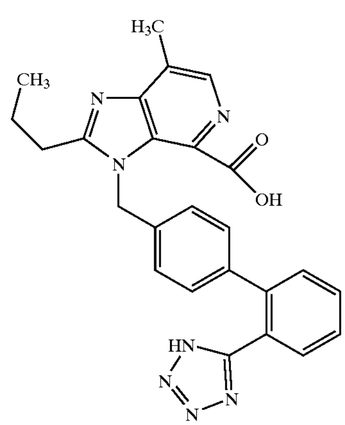 | EP #518,033 pub. Dec. 16, 1992 |

TABLE II-continued

Angiotensin II Antagonists

| Compound # | Structure | Source |
|---|---|---|
| 420 | 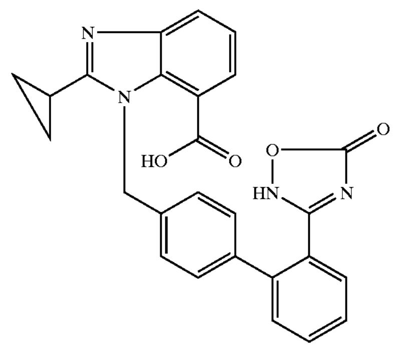 | EP #520,423 pub. Dec. 30, 1992 |
| 421 | 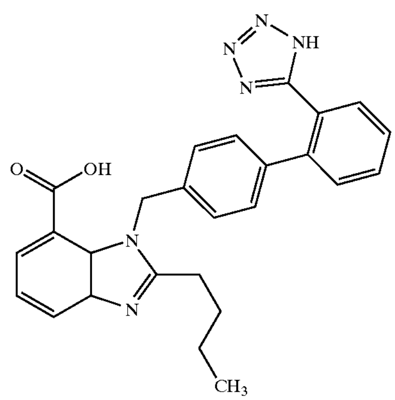 | EP #546,358 pub. Jun. 16, 1993 |
| 422 | 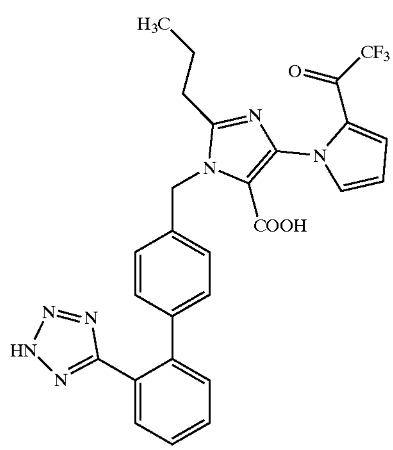 | WO #93/00341 pub. Jan. 7, 1993 |
| 423 | 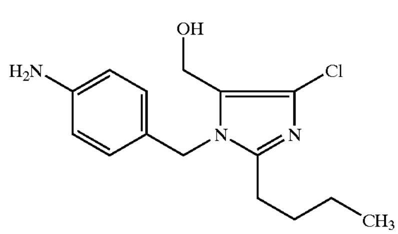 | WO #92/06081 pub. Apr. 16, 1992 |

TABLE II-continued

Angiotensin II Antagonists

| Compound # | Structure | Source |
|---|---|---|
| 424 | 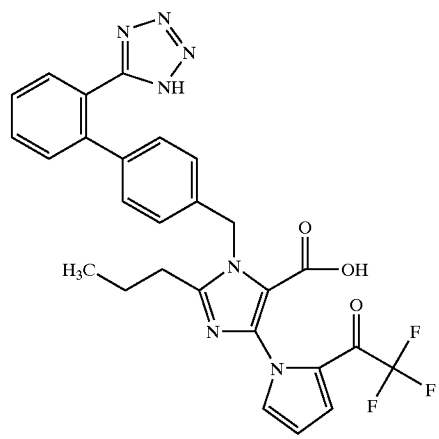 | WO #93/00341 pub. Jan. 7, 1993 |
| 425 | 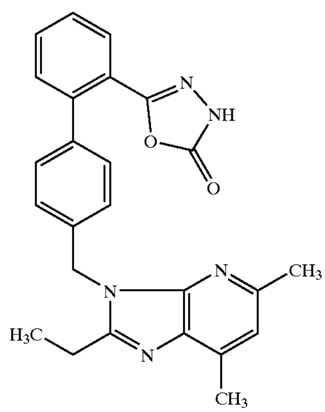 | U.S. Pat. No. 5,210,204 pub. May 11, 1993 |
| 426 | 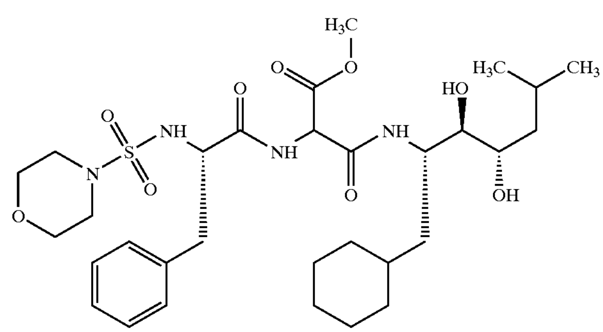 | EP #343,654 pub. Nov. 28, 1989 |
| 427 | 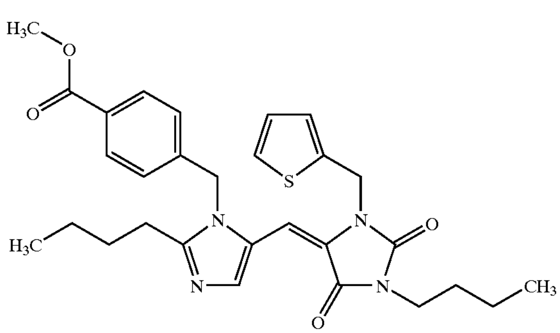 | WO #93/13077 pub. Jul. 8, 1993 |

TABLE II-continued

Angiotensin II Antagonists

| Compound # | Structure | Source |
|---|---|---|
| 428 | 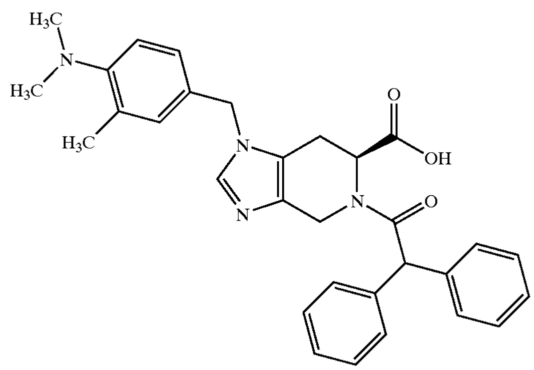 | WO #93/15734 pub. Aug. 19, 1993 |
| 429 | 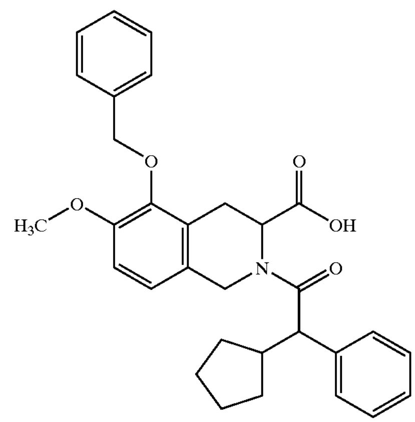 | U.S. Pat. No. 5,246,943 pub. Sep. 21, 1993 |

The term "hydrido" denotes a single hydrogen atom (H). This hydrido group may be attached, for example, to an oxygen atom to form a hydroxyl group; or, as another example, one hydrido group may be attached to a carbon atom to form a

group, or, as another example, two hydrido atoms may be attached to a carbon atom to form a —$CH_2$— group. Where the term "alkyl" is used, either alone or within other terms such as "haloalkyl" and "hydroxylalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty-carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons.

The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "alkyl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "phenalkyl" and "phenylalkyl" are interchangeable. An example of "phenalkyl" is "phenethyl" which is interchangeable with "phenylethyl". The terms "alkylaryl", "alkoxyaryl" and "haloaryl" denote, respectively, the substitution of one or more "alkyl", "alkoxy" and "halo" groups, respectively, substituted on an "aryl" nucleus, such as a phenyl moiety. The terms "aryloxy" and "arylthio" denote radicals respectively, provided by aryl groups having an oxygen or sulfur atom through which the radical is attached to a nucleus, examples of which are phenoxy and phenylthio. The terms "sulfinyl" and "sulfonyl", whether used alone or linked to other terms, denotes, respectively, divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The term "monoalkylaminocarbonyl" is interchangeable with "N-alkylamido". The term "dialkylaminocarbonyl" is interchangeable with "N,N-dialkylamio". The term "alkenylalkyl" denotes a radical having a double-bond unsaturation site between two carbons, and which radical may consist of only two carbons or may be further substituted with alkyl groups which may optionally contain additional double-bond unsaturated. The term "heteroaryl", where not otherwised defined before, embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. The any of the foregoing defined radicals, preferred radicals are those containing from one to about ten carbon atoms.

Specific examples of alkyl groups are methyl, ethyl, n propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the combination of the invention are the isomeric forms of the above-described angiotensin II receptor compounds and the epoxy-steroidal aldosterone receptor compounds, including diastereoisomers, regiosomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonc (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with such compound.

BIOLOGICAL EVALUATION

In order to determine the probable effectiveness of a combination therapy for treating or preventing the progression of cardiofibrosis or cardiac hypertrophy, it is important to determine the potency of individual components of the combination therapy. Accordingly, in Assays "A" through "C", the angiotensin II receptor antagonist profiles were determined for many of the compounds described in Table II, herein. In Assay "D", there is described a method for evaluating a combination therapy of the invention, namely, an angiotensin II receptor antagonist of Table II and an epoxy-steroidal aldosterone receptor antagonist of Table I. The efficacy of each of the individual drugs, epoxymexrenone and the angiotensin II receptor blocker, and of these drugs given together at various doses, is evaluated in a rodent model. The methods and results of such assays are described below.

Assay A: Antiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al (*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were changed with 0.25 ml of a solution containing 5 mM $MgCl_2$, 2 mM EDTA, 0.5% bovine serum albumin, 50 mM Tris-HCl, pH 7.5 and $^{125}$I-AII (approximately $10^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 $\mu$M of unlabelled AII. Specific binding was calculated as total binding minus nonspecific binding. The receptor binding affinity of an AII antagonist compound was indicated by the concentration ($IC_{50}$) of the tested AII antagonist which give 50% displacement of the total specifically bound $^{125}$I-AII from the angiotensin II $AT_1$ receptor. Binding data were analyzed by a nonlinear least-squares curve fitting program. Results are reported in Table III.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM); 130 NaCl, 15 $NaHCO_3$, 15 KCl, 1.2 $NaH_2PO_4$, 1.2 $MgSO_4$, 2.5 $CaCl_2$, and 11.4 glucose. The preparations were equilibrated for one hour before approximately one gram of passive tension was placed on the rings. Angiotensin II concentration-response curves were then recorded ($3\times10^{-10}$ to $1\times10^{-5}$ M). Each concentration of AII was allowed to elicit its maximal contraction, and then AII was washed out repeatedly for 30 minutes before rechallenging with a higher concentration of AII. Aorta rings were exposed to the test antagonist at $10^{-5}$ M for 5 minutes before challenging with AII. Adjacent segments of the same aorta ring were used for all concentration-response curves in the presence of absence of the test antagonist. The effectiveness of the test compound was expressed in terms of $pA_2$ values and were calculated according to H. O. Schild [*Br. J. Pharmacol. Chemother.*, 2, 189–206 (1947)]. The $pA_2$ value is the concentration of the antagonist which increases the $EC_{50}$ value for AII by a factor of two. Each test antagonist was evaluated in aorta rings from two rabbits. Results are reported in Table III.

Assay C: In Vivo Intragastric Pressor Assay Response for All Antagonists

Male Sprague-Dawley rats weighing 225–300 grams were anesthetized with methohexital (30 mg/kg, i.p.) and catheters were implanted into the femoral artery and vein. The catheters were tunneled subcutaneously to exit dorsally, posterior to the head and between the scapulae. The catheters were filled with heparin (1000 units/ml of saline). The rats were returned to their cage and allowed regular rate chow and water *ad libitum*. After full recovery from surgery (3–4 days), rats were placed in Lucite holders and the arterial line was connected to a pressure transducer. Arterial pressure was recorded on a Gould polygraph (mmHg). Angiotensin II was administered as a 30 ng/kg bolus via the venous catheter delivered in a 50 $\mu$l volume with a 0.1 ml saline flush. The pressor response in mm Hg was measured by the difference from pre-injection arterial pressure to the maximum pressure achieved. The AII injection was repeated every 10 minutes until three consecutive injections yielded responses within 4 mmHg of each other. These three responses were then averaged and represented the control response to AII. The test compound was suspended in 0.5% methylcellulose in water and was administered by gavage. The volume administered was 2 ml/kg body weight. The standard dose was 3 mg/kg. Angiotensin II bolus injections were given at 30, 45, 60, 75, 120, 150, and 180 minutes after gavage. The pressor response to AII was measured at each time point. The rats were then returned to their cage for future testing. A minimum of 3 days was allowed between tests. Percent inhibition was calculated for each time point following gavage by the following formula: [(Control Response—Response at time point)/Control Response]× 100. Results are shown in Table III.

Assay "D": Renal Hypertensive Rat Model

A combination therapy of an angiotensin II receptor antagonist and an epoxy-steroidal aldosterone receptor antagonist may be evaluated for blood pressure lowering activity in the renal-artery ligated hypertensive rat, a model of high renin hypertension. In this model, six days after ligation of the left renal artery, both plasma renin activity and blood pressure are elevated significantly [J. L. Cangiano et al., *J. Pharmacol. Exp. Ther.*, 206, 310–313 (1979)]. Male Sprague-Dawley rats are instrumented with a radiotelemetry blood pressure transmitter for continuous monitoring of blood pressure. The rats are anesthetized with a mixture of ketamine-HCl (100 mg/kg) and acepromazine maleate (2.2 mg/kg). The abdominal aorta is exposed via a midline incision. Microvascular clamps are placed on the aorta distal to the renal arteries and at the iliac bifurcation. The aorta is punctured with a 22-guage needle and the tip of a catheter is introduced. The catheter, which is held in place by a ligature in the psoas muscle, is connected to a radiotelemetry blood pressure transmitter (Mini-Mitter Co., Inc., Sunriver, Oreg.). The transmitter is placed in the peritoneal cavity and sutured to abdominal muscle upon closing of the incision. Rats are housed singly above a radiotelemetry receiver and are allowed standard rat chow and water *ad libitum*. At least 5 days are allowed for recovery from surgery. Mean arterial pressure and heart rate are measured on a Compaq DeskPro 286 AT computer. Data are sampled for 10 seconds at 200–500 hz at 2.5 to 10 min intervals 24 hours per day. After collecting control data for 24 hours, the rats are anesthetized with methohexital (30 mg/kg, i.p.) and supplemented as needed. A midline abdominal incision is made, approximately 2 cm in length to expose the left kidney. The renal artery is separated from the vein near the aorta, with care taken not to traumatize the vein. The artery is completely ligated with sterile 4-O silk. The incision is closed by careful suturing of the muscle layer and skin. Six days later, when MAP is typically elevated by 50–70 mmHg, an AII receptor antagonist: or an aldosterone receptor antagonist, or a combination of the two compounds are administered by gavage each day for about 8 weeks. Single drug dosing is carried out using 20 and 200 mg/kg/day of epoxymexrenone and 1,3, 10,30 and 100 mg/kg/day of an AII receptor antagonist. Drug mixtures are obtained by administering a combination of a dose of 1,3,10,30 or 100 mg/kg/day of the AII receptor antagonist with a dose of either 20 or 200 mg/kg/day of the aldosterone antagonist. Blood pressure lowering is monitored by the radiotelemetry system and responses with the compounds are compared to responses obtained in vehicle-treated animals. Plasma and urinary sodium and potassium levels are monitored as a measure of the effectiveness of the aldosterone blockade. Urine samples are collected overnight using metabolic cages to isolate the samples. Plasma samples are obtained by venous catheterization. Sodium and potassium are measured by flame photometry. Cardiac fibrosis is determined by histological and chemical measurements of the excised hearts following perfusion fixation. Left and right ventricles are weighed, embedded and sectioned. Subsequently, sections are stained with picrosirius red and the red staining collagen areas are quantitated by computerized image analysis. The apex of the heart is acid digested and the free hydroxyproline measured colorimetrically. It is expected that MAP will be significantly lowered toward normal pressures in the test animals, treated with the combination therapy and that the condition of myocardial fibrosis will be arrested or avoided.

TABLE III

In Vivo and In Vitro Angiotensin II Activity of Compounds of the Invention

| Test Compound Example # | [1]Assay A $IC_{50}$ (nM) | [2]Assay B $pA_2$ | [3]Assay C Dose (mg/kg) | Inhibition (%) | Duration (min.) |
|---|---|---|---|---|---|
| 1 | NT | NT | NT | NT | NT |
| 2 | 95 | 7.37/7.59 | 10 | 95 | 60 |
|  |  |  | 30 | 98 | 90–120 |
| 3 | 5.4 | 8.70 ± 0.2 | 10 | 50 | >180 |
|  |  |  | 30 | 100 | 200+ |
| 4 | NT | NT | NT | NT | NT |
| 5 | 200 | 7.48/6.91 | 30 | 38 | 20–30 |
| 6 | 1300 | 6.55/6.82 | 100 | 90 | 120 |
| 7 | 84 | 8.01/8.05 | 30 | 90 | 130 |
| 8 | 17,000 | NT | NT | NT | NT |
| 9 | 700 | 6.67/6.12 | 30 | 80 | 75 |
|  |  |  | 100 | 100 | 130 |
| 10 | 4.9 | 8.19/7.59 | 3 | 86 | 100 |
|  |  |  | 30 | 100 | 240 |
| 11 | 160 | 6.45/6.77 | NT | NT | NT |
| 12 | 6.0 | 8.66/8.59 | NT | NT | NT |
| 13 | 17 | 8.70/8.85 | NT | NT | NT |
| 14 | 7.2 | 8.84/8.71 | NT | NT | NT |
| 15 | 16 | 8.31/8.30 | NT | NT | NT |
| 16 | 6.4 | 8.95/9.24 | NT | NT | NT |
| 17 | 4.0 | 8.64/8.40 | NT | NT | NT |
| 18 | 970 | 6.14/6.09 | NT | NT | NT |
| 19 | 12,000 | 5.18/5.35 | NT | NT | NT |
| 20 | 78,000 | 5.89/5.99 | 100 | 10 | 45 |
| 21 | 87 | 7.71.7.21 | NT | NT | NT |
| 22 | 460 | 6.60/6.46 | NT | NT | NT |
| 23 | 430 | 6.48/7.15 | NT | NT | NT |
| 24 | 10 | 7.56/7.73 | NT | NT | NT |
| 25 | 480 | 6.80/6.73 | NT | NT | NT |
| 26 | 3.2 | 9.83/9.66 | 10 | 50 | >180 |
| 27 | 180 | NT | NT | NT | NT |
| 28 | 570 | 5.57/6.00 | NT | NT | NT |
| 29 | 160 | NT | NT | NT | NT |
| 30 | 22 | 7.73/7.88 | 30 | 50 | >180 |
| 31 | 14 | NT | NT | NT | NT |
| 32 | 16 | 7.68/7.29 | NT | NT | NT |
| 33 | 630 | 6.73/6.36 | NT | NT | NT |
| 34 | 640 | 5.34/5.69 | NT | NT | NT |
| 35 | 41 | 7.25/7.47 | NT | NT | NT |
| 36 | 1400 | 5.92/5.68 | NT | NT | NT |
| 37 | 340 | 6.90/6.85 | NT | NT | NT |
| 38 | 10 | 7.82/8.36 | NT | NT | NT |
| 39 | 10 | 7.88/7.84 | NT | NT | NT |
| 40 | 83 | 7.94/7.61 | NT | NT | NT |
| 41 | 3700 | 5.68/5.96 | NT | NT | NT |
| 42 | 370 | 6.56/6.26 | NT | NT | NT |
| 43 | 19 | 8.97/8.61 | NT | NT | NT |
| 44 | 16 | 8.23/7.70 | NT | NT | NT |
| 45 | 4.4 | 8.41/8.24 | NT | NT | NT |
| 46 | 110 | 6.80/6.64 | NT | NT | NT |
| 47 | 21 | 7.85/7.58 | NT | NT | NT |
| 48 | 680 | 6.27/6.75 | NT | NT | NT |
| 49 | 120 | 7.06/7.67 | NT | NT | NT |
| 50 | 54 | 7.71/7.89 | NT | NT | NT |
| 51 | 8.7 | 8.39/8.51 | NT | NT | NT |
| 52 | 100 | 8.14/8.12 | NT | NT | NT |
| 53 | 65 | 7.56/7.83 | NT | NT | NT |
| 54 | 3100 | 6.02 | NT | NT | NT |
| 55 | 80 | 6.56/7.13 | NT | NT | NT |
| 56 | 5.0 | 9.04/8.35 | NT | NT | NT |
| 57 | 2300 | 6.00 | NT | NT | NT |
| 58 | 140 | 6.45/6.57 | NT | NT | NT |
| 59 | 120 | 7.23/7.59 | NT | NT | NT |
| 60 | 2200 | 6.40/6.03 | NT | NT | NT |
| 61 | 110 | 7.29/7.70 | NT | NT | NT |
| 62 | 26 | 8.69/8.61 | NT | NT | NT |
| 63 | 61 | 7.77/7.67 | NT | NT | NT |
| 64 | 54 | 7.00/6.77 | NT | NT | NT |
| 65 | 23 | 7.85/7.75 | NT | NT | NT |
| 66 | 12 | 9.34/8.58 | NT | NT | NT |
| 67 | 3100 | 5.88/5.78 | NT | NT | NT |
| 68 | 8.6 | 8.19/8.65 | NT | NT | NT |
| 69 | 15 | 7.80/8.28 | NT | NT | NT |
| 70 | 44 | 7.71/8.05 | NT | NT | NT |
| 71 | 12,000 | * | NT | NT | NT |
| 72 | 83 | 6.11/6.10 | NT | NT | NT |
| 73 | 790 | 7.65/7.46 | NT | NT | NT |
| 74 | 6.5 | 8.56/8.39 | NT | NT | NT |
| 75 | 570 | 6.00/5.45 | NT | NT | NT |
| 76 | 5400 | 5.52/5.78 | NT | NT | NT |
| 77 | 15,000 | 5.77 | NT | NT | NT |
| 78 | 101 | 7.0 |  | 93 | 60–100 |
| 79 | 4.9 | 9.2 |  | 100 | >200 |
|  |  |  |  | 50 | >180 |
| 80 | 25 | 8.1 |  | NT | NT |
| 81 | 18 | 8.0 |  | 40 | 180 |
| 82 | 7.9 | 8.5 |  | 20 | 180 |
| 83 | 3.6 | 8.3 |  | 15 | >180 |
| 84 | 16 | 7.1 |  | 20 | 30 |
| 85 | 8.7 | 8.9 |  | NT | NT |
| 86 | 9 | 7.8 |  | NT | NT |
| 87 | 91 | 7.8 |  | NT | NT |
| 88 | 50 | 7.7 |  | NT | NT |
| 89 | 18 | 7.9 |  | NT | NT |
| 90 | 5.6 | 9.0 |  | NT | NT |
| 91 | 30 | 8.6 |  | 40 | >180 |
| 92 | 35 | 7.9 |  | NT | NT |
| 93 | 480 | NT |  | NT | NT |
| 94 | 5,800 | NT |  | NT | NT |
| 95 | 66 | 8.2 |  | NT | NT |
| 96 | 21 | 8.0 |  | NT | NT |
| 97 | 280 | 7.7 |  | NT | NT |
| 98 | 22 | 8.1 |  | NT | NT |
| 99 | 280 | 6.5 |  | NT | NT |
| 100 | 4.4 | 9.4 |  | NT | NT |
| 101 | 36 | 7.8 |  | NT | NT |
| 102 | 43 | 7.7 |  | NT | NT |
| 103 | 12 | 8.0 |  | NT | NT |

TABLE III-continued

In Vivo and In Vitro Angiotensin II Activity of Compounds of the Invention

| Test Compound Example # | [1]Assay A IC$_{50}$ (nM) | [2]Assay B pA$_2$ | Dose (mg/kg) | [3]Assay C Inhibition (%) | Duration (min.) |
|---|---|---|---|---|---|
| 104 | 15 | 8.0 | | NT | NT |
| 105 | 290 | 6.6 | | NT | NT |
| 106 | 48 | 7.7 | | NT | NT |
| 107 | 180 | 8.3 | | NT | NT |
| 108 | 720 | 5.3 | 100 | 45 | 90 |
| 109 | 250 | 7.3 | 30 | 50 | 30 |
| 110 | 590 | 6.4 | | NT | NT |
| 111 | 45 | 9.0 | 30 | 87 | 160 |
| 112 | 2000 | 5.2 | | NT | NT |
| 113 | 12 | 8.4 | 10 | 60 | 180 |
| 114 | 400 | 6.4 | | NT | |
| 115 | 11 | 8.2 | 3 | 40 | >240 |
| 116 | 230 | 6.5 | | NT | |
| 117 | 170 | 6.5 | | NT | |
| 118 | 37 | 9.21/9.17 | 10 | 70 | 120 |
| 119 | 16 | 9.21/9.00 | 3 | 20 | 60 |
| 120 | 25 | 9.05/8.77 | 10 | 80 | 240 |
| 121 | 46 | NT | | NT | |
| 122 | 46 | NT | | NT | |
| 123 | 50 | NT | | NT | |
| 124 | 40 | 9.42/9.12 | 3 | 45 | >180 |
| 125 | 40 | 9.25/8.80 | 3 | 35 | >240 |
| 126 | 240 | 7.20/7.05 | | NT | |
| 127 | 12,000 | 4.96 | | NT | |
| 128 | 16 | 8.63/8.40 | | NT | |
| 129 | 6,700 | 5.30 | | NT | |
| 130 | 40 | 8.10/7.94 | | NT | |
| 131 | 9.5 | 7.53/8.25 | | | |
| 132 | 12 | 8.6 | | NT | |
| 133 | 10 | 8.7 | 3 | 20 | 180 |
| | | | | | 90–120 |
| 134 | 22 | 9.3 | 3 | 35 | 180 |
| 135 | 16 | 8.5 | 3 | 35 | >180 |
| 136 | NT | NT | | NT | |
| 137 | 220 | 8.3 | | NT | |
| 138 | 130 | 8.2 | | NT | |
| 139 | 0.270 | 6.3 | | NT | |
| 140 | 0.031 | 8.1 | | 100 | 160 |
| 141 | 0.110 | 8.02 | | NT | NT |
| 142 | 2.000 | NA | | NT | NT |
| 143 | 0.052 | 7.7 | | 85 | 75 |
| 144 | 0.088 | 7.7 | | 50 | 125 |
| 145 | 0.480 | 6.7 | | NT | NT |
| 146 | 0.072 | 6.4 | | NT | NT |
| 147 | 5.8 | 5.6 | 3 | 74 | 5–10 |
| 148 | 0.87 | 5.8 | 3 | 92 | 20–30 |
| 149 | 1.1 | 6.1 | 3 | NT | NT |
| 150 | 14 | 8.03/7.80 | 3 | 25 | >180 |
| 151 | 17 | 7.76/7.97 | 3 | 15 | 180 |
| 152 | 150 | 7.46/7.23 | 3 | 10 | 140 |
| 153 | 13 | 8.30/7.69 | 3 | 25 | >180 |
| 154 | 97 | 8.19/8.38 | | NA | |
| 155 | 86 | 7.60/7.14 | | NA | |
| 156 | 78 | 8.03/7.66 | | NA | |
| 157 | 530 | —/6.22 | | NA | |
| 158 | 54 | 8.23/8.14 | 3 | 30 | >180 |
| 159 | 21 | 7.92/7.56 | 3 | 10 | 150 |
| 160 | 64 | 7.87/7.71 | | | |
| 161 | 28 | | | NA | |
| 162 | 380 | 6.21/6.55 | | NA | |
| 163 | 420 | 7.42/6.75 | | NA | |
| 164 | 1700 | | | NA | |
| 165 | 410 | 6.90/7.18 | | NA | |
| 166 | 160 | 7.57/7.74 | | NA | |
| 167 | 370 | 7.08/7.11 | | NA | |
| 168 | 420 | 7.69/7.58 | | NA | |
| 169 | 150 | 7.78/7.58 | 3 | 15 | 180 |
| 170 | 26 | 7.08/7.77 | 3 | 40 | >180 |
| 171 | 28 | 7.52/7.11 | 3 | 0 | 0 |
| 172 | 70 | 7.15/7.04 | | NA | |
| 173 | 90 | 7.49/6.92 | | NA | |
| 174 | 180 | 7.29/7.02 | | NA | |
| 175 | 27 | NA | 3 | 0 | 0 |
| 176 | 9.8 | 7.69/7.55 | 3 | 10 | 150 |
| 177 | 26 | 7.41/7.85 | 3 | 15 | 180 |
| 178 | 88 | 7.54/7.47 | | NA | |
| 179 | 310 | 6.67/— | | NA | |
| 180 | 20 | 7.56/7.15 | 3 | 25 | 180 |
| 181 | 21 | 7.70/7.12 | 3 | 20 | 180 |
| 182 | 59 | NA | | NA | |
| 183 | 390 | NA | | NA | |
| 184 | 1100 | 6.78/— | | NA | |
| 185 | 6.5 | 8.82/8.53 | 3 | 50 | >180 |
| 186 | 38 | 8.33/7.40 | 3 | 25 | 180 |
| 187 | 770 | 7.46/6.95 | | NA | |
| 188 | 140 | 7.72/7.09 | | NA | |
| 189 | 29 | 8.64/8.23 | | NA | |
| 190 | 10 | 7.87/7.89 | 3 | 10 | 180 |
| 191 | 81 | 7.75/7.76 | 3 | 10 | 180 |
| 192 | 140 | | | NA | |
| 193 | 11 | 9.27/8.87 | 3 | 10 | 180 |
| 194 | 47 | 7.64/7.35 | | NA | |
| 195 | 34 | 8.44/8.03 | | NA | |
| 196 | 31 | 7.68/8.26 | | NA | |
| 197 | 14 | 8.03/8.60 | | NA | |
| 198 | 7.6 | 8.76/8.64 | 3 | 35 | >180 |
| 199 | 10 | 8.79/8.85 | 3 | 60 | >180 |
| 200 | 20 | 8.42/8.77 | 3 | 45 | >180 |
| 201 | 17 | 8.78/8.63 | 3 | 10 | 180 |
| 202 | 12 | 8.79/8.64 | 3 | 65 | >180 |
| 203 | 9.2 | 8.43/8.36 | 3 | 50 | >180 |
| 204 | 16 | 9.17/8.86 | 3 | 75 | >180 |
| 205 | 20 | 9.14/9.15 | 3 | 40 | >180 |
| 206 | 5.4 | 8.75/8.89 | 3 | 30 | >180 |
| 207 | 99 | 9.04/8.60 | | NA | |
| 208 | 22 | 9.19/8.69 | 3 | 50 | >180 |
| 209 | 5.0 | 9.41/9.16 | 3 | 25 | >180 |
| 210 | 3.6 | 8.36/8.44 | 3 | 15 | 180 |
| 211 | 18 | 8.74/8.67 | 3 | 35 | >180 |
| 212 | 23 | 8.85/8.25 | 3 | 15 | 180 |
| 213 | 51 | NA | | NA | |
| 214 | 65 | NA | | NA | |
| 215 | 45 | NA | | NA | |
| 216 | 5.4 | 8.80/9.04 | 3 | 50 | >180 |
| 217 | 9.4 | NA | 3 | 65 | >180 |
| 218 | 9.0 | NA | | NA | |
| 219 | 14 | NA | | NA | |
| 220 | 7.0 | NA | 3 | 75 | 120 |
| 221 | 4.8 | NA | 3 | 25 | >180 |
| 222 | 5.0 | NA | | NA | |
| 223 | 14 | 7.45/7.87 | 3 | 20 | >180 |
| 224 | 91 | NA | | NA | |
| 225 | 160 | NA | | NA | |
| 226 | 93 | NA | | NA | |
| 227 | 89 | 7.55/7.67 | | NA | |
| 228 | 4.5 | 9.17/8.25 | 3 | 80 | >180 |
| 229 | 19 | NT | 3 | 40 | >180 |
| 230 | 2.6 | 8.23/8.69 | 3 | 25 | >180 |
| 231 | 3.6 | NT | 3 | 75 | >180 |
| 232 | 4.4 | 8.59/8.89 | 3 | 70 | >180 |
| 233 | 84 | 8.51/8.78 | | NT | |
| 234 | 5.0 | 8.49/9.00 | 3 | 20 | — |
| 235 | 34 | 7.14/7.07 | | NT | |
| 236 | 4.9 | NC | 3 | 70 | >180 |
| 237 | 3.6 | NT | | NT | |
| 238 | 1.7 | NT | 3 | 15 | >180 |
| 239 | 6.8 | 7.88/8.01 | 3 | 20 | >180 |
| 240 | 120 | NA | | NA | |
| 241 | 6.9 | 8.57/8.24 | 3 | 40 | >180 |
| 242 | 110 | 7.11/6.60 | | NA | |
| 243 | 250 | NA | | NA | |
| 244 | 150 | 7.17/7.17 | | NA | |

TABLE III-continued

In Vivo and In Vitro Angiotensin II
Activity of Compounds of the Invention

| Test Compound Example # | [1]Assay A IC$_{50}$ (nM) | [2]Assay B pA$_2$ | Dose (mg/kg) | [3]Assay C Inhibition (%) | Duration (min.) |
|---|---|---|---|---|---|
| 245 | 98 | 6.64/7.04 | | | NA |
| 246 | 72 | 7.46/7.59 | | | NA |
| 247 | 9.4 | 8.26/8.41 | 3 | 20 | 180 |
| 248 | 20 | 7.68/7.50 | 3 | 10 | — |
| 249 | 4.4 | NA | 3 | 20 | >180 |
| 250 | 43 | NA | 3 | 0 | — |
| 251 | 25 | NA | | NA | |
| 252 | 13 | NA | | NA | |
| 253 | 2.6 | NA | | NA | |
| 254 | 72 | NA | | NA | |
| 255 | 12 | 7.61/7.46 | 3 | 20 | >180 |
| 256 | 4.1 | 8.43/7.78 | 3 | 30 | >180 |
| 257 | 160 | 6.63/6.68 | | | NA |
| 258 | 350 | 6.84/6.84 | | | NA |
| 259 | 54 | NA | | | NA |
| 260 | 220 | NA | | | NA |
| 261 | 18 | NA | | | NA |
| 262 | 530 | —/6.22 | | | NA |
| 263 | 57 | NA | | | NA |
| 264 | 11 | NA | | | NA |
| 265 | 110 | NA | | | NA |
| 266 | 290 | NA | | | NA |
| 267 | 25 | NA | 3 | 25 | >180 |
| 268 | 520 | NA | 3 | 0 | — |
| 269 | 9.7 | NA | | | NA |
| 270 | 21 | NA | | | NA |
| 271 | 14 | NC | 3 | 20% | — |
| 272 | 97 | NC | 3 | 70% | >180 min. |
| 273 | 9.8 | 8.53/8.61 | 3 | 25% | >180 min. |
| 274 | 13 | 9.06/8.85 | 3 | 35% | >180 min. |
| 275 | 6.3 | 9.07/— | 3 | 40% | >180 min. |
| 276 | 33 | 8.71/8.64 | 3 | <20% | |
| 277 | 190 | —/6.54 | | | NT |
| 278 | 30 | 8.49/8.51 | 3 | 50% | >180 min. |
| 279 | 270 | 8.06/8.25 | | | NT |
| 280 | 480 | 6.41/6.35 | NT | NT | NT |

NT = NOT TESTED
NC = Non-Competitive antagonist
* Antagonist Activity not observed up to 10 µM of test compound.
[1]Assay A: Angiotensin II Binding Activity
[2]Assay B: In Vitro Vascular Smooth Muscle Response
[3]Assay C: In Vivo Pressor Response
Test Compounds administered intragastrically, except for compounds of examples #1–#2, #4–#25, #27–#29, #30–#79, #108–#109, #111, #118 and #139–#149 which were given intraduodenally.

Administration of the angiotensin II receptor antagonist and the aldosterone receptor antagonist may take place sequentially in separate formulations, or may be accomplished by simultaneous administration in a single formulation or separate formulations. Administration may be accomplished by oral route, or by intravenous, intramuscular or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, preservative, surface-active or dispersing agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of each active ingredient from about 1 to 250 mg, preferably from about 25 to 150 mg. A suitable daily dose for a mammal may vary widely depending on the condition of the patient and other factors. However, a dose of from about 0.01 to 30 mg/kg body weight, particularly from about 1 to 15 mg/kg body weight, may be appropriate.

The active ingredients may also be administered by injection as a composition wherein, for example, saline, dextrose or water may be used as a suitable carrier. A suitable daily dose of each active component is from about 0.01 to 15 mg/kg body weight injected per day in multiple doses depending on the disease being treated. A preferred daily dose would be from about 1 to 10 mg/kg body weight. Compounds indicated for prophylactic therapy will preferably be administered in a daily dose generally in a range from about 0.1 mg to about 15 mg per kilogram of body weight per day. A more preferred dosage will be a range from about 1 mg to about 15 mg per kilogram of body weight. Most preferred is a dosage in a range from about 1 to about 10 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

In combination therapy, the aldosterone receptor antagonist may be present in an amount in a range from about 5 mg to about 400 mg, and the AII antagonist may be present in an amount in a range from about 1 mg to about 800 mg, which represents aldosterone antagonist-to-AII antagonist ratios ranging from about 400:1 to about 1:160.

In a preferred combination therapy, the aldosterone receptor antagonist may be present in an amount in a range from about 10 mg to about 200 mg, and the AII antagonist may be present in an amount in a range from about 5 mg to about 600 mg, which represents aldosterone antagonist-to-AII antagonist ratios ranging from about 40:1 to about 1:60.

In a more preferred combination therapy, the aldosterone receptor antagonist may be present in an amount in a range from about 20 mg to about 100 mg, and the AII antagonist may be present in an amount in a range from about 10 mg to about 400 mg, which represents aldosterone antagonist-to-AII antagonist ratios ranging from about 10:1 to about 1:20.

The dosage regimen for treating a disease condition with the combination therapy of this invention is selected in accordance with a variety of factors, including the type, age, weight, sex and medical condition of the patient, the severity of the disease, the route of administration, and the particular compound employed, and thus may vary widely.

For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method to treat a subject susceptible to or afflicted with cardiofibrosis or cardiac hypertrophy, which method comprises administering to the subject a therapeutically-effective amount of an angiotensin II receptor antagonist and a therapeutically-effective amount of epoxymexrenone.

2. The method of claim 1 further characterized by said angiotensin II receptor antagonist and said epoxymexrenone being administered in a daily dose weight ratio range from about one-to-one about twenty-to-one of said angiotensin II receptor antagonist to said epoxymexrenone.

3. The method of claim 2 wherein said weight ratio range is from about five-to-one about fifteen-to-one.

4. The method of claim 3 wherein said weight ratio is about ten-to-one.

5. The method of claim 1 wherein the subject is susceptible to or afflicted with cardiofibrosis.

6. The method of claim 1 wherein the subject is susceptible to or afflicted with cardiac hypertrophy.

7. The method of claim 1 wherein said angiotensin II receptor antagonist is selected from the group consisting of valsartan, tasosartan, telmisartan, saprisartan, elisartan, ripisartan, losartan, irbesartan, candesartan, eprosartan, milfasartan and zolasartan.

8. The method of claim 1 wherein said angiotensin II receptor antagonist is valsartan.

9. The method of claim 1 wherein said angiotensin II receptor antagonist is tasosartan.

10. The method of claim 1 wherein said angiotensin II receptor antagonist is telmisartan.

11. The method of claim 1 wherein said angiotensin II receptor antagonist is saprisartan.

12. The method of claim 1 wherein said angiotensin II receptor antagonist is elisartan.

13. The method of claim 1 wherein said angiotensin II receptor antagonist is ripisartan.

14. The method o claim 1 wherein said angiotensin II receptor antagonist is losartan.

15. The method of claim 1 wherein said angiotensin II receptor antagonist is irbesartan.

16. The method of claim 1 wherein said angiotensin II receptor antagonist is candesartan.

17. The method of claim 1 wherein said angiotensin II receptor antagonist is eprosartan.

18. The method of claim 1 wherein said angiotensin II receptor antagonist is milfasartan.

19. The method of claim 1 wherein said angiotensin II receptor antagonist is zolasartan.

20. The method of claim 7 wherein the subject is susceptible to or afflicted with cardiofibrosis.

21. The method of claim 7 wherein the subject is susceptible to or afflicted with cardiac hypertrophy.

22. The method of claim 7 wherein said epoxymexrenone is administered in an amount in a range from about 5 to mg to about 400 mg.

23. The method of claim 7 wherein said epoxymexrenone is administered in an amount in a range from about 10 mg to about 200 mg.

24. The method of claim 7 wherein said epoxymexrenone is administered in an amount in a range from about 20 mg to about 100 mg.

* * * * *